United States Patent
Shelton, IV et al.

(10) Patent No.: US 12,226,070 B2
(45) Date of Patent: Feb. 18, 2025

(54) SYSTEM COMPRISING CONTROL CIRCUIT TO DETERMINE A PROPERTY OF A FLUID AT A SURGICAL SITE

(71) Applicant: Cilag GmbH International, Zug (CH)

(72) Inventors: Frederick E. Shelton, IV, Hillsboro, OH (US); Jason L. Harris, Lebanon, OH (US); David C Yates, West Chester, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/512,932

(22) Filed: Nov. 17, 2023

(65) Prior Publication Data
US 2024/0081611 A1    Mar. 14, 2024

Related U.S. Application Data

(63) Continuation of application No. 16/209,478, filed on Dec. 4, 2018, now Pat. No. 11,871,901.
(Continued)

(51) Int. Cl.
*A61B 9/00*       (2006.01)
*A61B 1/00*       (2006.01)
(Continued)

(52) U.S. Cl.
CPC .... *A61B 1/00006* (2013.01); *A61B 1/000094* (2022.02); *A61B 1/000096* (2022.02);
(Continued)

(58) Field of Classification Search
CPC ............ A61B 1/00006; A61B 1/00009; A61B 1/00039; A61B 1/0052; A61B 1/051;
(Continued)

(56) References Cited

U.S. PATENT DOCUMENTS

| 4,779,687 A | 10/1988 | Schreiber et al. |
| 5,607,436 A | 3/1997 | Pratt et al. |

(Continued)

FOREIGN PATENT DOCUMENTS

| CA | 2709634 A1 | 7/2009 |
| CN | 106027664 A | 10/2016 |

(Continued)

OTHER PUBLICATIONS

Anonymous: "Differentiated services—Wikipedia", Dec. 14, 2017, Retrieved from the Internet: URL:https://en.wikipedia.org/w/index.php?title=Differentiated_services&oldid=815415620 [retrieved on Feb. 14, 2023].

*Primary Examiner* — Howard D Brown, Jr.

(57) ABSTRACT

A computer-implemented method for contextually controlling a surgical device is disclosed. The method includes receiving, by a computer system, perioperative data from the surgical device, the perioperative data associated with a surgical procedure; receiving, by the computer system, images from a scope, the images visualizing the surgical device during the surgical procedure; determining, by the computer system, an attribute of the surgical device from the images; determining, by the computer system, procedural context data based at least on the perioperative data and the attribute of the surgical device; and controlling, by the computer system, the surgical device according to the procedural context data.

20 Claims, 28 Drawing Sheets

Related U.S. Application Data

(60) Provisional application No. 62/773,742, filed on Nov. 30, 2018, provisional application No. 62/750,539, filed on Oct. 25, 2018, provisional application No. 62/750,555, filed on Oct. 25, 2018, provisional application No. 62/750,529, filed on Oct. 25, 2018, provisional application No. 62/729,176, filed on Sep. 10, 2018, provisional application No. 62/729,185, filed on Sep. 10, 2018, provisional application No. 62/729,184, filed on Sep. 10, 2018, provisional application No. 62/729,191, filed on Sep. 10, 2018, provisional application No. 62/729,182, filed on Sep. 10, 2018, provisional application No. 62/729,183, filed on Sep. 10, 2018, provisional application No. 62/729,186, filed on Sep. 10, 2018, provisional application No. 62/729,195, filed on Sep. 10, 2018, provisional application No. 62/729,177, filed on Sep. 10, 2018, provisional application No. 62/721,999, filed on Aug. 23, 2018, provisional application No. 62/721,995, filed on Aug. 23, 2018, provisional application No. 62/721,998, filed on Aug. 23, 2018, provisional application No. 62/721,996, filed on Aug. 23, 2018, provisional application No. 62/721,994, filed on Aug. 23, 2018, provisional application No. 62/692,768, filed on Jun. 30, 2018, provisional application No. 62/692,748, filed on Jun. 30, 2018, provisional application No. 62/692,747, filed on Jun. 30, 2018, provisional application No. 62/691,251, filed on Jun. 28, 2018, provisional application No. 62/691,227, filed on Jun. 28, 2018, provisional application No. 62/691,257, filed on Jun. 28, 2018, provisional application No. 62/691,228, filed on Jun. 28, 2018, provisional application No. 62/691,219, filed on Jun. 28, 2018, provisional application No. 62/691,230, filed on Jun. 28, 2018, provisional application No. 62/691,262, filed on Jun. 28, 2018, provisional application No. 62/665,192, filed on May 1, 2018, provisional application No. 62/665,139, filed on May 1, 2018, provisional application No. 62/665,128, filed on May 1, 2018, provisional application No. 62/665,134, filed on May 1, 2018, provisional application No. 62/665,177, filed on May 1, 2018, provisional application No. 62/665,129, filed on May 1, 2018, provisional application No. 62/659,900, filed on Apr. 19, 2018, provisional application No. 62/650,887, filed on Mar. 30, 2018, provisional application No. 62/650,898, filed on Mar. 30, 2018, provisional application No. 62/650,882, filed on Mar. 30, 2018, provisional application No. 62/650,877, filed on Mar. 30, 2018, provisional application No. 62/649,327, filed on Mar. 28, 2018, provisional application No. 62/649,291, filed on Mar. 28, 2018, provisional application No. 62/649,296, filed on Mar. 28, 2018, provisional application No. 62/649,294, filed on Mar. 28, 2018, provisional application No. 62/649,333, filed on Mar. 28, 2018, provisional application No. 62/649,323, filed on Mar. 28, 2018, provisional application No. 62/649,320, filed on Mar. 28, 2018, provisional application No. 62/649,302, filed on Mar. 28, 2018, provisional application No. 62/649,300, filed on Mar. 28, 2018, provisional application No. 62/649,307, filed on Mar. 28, 2018, provisional application No. 62/649,309, filed on Mar. 28, 2018, provisional application No. 62/649,315, filed on Mar. 28, 2018, provisional application No. 62/649,313, filed on Mar. 28, 2018, provisional application No. 62/611,339, filed on Dec. 28, 2017, provisional application No. 62/611,341, filed on Dec. 1, 2017, provisional application No. 62/611,340, filed on Dec. 28, 2017.

(51) Int. Cl.

| | | |
|---|---|---|
| *A61B 1/005* | (2006.01) | |
| *A61B 1/05* | (2006.01) | |
| *A61B 1/06* | (2006.01) | |
| *A61B 5/00* | (2006.01) | |
| *A61B 18/00* | (2006.01) | |
| *A61B 18/14* | (2006.01) | |
| *A61B 34/00* | (2016.01) | |
| *A61B 34/37* | (2016.01) | |
| *A61B 90/00* | (2016.01) | |
| *G16H 40/60* | (2018.01) | |
| *A61B 5/02* | (2006.01) | |
| *A61B 5/021* | (2006.01) | |
| *A61B 5/026* | (2006.01) | |
| *A61B 5/318* | (2021.01) | |
| *A61B 17/00* | (2006.01) | |
| *A61B 17/068* | (2006.01) | |
| *G06T 7/20* | (2017.01) | |
| *G06T 7/70* | (2017.01) | |

(52) U.S. Cl.
CPC ........ *A61B 1/00042* (2022.02); *A61B 1/0052* (2013.01); *A61B 1/051* (2013.01); *A61B 1/0661* (2013.01); *A61B 1/0684* (2013.01); *A61B 5/0071* (2013.01); *A61B 18/00* (2013.01); *A61B 18/1445* (2013.01); *A61B 34/25* (2016.02); *A61B 34/37* (2016.02); *A61B 90/361* (2016.02); *G16H 40/60* (2018.01); *A61B 5/0035* (2013.01); *A61B 5/02042* (2013.01); *A61B 5/021* (2013.01); *A61B 5/026* (2013.01); *A61B 5/318* (2021.01); *A61B 5/4821* (2013.01); *A61B 5/7264* (2013.01); *A61B 2017/00022* (2013.01); *A61B 2017/00044* (2013.01); *A61B 2017/00061* (2013.01); *A61B 2017/00106* (2013.01); *A61B 2017/00119* (2013.01); *A61B 2017/00442* (2013.01); *A61B 17/068* (2013.01); *A61B 2034/254* (2016.02); *A61B 2090/061* (2016.02); *A61B 2090/365* (2016.02); *A61B 2218/008* (2013.01); *A61B 2505/05* (2013.01); *G06T 7/20* (2013.01); *G06T 7/70* (2017.01); *G06T 2207/10068* (2013.01); *G06V 2201/034* (2022.01)

(58) Field of Classification Search
CPC ... A61B 1/0661; A61B 1/0684; A61B 5/0071; A61B 18/00; A61B 18/1445; A61B 34/25; A61B 34/37; A61B 90/361; A61B 5/0035; A61B 5/02042; A61B 5/021; A61B 5/026; A61B 5/318; A61B 5/4821; A61B 5/7264; A61B 17/068; A61B 2017/00022; A61B 2017/00044; A61B 2017/00061; A61B 2017/00106; A61B 2017/00119; A61B 2017/00442; A61B 2034/254; A61B 2090/061; A61B 2090/365; A61B 2218/008; A61B 2505/05; A61B 1/000094; A61B 1/000096; A61B 1/00042; G06V 20/00; G06V 2201/034; G06V 2201/03; G16H 40/60; G16H 20/40; G16H 40/20; G16H 40/67; G06T 7/20; G06T 7/70; G06T 2207/10068; G06K 9/6274
See application file for complete search history.

(56) References Cited

U.S. PATENT DOCUMENTS

| | | | |
|---|---|---|---|
| 5,619,881 | A | 4/1997 | Morikawa et al. |
| 7,982,776 | B2 | 7/2011 | Dunki-Jacobs et al. |
| 7,995,045 | B2 | 8/2011 | Dunki-Jacobs |
| 8,535,342 | B2 | 9/2013 | Malackowski et al. |
| 8,543,240 | B2 | 9/2013 | Itkowitz et al. |
| 9,033,973 | B2 | 5/2015 | Krapohl et al. |
| 9,498,279 | B2 | 11/2016 | Artale et al. |
| 9,662,104 | B1 | 5/2017 | Nobles et al. |
| 9,775,623 | B2 | 10/2017 | Zammataro et al. |
| 9,808,305 | B2 | 11/2017 | Hareyama et al. |
| 9,905,000 | B2 * | 2/2018 | Chou .................. A61B 90/37 |
| 10,052,147 | B2 | 8/2018 | Merschon et al. |
| 10,098,527 | B2 | 10/2018 | Weisenburgh, II et al. |
| 10,187,742 | B2 | 1/2019 | Dor et al. |
| 10,318,928 | B1 | 6/2019 | Kestone et al. |
| 10,376,337 | B2 | 8/2019 | Kilroy et al. |
| 10,537,667 | B2 | 1/2020 | Anim |
| 10,565,170 | B2 | 2/2020 | Walling et al. |
| 10,595,887 | B2 | 3/2020 | Shelton, IV et al. |
| 10,660,705 | B2 * | 5/2020 | Piron .................. G16H 50/50 |
| 10,695,081 | B2 | 6/2020 | Shelton, IV et al. |
| 10,755,813 | B2 | 8/2020 | Shelton, IV et al. |
| 10,758,310 | B2 | 9/2020 | Shelton, IV et al. |
| 10,772,651 | B2 | 9/2020 | Shelton, IV et al. |
| 10,838,210 | B2 | 11/2020 | Robaina et al. |
| 10,849,697 | B2 | 12/2020 | Yates et al. |
| 10,874,396 | B2 | 12/2020 | Moore et al. |
| 10,892,899 | B2 | 1/2021 | Shelton, IV et al. |
| 10,892,995 | B2 | 1/2021 | Shelton, IV et al. |
| 10,898,622 | B2 | 1/2021 | Shelton, IV et al. |
| 10,932,806 | B2 | 3/2021 | Shelton, IV et al. |
| 10,932,872 | B2 | 3/2021 | Shelton, IV et al. |
| 10,943,454 | B2 | 3/2021 | Shelton, IV et al. |
| 10,944,728 | B2 | 3/2021 | Wiener et al. |
| 10,959,744 | B2 | 3/2021 | Shelton, IV et al. |
| 10,966,791 | B2 | 4/2021 | Harris et al. |
| 10,980,560 | B2 | 4/2021 | Shelton, IV et al. |
| 10,987,178 | B2 | 4/2021 | Shelton, IV et al. |
| 11,013,563 | B2 | 5/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,045,197 | B2 | 6/2021 | Shelton, IV et al. |
| 11,045,591 | B2 | 6/2021 | Shelton, IV et al. |
| 11,051,836 | B2 | 7/2021 | Shelton, IV et al. |
| 11,051,876 | B2 | 7/2021 | Shelton, IV et al. |
| 11,056,244 | B2 | 7/2021 | Shelton, IV et al. |
| 11,058,498 | B2 | 7/2021 | Shelton, IV et al. |
| 11,069,012 | B2 | 7/2021 | Shelton, IV et al. |
| 11,071,560 | B2 | 7/2021 | Deck et al. |
| 11,076,921 | B2 | 8/2021 | Shelton, IV et al. |
| 11,096,693 | B2 | 8/2021 | Shelton, IV et al. |
| 11,100,631 | B2 | 8/2021 | Yates et al. |
| 11,103,268 | B2 | 8/2021 | Shelton, IV et al. |
| 11,109,866 | B2 | 9/2021 | Shelton, IV et al. |
| 11,109,878 | B2 | 9/2021 | Shelton, IV et al. |
| 11,114,195 | B2 | 9/2021 | Shelton, IV et al. |
| 11,123,070 | B2 | 9/2021 | Shelton, IV et al. |
| 11,129,636 | B2 | 9/2021 | Shelton, IV et al. |
| 11,132,462 | B2 | 9/2021 | Shelton, IV et al. |
| 11,141,160 | B2 | 10/2021 | Shelton, IV et al. |
| 11,147,607 | B2 | 10/2021 | Yates et al. |
| 11,160,605 | B2 | 11/2021 | Shelton, IV et al. |
| 11,166,772 | B2 | 11/2021 | Shelton, IV et al. |
| 11,179,175 | B2 | 11/2021 | Houser et al. |
| 11,179,208 | B2 | 11/2021 | Yates et al. |
| 11,202,570 | B2 | 12/2021 | Shelton, IV et al. |
| 11,207,090 | B2 | 12/2021 | Shelton, IV et al. |
| 11,213,359 | B2 | 1/2022 | Shelton, IV et al. |
| 11,229,436 | B2 | 1/2022 | Shelton, IV et al. |
| 11,234,756 | B2 | 2/2022 | Shelton, IV et al. |
| 11,253,315 | B2 | 2/2022 | Yates et al. |
| 11,257,589 | B2 | 2/2022 | Shelton, IV et al. |
| 11,266,468 | B2 | 3/2022 | Shelton, IV et al. |
| 11,273,001 | B2 | 3/2022 | Shelton, IV et al. |
| 11,278,281 | B2 | 3/2022 | Shelton, IV et al. |
| 11,284,936 | B2 | 3/2022 | Shelton, IV et al. |
| 11,291,465 | B2 | 4/2022 | Parihar et al. |
| 11,291,495 | B2 | 4/2022 | Yates et al. |
| 11,291,510 | B2 | 4/2022 | Shelton, IV et al. |
| 11,304,699 | B2 | 4/2022 | Shelton, IV et al. |
| 11,304,720 | B2 | 4/2022 | Kimball et al. |
| 11,304,745 | B2 | 4/2022 | Shelton, IV et al. |
| 11,304,763 | B2 | 4/2022 | Shelton, IV et al. |
| 11,308,075 | B2 | 4/2022 | Shelton, IV et al. |
| 11,311,306 | B2 | 4/2022 | Shelton, IV et al. |
| 11,311,342 | B2 | 4/2022 | Parihar et al. |
| 11,317,919 | B2 | 5/2022 | Shelton, IV et al. |
| 11,317,937 | B2 | 5/2022 | Nott et al. |
| 11,364,075 | B2 | 6/2022 | Yates et al. |
| 11,376,002 | B2 | 7/2022 | Shelton, IV et al. |
| 11,389,164 | B2 | 7/2022 | Yates et al. |
| 11,406,390 | B2 | 8/2022 | Shelton, IV et al. |
| 11,410,259 | B2 | 8/2022 | Harris et al. |
| 11,413,042 | B2 | 8/2022 | Shelton, IV et al. |
| 11,419,630 | B2 | 8/2022 | Yates et al. |
| 11,419,667 | B2 | 8/2022 | Messerly et al. |
| 11,423,007 | B2 | 8/2022 | Shelton, IV et al. |
| 11,432,885 | B2 | 9/2022 | Shelton, IV et al. |
| 11,446,052 | B2 | 9/2022 | Shelton, IV et al. |
| 11,464,535 | B2 | 10/2022 | Shelton, IV et al. |
| 11,464,559 | B2 | 10/2022 | Nott et al. |
| 11,464,971 | B2 | 10/2022 | Schepis et al. |
| 11,504,192 | B2 | 11/2022 | Shelton, IV et al. |
| 11,510,741 | B2 | 11/2022 | Shelton, IV et al. |
| 11,529,187 | B2 | 12/2022 | Shelton, IV et al. |
| 11,540,855 | B2 | 1/2023 | Messerly et al. |
| 11,559,307 | B2 | 1/2023 | Shelton, IV et al. |
| 11,559,308 | B2 | 1/2023 | Yates et al. |
| 11,564,703 | B2 | 1/2023 | Shelton, IV et al. |
| 11,564,756 | B2 | 1/2023 | Shelton, IV et al. |
| 11,571,234 | B2 | 2/2023 | Nott et al. |
| 11,576,677 | B2 | 2/2023 | Shelton, IV et al. |
| 11,589,888 | B2 | 2/2023 | Shelton, IV et al. |
| 11,602,366 | B2 | 3/2023 | Shelton, IV et al. |
| 11,602,393 | B2 | 3/2023 | Shelton, IV et al. |
| 11,602,612 | B2 | 3/2023 | Hara et al. |
| 11,612,408 | B2 | 3/2023 | Yates et al. |
| 11,612,444 | B2 | 3/2023 | Shelton, IV et al. |
| 11,633,237 | B2 | 4/2023 | Shelton, IV et al. |
| 11,648,022 | B2 | 5/2023 | Shelton, IV |
| 11,659,023 | B2 | 5/2023 | Shelton, IV et al. |
| 11,666,331 | B2 | 6/2023 | Shelton, IV et al. |
| 11,672,605 | B2 | 6/2023 | Messerly et al. |
| 11,678,881 | B2 | 6/2023 | Yates et al. |
| 11,696,760 | B2 | 7/2023 | Shelton, IV et al. |
| 11,696,778 | B2 | 7/2023 | Shelton, IV et al. |
| 11,759,224 | B2 | 9/2023 | Shelton, IV et al. |
| 11,771,487 | B2 | 10/2023 | Shelton, IV et al. |
| 11,786,245 | B2 | 10/2023 | Shelton, IV |
| 11,793,537 | B2 | 10/2023 | Shelton, IV et al. |
| 11,801,098 | B2 | 10/2023 | Stokes et al. |
| 11,818,052 | B2 | 11/2023 | Shelton, IV et al. |
| 11,819,231 | B2 | 11/2023 | Shelton, IV et al. |
| 11,832,899 | B2 | 12/2023 | Shelton, IV et al. |
| 11,844,579 | B2 | 12/2023 | Shelton, IV et al. |
| 11,857,152 | B2 | 1/2024 | Shelton, IV et al. |
| 11,864,728 | B2 | 1/2024 | Shelton, IV et al. |
| 11,871,901 | B2 | 1/2024 | Shelton, IV et al. |
| 11,896,322 | B2 | 2/2024 | Yates et al. |
| 11,896,443 | B2 | 2/2024 | Shelton, IV et al. |
| 2003/0195662 | A1 | 10/2003 | Wang et al. |
| 2003/0208465 | A1 | 11/2003 | Yurko et al. |
| 2004/0044546 | A1 | 3/2004 | Moore |
| 2004/0097913 | A1 | 5/2004 | Refior et al. |
| 2004/0215131 | A1 | 10/2004 | Sakurai |
| 2007/0005002 | A1 | 1/2007 | Millman et al. |
| 2007/0073389 | A1 | 3/2007 | Bolduc et al. |

(56) References Cited

U.S. PATENT DOCUMENTS

| | | |
|---|---|---|
| 2007/0156139 A1 | 7/2007 | Schechter et al. |
| 2007/0161979 A1 | 7/2007 | McPherson |
| 2007/0173811 A1 | 7/2007 | Couture et al. |
| 2007/0225556 A1 | 9/2007 | Ortiz et al. |
| 2007/0270660 A1* | 11/2007 | Caylor, III ............. A61B 34/20 600/300 |
| 2007/0270688 A1 | 11/2007 | Gelbart et al. |
| 2008/0147086 A1 | 6/2008 | Pfister et al. |
| 2009/0093702 A1 | 4/2009 | Vollmer et al. |
| 2009/0138095 A1 | 5/2009 | Giordano |
| 2009/0157695 A1 | 6/2009 | Roberts |
| 2010/0036192 A1 | 2/2010 | Yao et al. |
| 2010/0198220 A1 | 8/2010 | Boudreaux et al. |
| 2011/0015649 A1 | 1/2011 | Anvari et al. |
| 2011/0222746 A1 | 9/2011 | Kotula et al. |
| 2011/0306840 A1 | 12/2011 | Allen et al. |
| 2012/0080498 A1 | 4/2012 | Shelton, IV et al. |
| 2012/0130180 A1 | 5/2012 | Pell et al. |
| 2012/0203143 A1 | 8/2012 | Sanai et al. |
| 2013/0085413 A1 | 4/2013 | Tsamir et al. |
| 2013/0191154 A1 | 7/2013 | William R et al. |
| 2013/0261503 A1 | 10/2013 | Sherman et al. |
| 2014/0207124 A1 | 7/2014 | Aldridge et al. |
| 2015/0033128 A1 | 1/2015 | Curd et al. |
| 2015/0142016 A1 | 5/2015 | Bolduc et al. |
| 2015/0157410 A1* | 6/2015 | Kilroy ................. A61B 90/10 606/130 |
| 2015/0224237 A1 | 8/2015 | Reasoner et al. |
| 2015/0238118 A1 | 8/2015 | Legassey et al. |
| 2015/0282796 A1 | 10/2015 | Nawana et al. |
| 2015/0286787 A1 | 10/2015 | Chen et al. |
| 2015/0289820 A1 | 10/2015 | Miller et al. |
| 2015/0331995 A1 | 11/2015 | Zhao et al. |
| 2016/0103810 A1 | 4/2016 | Hanning |
| 2016/0143693 A1 | 5/2016 | Yilmaz et al. |
| 2016/0184469 A1 | 6/2016 | Welch et al. |
| 2016/0192999 A1 | 7/2016 | Stulen et al. |
| 2016/0354155 A1 | 12/2016 | Hodges et al. |
| 2016/0356852 A1 | 12/2016 | Lee |
| 2017/0056038 A1 | 3/2017 | Hess et al. |
| 2017/0147759 A1 | 5/2017 | Lyer et al. |
| 2017/0161443 A1 | 6/2017 | Bassham et al. |
| 2017/0196562 A1 | 7/2017 | Shelton, IV et al. |
| 2017/0202305 A1 | 7/2017 | Huard et al. |
| 2017/0235897 A1 | 8/2017 | Henderson et al. |
| 2017/0252095 A1 | 9/2017 | Johnson |
| 2017/0254013 A1 | 9/2017 | Pratt et al. |
| 2017/0270323 A1 | 9/2017 | Butler et al. |
| 2017/0296301 A1 | 10/2017 | Dor et al. |
| 2017/0337493 A1 | 11/2017 | Paramasivan et al. |
| 2018/0028088 A1 | 2/2018 | Garbey et al. |
| 2018/0110398 A1 | 4/2018 | Schwartz et al. |
| 2018/0168739 A1 | 6/2018 | Alikhani et al. |
| 2018/0289434 A1 | 10/2018 | Palo et al. |
| 2018/0345501 A1 | 12/2018 | Jumis et al. |
| 2018/0349721 A1 | 12/2018 | Agrawal et al. |
| 2019/0006047 A1* | 1/2019 | Gorek ................. G06F 18/25 |
| 2019/0083809 A1 | 3/2019 | Zhang |
| 2019/0104919 A1* | 4/2019 | Shelton, IV ........... A61B 18/00 |
| 2019/0105468 A1 | 4/2019 | Kato et al. |
| 2019/0125320 A1 | 5/2019 | Shelton, IV et al. |
| 2019/0125336 A1 | 5/2019 | Deck et al. |
| 2019/0125361 A1 | 5/2019 | Shelton, IV et al. |
| 2019/0125432 A1 | 5/2019 | Shelton, IV et al. |
| 2019/0125476 A1 | 5/2019 | Shelton, IV et al. |
| 2019/0200844 A1 | 7/2019 | Shelton, IV et al. |
| 2019/0200906 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0200997 A1 | 7/2019 | Shelton, IV et al. |
| 2019/0201021 A1 | 7/2019 | Shelton, IV et al. |
| 2019/0201034 A1 | 7/2019 | Shelton, IV et al. |
| 2019/0201039 A1 | 7/2019 | Widenhouse et al. |
| 2019/0201042 A1 | 7/2019 | Nott et al. |
| 2019/0201045 A1 | 7/2019 | Yates et al. |
| 2019/0201087 A1 | 7/2019 | Shelton, IV et al. |
| 2019/0201090 A1 | 7/2019 | Shelton, IV et al. |
| 2019/0201102 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201130 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201146 A1 | 7/2019 | Shelton, IV et al. |
| 2019/0201594 A1 | 7/2019 | Shelton, IV et al. |
| 2019/0205567 A1 | 7/2019 | Shelton, IV et al. |
| 2019/0206555 A1 | 7/2019 | Morgan et al. |
| 2019/0206561 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0216452 A1 | 7/2019 | Nawana et al. |
| 2019/0325386 A1 | 10/2019 | Aster et al. |
| 2019/0333626 A1* | 10/2019 | Mansi ................. A61B 5/7267 |
| 2020/0022687 A1 | 1/2020 | Takemoto et al. |
| 2020/0222079 A1 | 7/2020 | Swaney et al. |
| 2020/0237452 A1* | 7/2020 | Wolf ....................... G06F 3/048 |
| 2020/0273581 A1* | 8/2020 | Wolf ..................... G16H 40/63 |
| 2022/0061836 A1 | 3/2022 | Parihar et al. |
| 2022/0104880 A1 | 4/2022 | Frushour |
| 2022/0157306 A1* | 5/2022 | Albrecht ................ G06F 3/167 |
| 2023/0171266 A1 | 6/2023 | Brunner et al. |
| 2023/0187060 A1 | 6/2023 | Morgan et al. |
| 2023/0190390 A1 | 6/2023 | Shelton, IV et al. |
| 2023/0200889 A1 | 6/2023 | Shelton, IV et al. |
| 2023/0210611 A1 | 7/2023 | Shelton, IV et al. |
| 2023/0233245 A1 | 7/2023 | Nott et al. |
| 2023/0263548 A1 | 8/2023 | Shelton, IV et al. |
| 2023/0320792 A1 | 10/2023 | Shelton, IV et al. |
| 2023/0355265 A1 | 11/2023 | Nott et al. |
| 2023/0389796 A1 | 12/2023 | Shelton, IV et al. |
| 2023/0395250 A1 | 12/2023 | Denzinger et al. |
| 2023/0397960 A1 | 12/2023 | Shelton, IV et al. |
| 2023/0414294 A1 | 12/2023 | Shelton, IV et al. |
| 2024/0000521 A1 | 1/2024 | Stokes et al. |
| 2024/0081611 A1* | 3/2024 | Shelton, IV ......... A61B 90/361 |

FOREIGN PATENT DOCUMENTS

| | | |
|---|---|---|
| CN | 106456169 A | 2/2017 |
| CN | 106777916 A | 5/2017 |
| JP | 2012240158 A | 12/2012 |
| JP | 2017096359 A | 6/2017 |
| RU | 2020860 C1 | 10/1994 |

\* cited by examiner

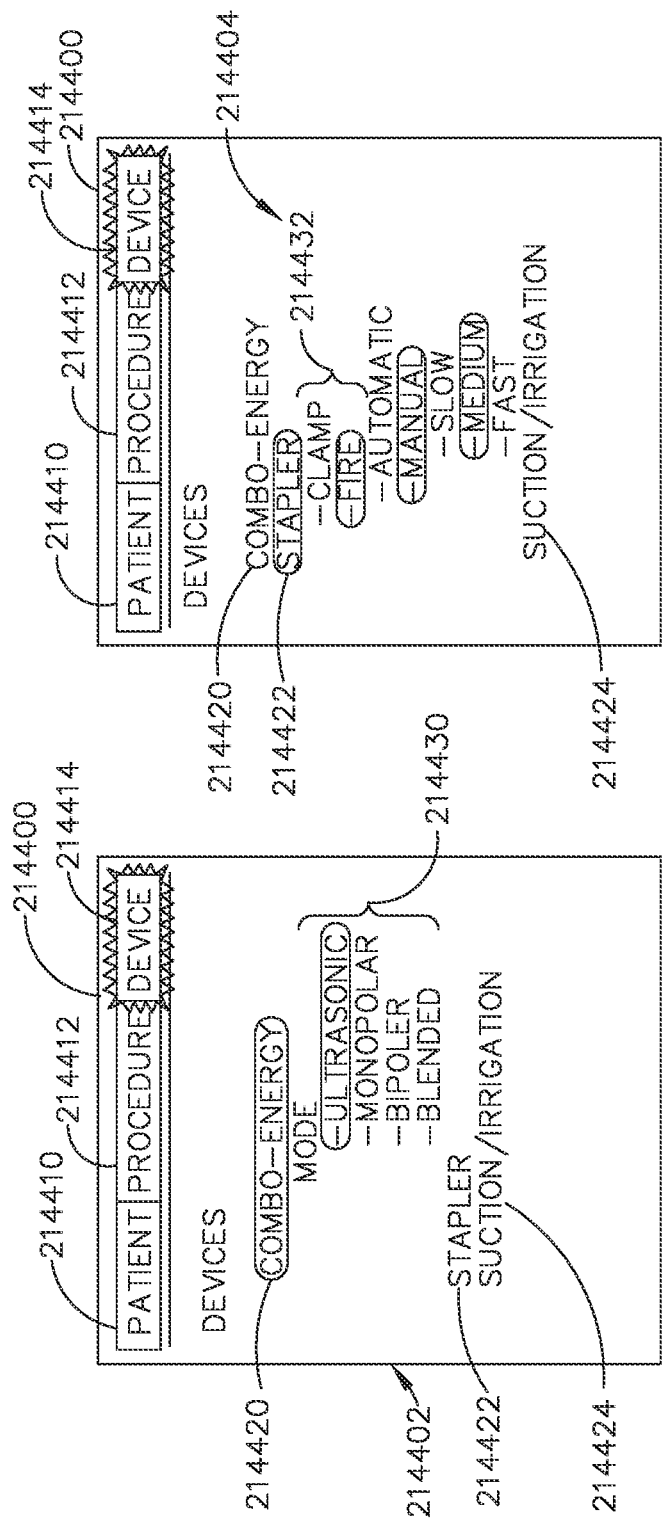

SYSTEM COMPRISING CONTROL CIRCUIT TO DETERMINE A PROPERTY OF A FLUID AT A SURGICAL SITE

CROSS-REFERENCE TO RELATED APPLICATIONS

This application is a continuation application claiming priority under 35 U.S.C. § 120 to U.S. patent application Ser. No. 16/209,478, entitled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018, now U.S. Patent Application Publication No. 2019/0104919, the disclosure of which is herein incorporated by reference in its entirety.

The present application claims priority under 35 U.S.C. § 119(e) to U.S. Provisional Patent Application No. 62/773,778, titled METHOD FOR ADAPTIVE CONTROL SCHEMES FOR SURGICAL NETWORK CONTROL AND INTERACTION, filed Nov. 30, 2018, to U.S. Provisional Patent Application No. 62/773,728, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Nov. 30, 2018, to U.S. Provisional Patent Application No. 62/773,741, titled METHOD FOR FACILITY DATA COLLECTION AND INTERPRETATION, filed Nov. 30, 2018, and to U.S. Provisional Patent Application No. 62/773,742, titled METHOD FOR CIRCULAR STAPLER CONTROL ALGORITHM ADJUSTMENT BASED ON SITUATIONAL AWARENESS, filed Nov. 30, 2018, the disclosure of each of which is herein incorporated by reference in its entirety.

The present application claims priority under 35 U.S.C. § 119(e) to U.S. Provisional Patent Application No. 62/750,529, titled METHOD FOR OPERATING A POWERED ARTICULATING MULTI-CLIP APPLIER, filed Oct. 25, 2018, to U.S. Provisional Patent Application No. 62/750,539, titled SURGICAL CLIP APPLIER, filed Oct. 25, 2018, and to U.S. Provisional Patent Application No. 62/750,555, titled SURGICAL CLIP APPLIER, filed Oct. 25, 2018, the disclosure of each of which is herein incorporated by reference in its entirety.

The present application also claims priority under 35 U.S.C. § 119(e) to U.S. Provisional Patent Application No. 62/729,183, titled CONTROL FOR A SURGICAL NETWORK OR SURGICAL NETWORK CONNECTED DEVICE THAT ADJUSTS ITS FUNCTION BASED ON A SENSED SITUATION OR USAGE, filed Sep. 10, 2018, to U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION, filed Sep. 10, 2018, to U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES, filed Sep. 10, 2018, to U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING, filed Sep. 10, 2018, to U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT, filed Sep. 10, 2018, to U.S. Provisional Patent Application No. 62/729,182, titled SENSING THE PATIENT POSITION AND CONTACT UTILIZING THE MONO-POLAR RETURN PAD ELECTRODE TO PROVIDE SITUATIONAL AWARENESS TO THE HUB, filed Sep. 10, 2018, to U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Sep. 10, 2018, to U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Sep. 10, 2018, and to U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, filed Sep. 10, 2018, the disclosure of each of which is herein incorporated by reference in its entirety.

The present application also claims priority under 35 U.S.C. § 119(e) to U.S. Provisional Patent Application No. 62/721,995, titled CONTROLLING AN ULTRASONIC SURGICAL INSTRUMENT ACCORDING TO TISSUE LOCATION, filed Aug. 23, 2018, to U.S. Provisional Patent Application No. 62/721,998, titled SITUATIONAL AWARENESS OF ELECTROSURGICAL SYSTEMS, filed Aug. 23, 2018, to U.S. Provisional Patent Application No. 62/721,999, titled INTERRUPTION OF ENERGY DUE TO INADVERTENT CAPACITIVE COUPLING, filed Aug. 23, 2018, to U.S. Provisional Patent Application No. 62/721,994, titled BIPOLAR COMBINATION DEVICE THAT AUTOMATICALLY ADJUSTS PRESSURE BASED ON ENERGY MODALITY, filed Aug. 23, 2018, and to U.S. Provisional Patent Application No. 62/721,996, titled RADIO FREQUENCY ENERGY DEVICE FOR DELIVERING COMBINED ELECTRICAL SIGNALS, filed Aug. 23, 2018, the disclosure of each of which is herein incorporated by reference in its entirety.

The present application also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

The present application also claims priority under 35 U.S.C. § 119(e) to U.S. Provisional Patent Application No. 62/691,228, titled METHOD OF USING REINFORCED FLEX CIRCUITS WITH MULTIPLE SENSORS WITH ELECTROSURGICAL DEVICES, filed Jun. 28, 2018, to U.S. Provisional Patent Application No. 62/691,227, titled CONTROLLING A SURGICAL INSTRUMENT ACCORDING TO SENSED CLOSURE PARAMETERS, filed Jun. 28, 2018, to U.S. Provisional Patent Application No. 62/691,230, titled SURGICAL INSTRUMENT HAVING A FLEXIBLE ELECTRODE, filed Jun. 28, 2018, to U.S. Provisional Patent Application No. 62/691,219, titled SURGICAL EVACUATION SENSING AND MOTOR CONTROL, filed Jun. 28, 2018, to U.S. Provisional Patent Application No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, filed Jun. 28, 2018, to U.S. Provisional Patent Application No. 62/691, 262, titled SURGICAL EVACUATION SYSTEM WITH A COMMUNICATION CIRCUIT FOR COMMUNICATION BETWEEN A FILTER AND A SMOKE EVACUATION DEVICE, filed Jun. 28, 2018, and to U.S. Provisional Patent Application No. 62/691,251, titled DUAL IN-SERIES LARGE AND SMALL DROPLET FILTERS, filed Jun. 28, 2018, the disclosure of each of which is herein incorporated by reference in its entirety.

The present application claims priority under 35 U.S.C. § 119(e) to U.S. Provisional Patent Application No. 62/665, 129, titled SURGICAL SUTURING SYSTEMS, filed May 1, 2018, to U.S. Provisional Patent Application No. 62/665, 139, titled SURGICAL INSTRUMENTS COMPRISING CONTROL SYSTEMS, filed May 1, 2018, to U.S. Provisional Patent Application No. 62/665,177, titled SURGICAL INSTRUMENTS COMPRISING HANDLE ARRANGEMENTS, filed May 1, 2018, to U.S. Provisional Patent Application No. 62/665,128, titled MODULAR SURGICAL INSTRUMENTS, filed May 1, 2018, to U.S. Provisional Patent Application No. 62/665,192, titled SURGICAL DISSECTORS, filed May 1, 2018, and to U.S. Provisional Patent Application No. 62/665,134, titled SURGICAL CLIP APPLIER, filed May 1, 2018, the disclosure of each of which is herein incorporated by reference in its entirety.

The present application also claims priority under 35 U.S.C. § 119(e) to U.S. Provisional Patent Application No. 62/659,900, titled METHOD OF HUB COMMUNICATION, filed on Apr. 19, 2018, the disclosure of which is herein incorporated by reference in its entirety.

The present application also claims priority under 35 U.S.C. § 119(e) to U.S. Provisional Patent Application No. 62/650,898, filed on Mar. 30, 2018, titled CAPACITIVE COUPLED RETURN PATH PAD WITH SEPARABLE ARRAY ELEMENTS, to U.S. Provisional Patent Application No. 62/650,887, titled SURGICAL SYSTEMS WITH OPTIMIZED SENSING CAPABILITIES, filed Mar. 30, 2018, to U.S. Provisional Patent Application No. 62/650, 882, titled SMOKE EVACUATION MODULE FOR INTERACTIVE SURGICAL PLATFORM, filed Mar. 30, 2018, and to U.S. Provisional Patent Application No. 62/650,877, titled SURGICAL SMOKE EVACUATION SENSING AND CONTROLS, filed Mar. 30, 2018, the disclosure of each of which is herein incorporated by reference in its entirety.

This application also claims the benefit of priority under 35 U.S.C. § 119(e) to U.S. Provisional Patent Application No. 62/649,302, titled INTERACTIVE SURGICAL SYSTEMS WITH ENCRYPTED COMMUNICATION CAPABILITIES, filed Mar. 28, 2018, to U.S. Provisional Patent Application No. 62/649,294, titled DATA STRIPPING METHOD TO INTERROGATE PATIENT RECORDS AND CREATE ANONYMIZED RECORD, filed Mar. 28, 2018, to U.S. Provisional Patent Application No. 62/649, 300, titled SURGICAL HUB SITUATIONAL AWARENESS, filed Mar. 28, 2018, to U.S. Provisional Patent Application No. 62/649,309, titled SURGICAL HUB SPATIAL AWARENESS TO DETERMINE DEVICES IN OPERATING THEATER, filed Mar. 28, 2018, to U.S. Provisional Patent Application No. 62/649,310, titled COMPUTER IMPLEMENTED INTERACTIVE SURGICAL SYSTEMS, filed Mar. 28, 2018, to U.S. Provisional Patent Application No. 62/649,291, titled USE OF LASER LIGHT AND RED-GREEN-BLUE COLORATION TO DETERMINE PROPERTIES OF BACK SCATTERED LIGHT, filed Mar. 28, 2018, to U.S. Provisional Patent Application No. 62/649,296, titled ADAPTIVE CONTROL PROGRAM UPDATES FOR SURGICAL DEVICES, filed Mar. 28, 2018, to U.S. Provisional Patent Application No. 62/649, 333, titled CLOUD-BASED MEDICAL ANALYTICS FOR CUSTOMIZATION AND RECOMMENDATIONS TO A USER, filed Mar. 28, 2018, to U.S. Provisional Patent Application No. 62/649,327, titled CLOUD-BASED MEDICAL ANALYTICS FOR SECURITY AND AUTHENTICATION TRENDS AND REACTIVE MEASURES, filed Mar. 28, 2018, to U.S. Provisional Patent Application No. 62/649,315, titled DATA HANDLING AND PRIORITIZATION IN A CLOUD ANALYTICS NETWORK, filed Mar. 28, 2018, to U.S. Provisional Patent Application No. 62/649, 313, titled CLOUD INTERFACE FOR COUPLED SURGICAL DEVICES, filed Mar. 28, 2018, to U.S. Provisional Patent Application No. 62/649,320, titled DRIVE ARRANGEMENTS FOR ROBOT-ASSISTED SURGICAL PLATFORMS, filed Mar. 28, 2018, to U.S. Provisional Patent Application No. 62/649,307, titled AUTOMATIC TOOL ADJUSTMENTS FOR ROBOT-ASSISTED SURGICAL PLATFORMS, filed Mar. 28, 2018, and to U.S. Provisional Patent Application No. 62/649,323, titled SENSING ARRANGEMENTS FOR ROBOT-ASSISTED SURGICAL PLATFORMS, filed Mar. 28, 2018, the disclosure of each of which is herein incorporated by reference in its entirety.

This application also claims the benefit of priority under 35 U.S.C. § 119(e) to U.S. Provisional Patent Application No. 62/611,341, titled INTERACTIVE SURGICAL PLATFORM, filed Dec. 28, 2017, to U.S. Provisional Patent Application No. 62/611,340, titled CLOUD-BASED MEDICAL ANALYTICS, filed Dec. 28, 2017, and to U.S. Provisional Patent Application No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to surgical systems and devices. Clinical information can be collected and/or stored in variety of different surgical devices preoperatively, intraoperatively, and/or postoperatively. Certain information may be helpful to a clinician in making one or more clinical decisions preoperatively, intraoperatively, and/or postoperatively.

SUMMARY

In one aspect the present disclosure provides a computer-implemented method for contextually controlling a surgical device. The method comprising: receiving, by a computer system, perioperative data from the surgical device, the perioperative data associated with a surgical procedure; receiving, by the computer system, images from a scope, the images visualizing the surgical device during the surgical procedure; determining, by the computer system, an attribute of the surgical device from the images; determining, by the computer system, procedural context data based at least on the perioperative data and the attribute of the surgical device; and controlling, by the computer system, the surgical device according to the procedural context data.

In another aspect the present disclosure provides a computer-implemented method for contextually controlling a first surgical device. The method comprising: receiving, by a computer system, perioperative data from a second surgical device, the perioperative data associated with a surgical procedure; receiving, by the computer system, images from a scope, the images visualizing the second surgical device during the surgical procedure; determining, by the computer system, an attribute of the second surgical device from the images; determining, by the computer system, procedural context data based at least on the perioperative data and the attribute of the second surgical device; and controlling, by the computer system, the first surgical device according to the procedural context data.

In another aspect the present disclosure provides a computer-implemented method for contextually controlling a surgical device. The method comprising: receiving, by a computer system, perioperative data from the surgical device, the perioperative data associated with a surgical procedure; receiving, by the computer system, images from a scope, the images visualizing a surgical site during the surgical procedure; determining, by the computer system, an attribute of the surgical site from the images; determining, by the computer system, procedural context data based at least on the perioperative data and the attribute of the surgical site; and controlling, by the computer system, the surgical device according to the procedural context data.

FIGURES

The various aspects described herein, both as to organization and methods of operation, together with further objects and advantages thereof, may best be understood by reference to the following description, taken in conjunction with the accompanying drawings as follows.

Figure 18:
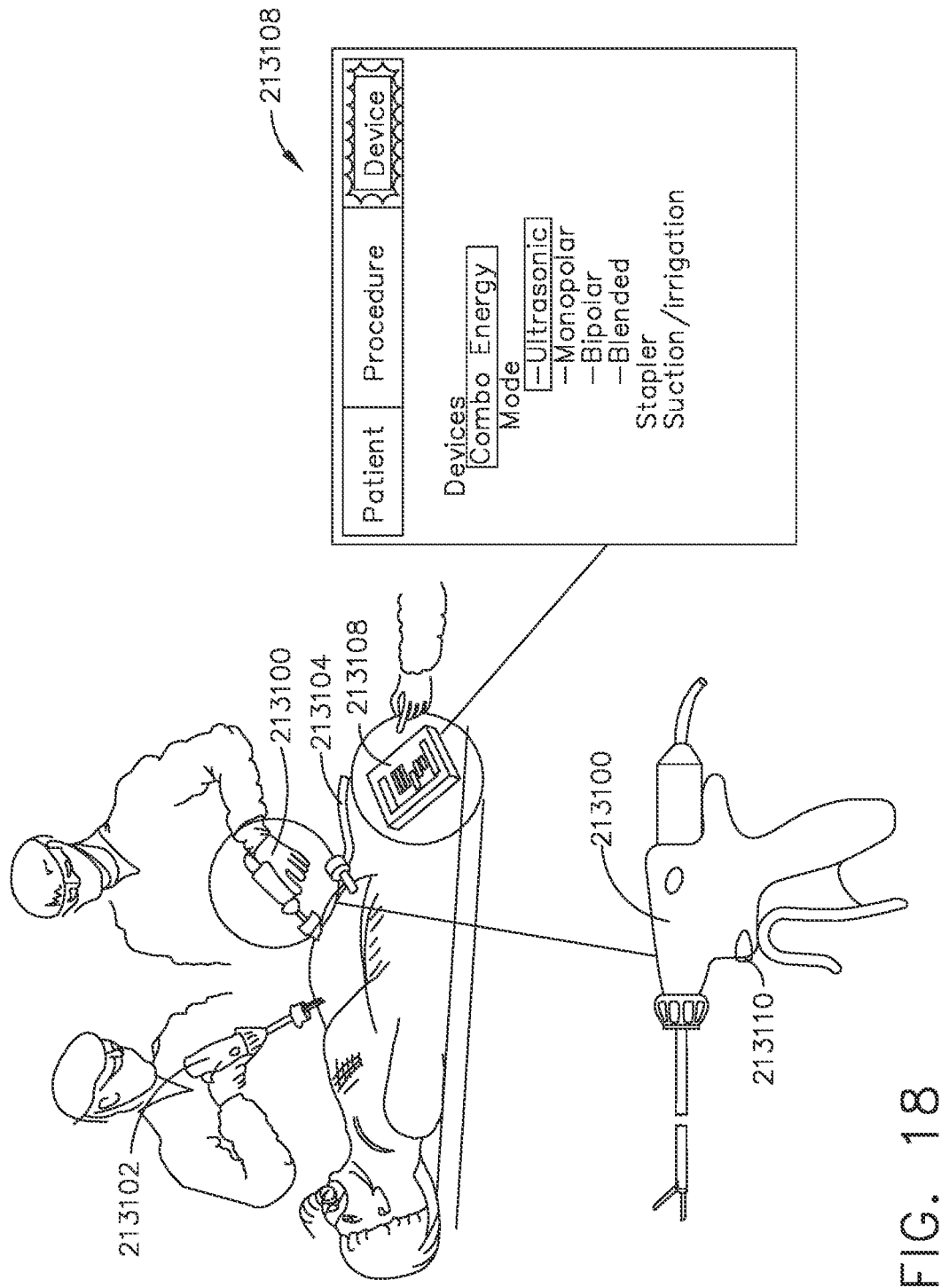

FIG. 18 is a schematic of a surgical procedure involving a plurality of devices in the surgical field, including a combination energy instrument, a surgical stapler, and a suction/irrigation device, and further depicting a detail elevation view of the combination energy instrument and a detail plan view of a sterile field display that includes touch screen controls for adjusting the surgical functions of the plurality of devices in the sterile field, in accordance with at least one aspect of the present disclosure.

Figure 19:
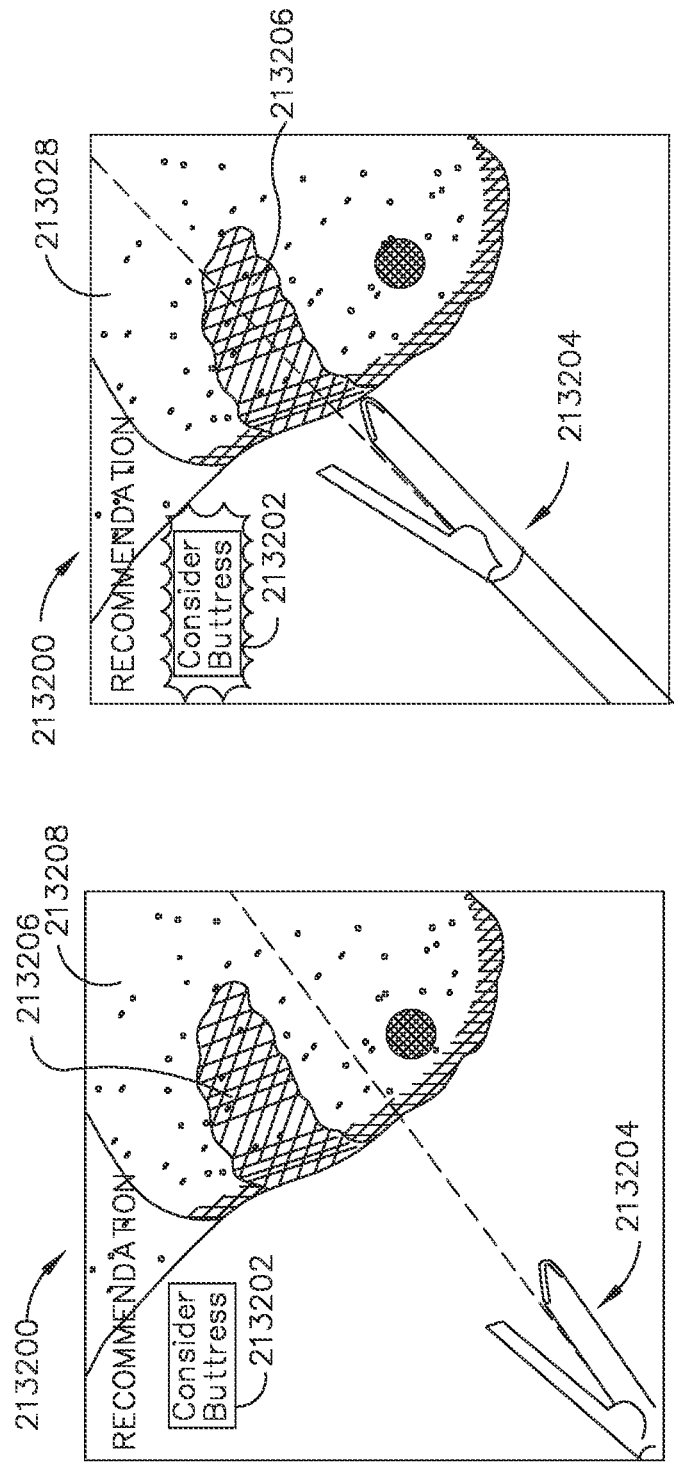

FIG. 19A depicts a display screen including a recommendation for a clinician based on input from a situationally-aware surgical hub, in accordance with at least one aspect of the present disclosure.

FIG. 19B depicts the display screen of FIG. 19A, where the recommendation is indicated with an elevated priority level based on an anticipated surgical act and the input from the situationally-aware surgical hub, in accordance with at least one aspect of the present disclosure.

Figure 20:
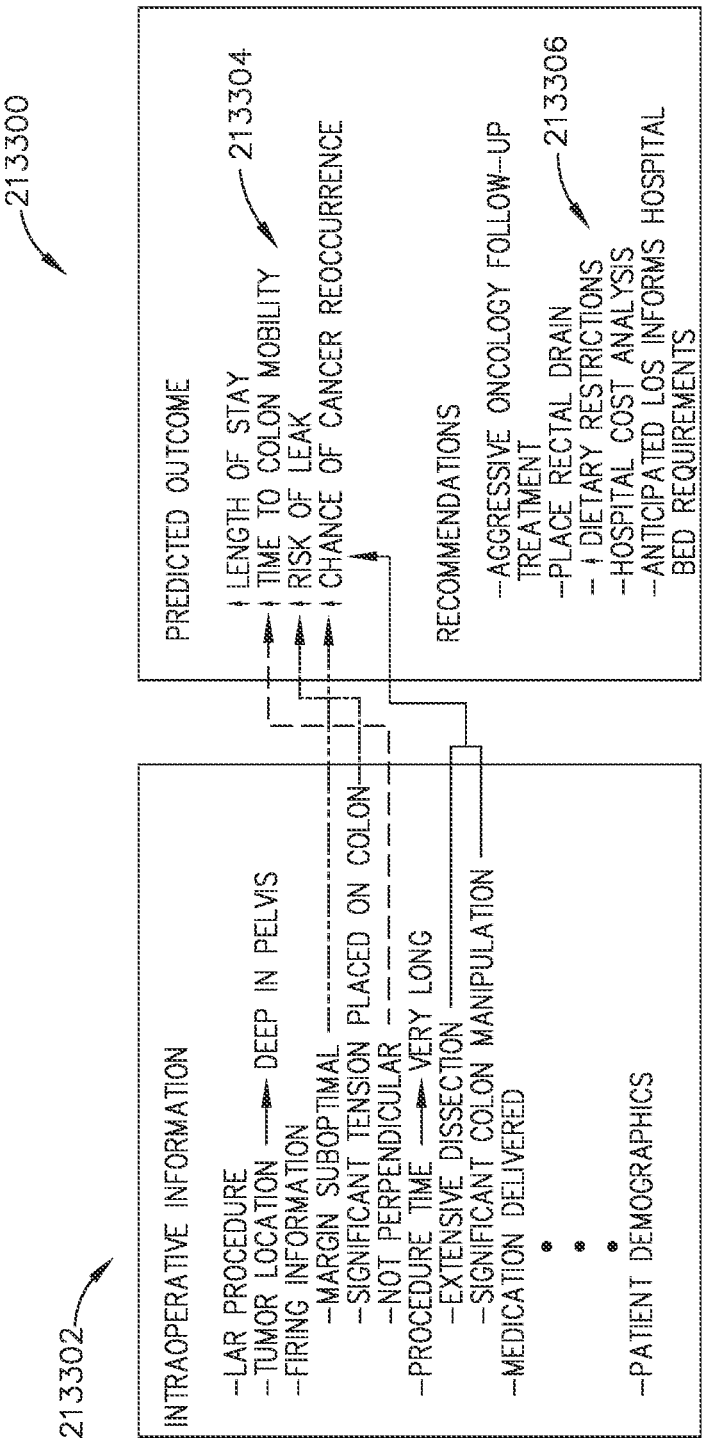

FIG. 20 is a block diagram illustrating intraoperative data correlated with predicted outcomes, and further depicting corresponding recommendations based on the predicted outcomes, in accordance with at least one aspect of the present disclosure.

Figure 21:
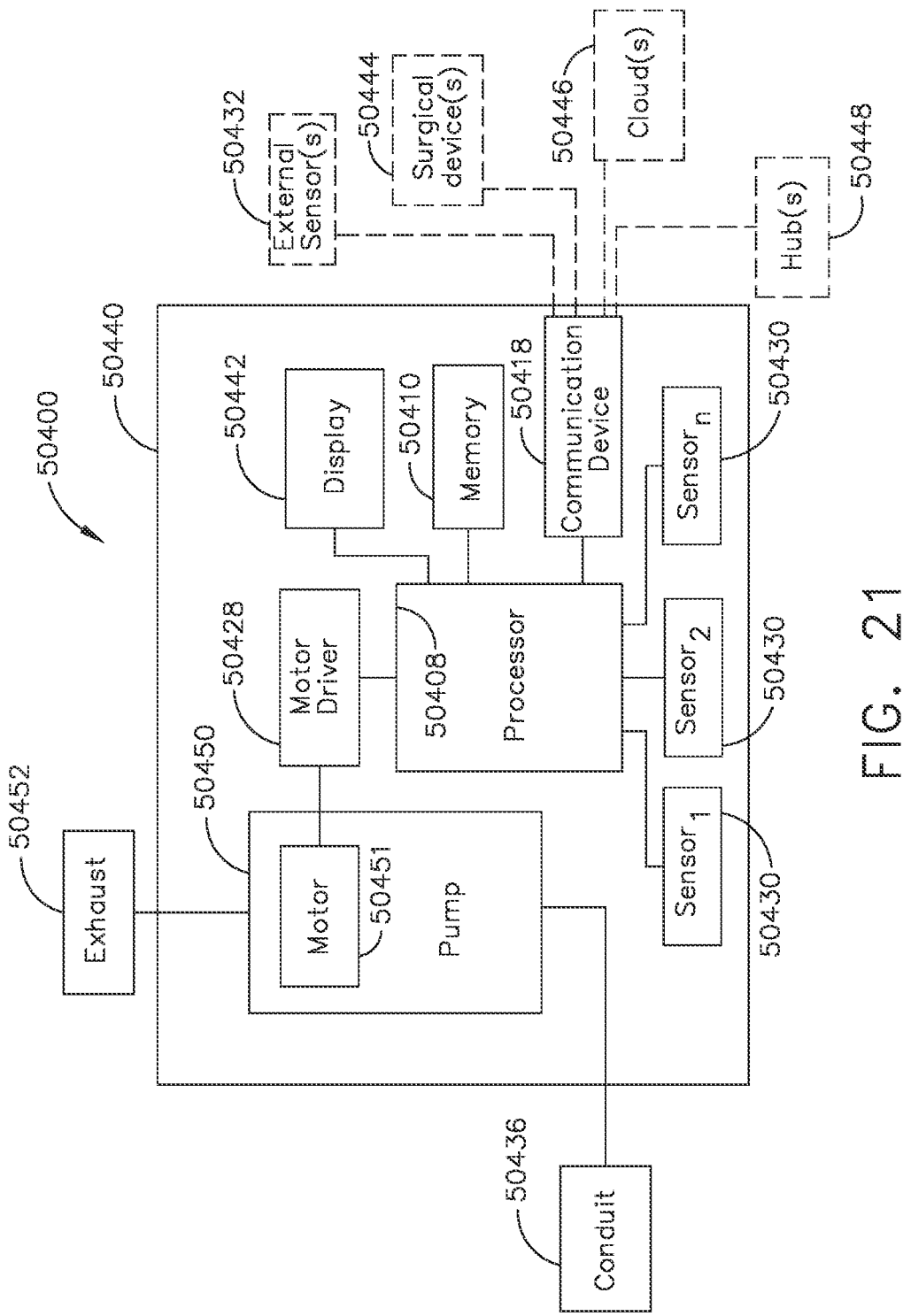

FIG. 21 is a schematic of a surgical evacuation system, in accordance with at least one aspect of the present disclosure.

Figure 22:
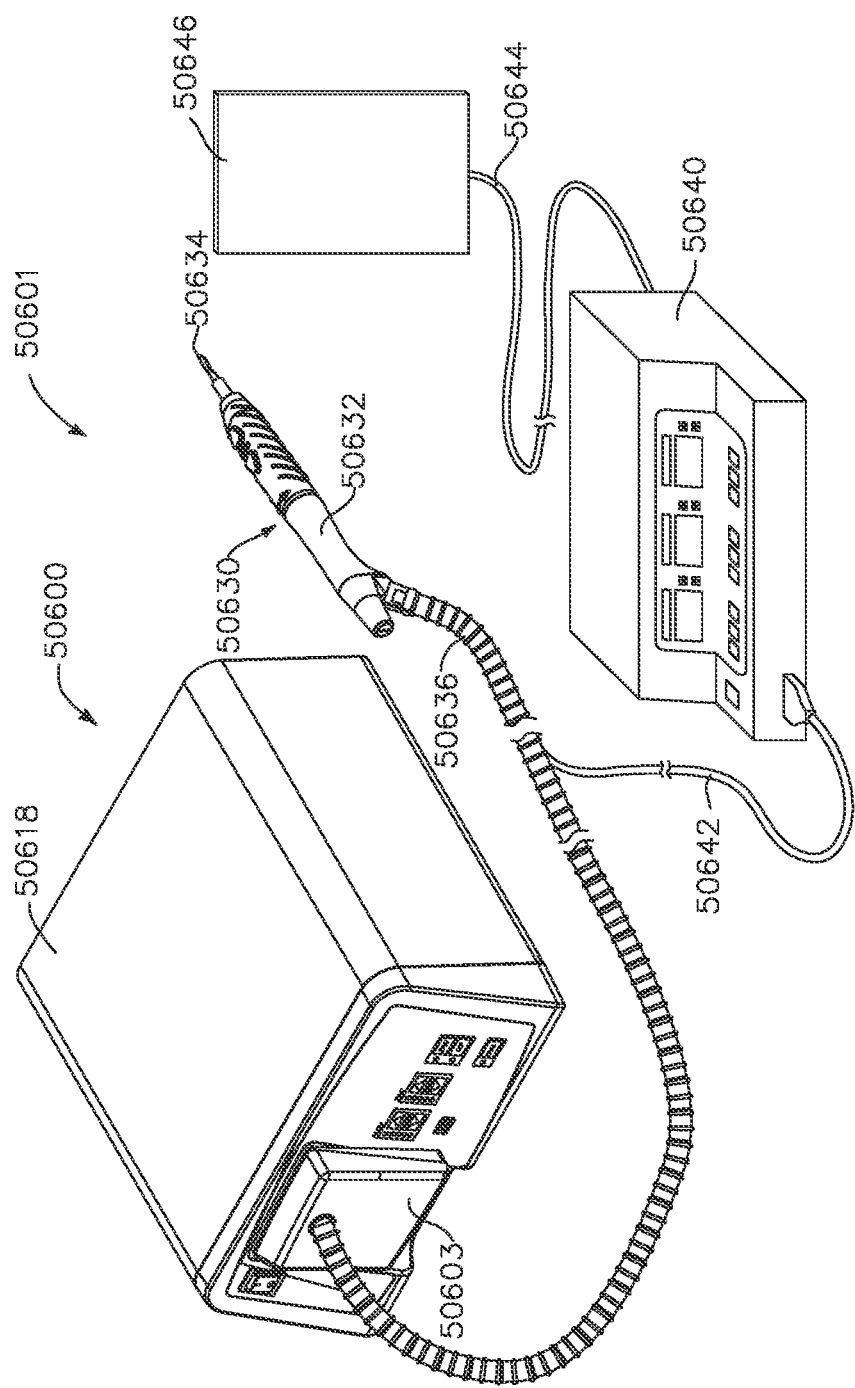

FIG. 22 is a perspective view of a surgical system including a surgical evacuation system, in accordance with at least one aspect of the present disclosure.

Figure 23:
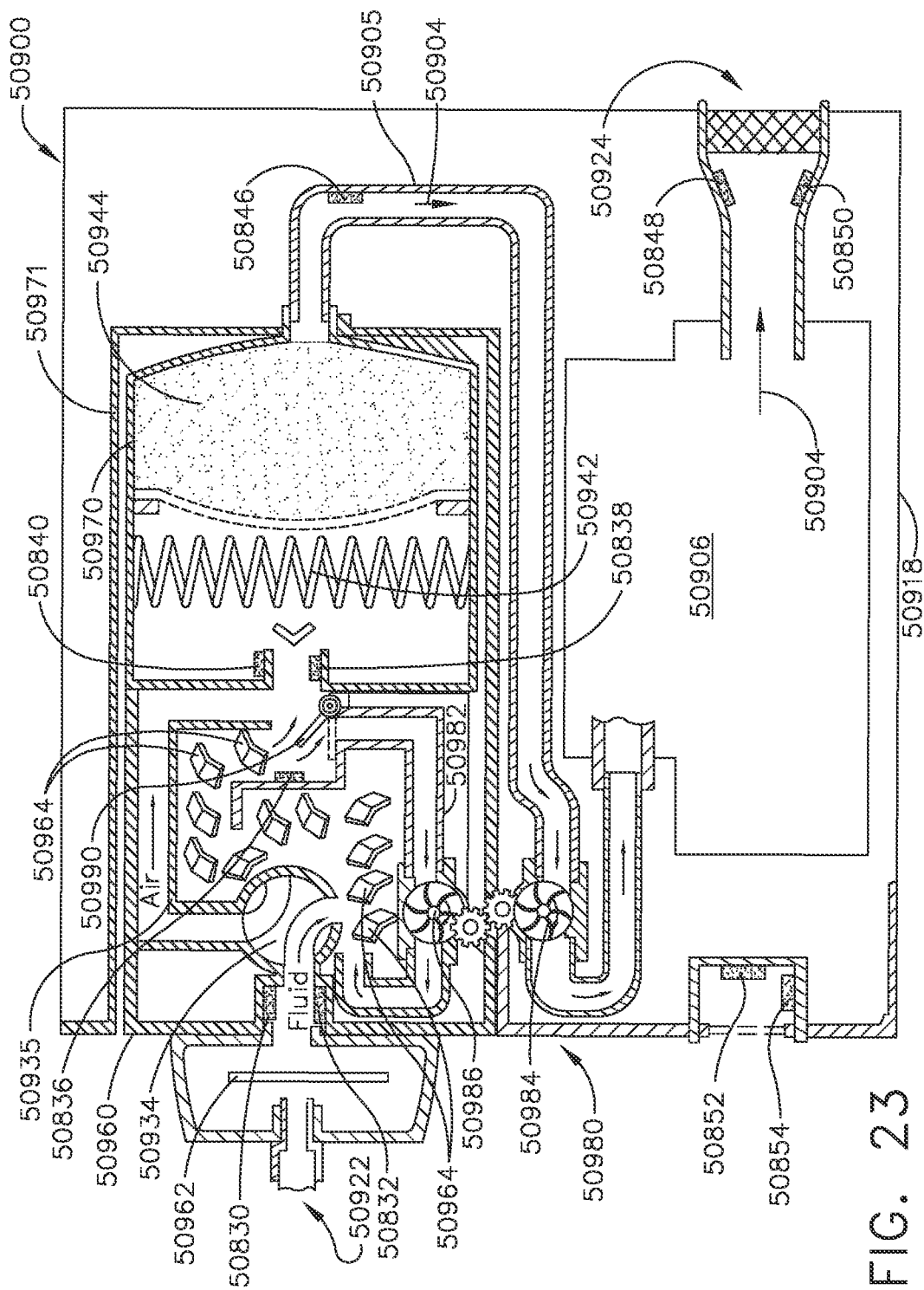

FIG. 23 is a schematic of an evacuator housing of an evacuation system, in accordance with at least one aspect of the present disclosure.

Figure 24:
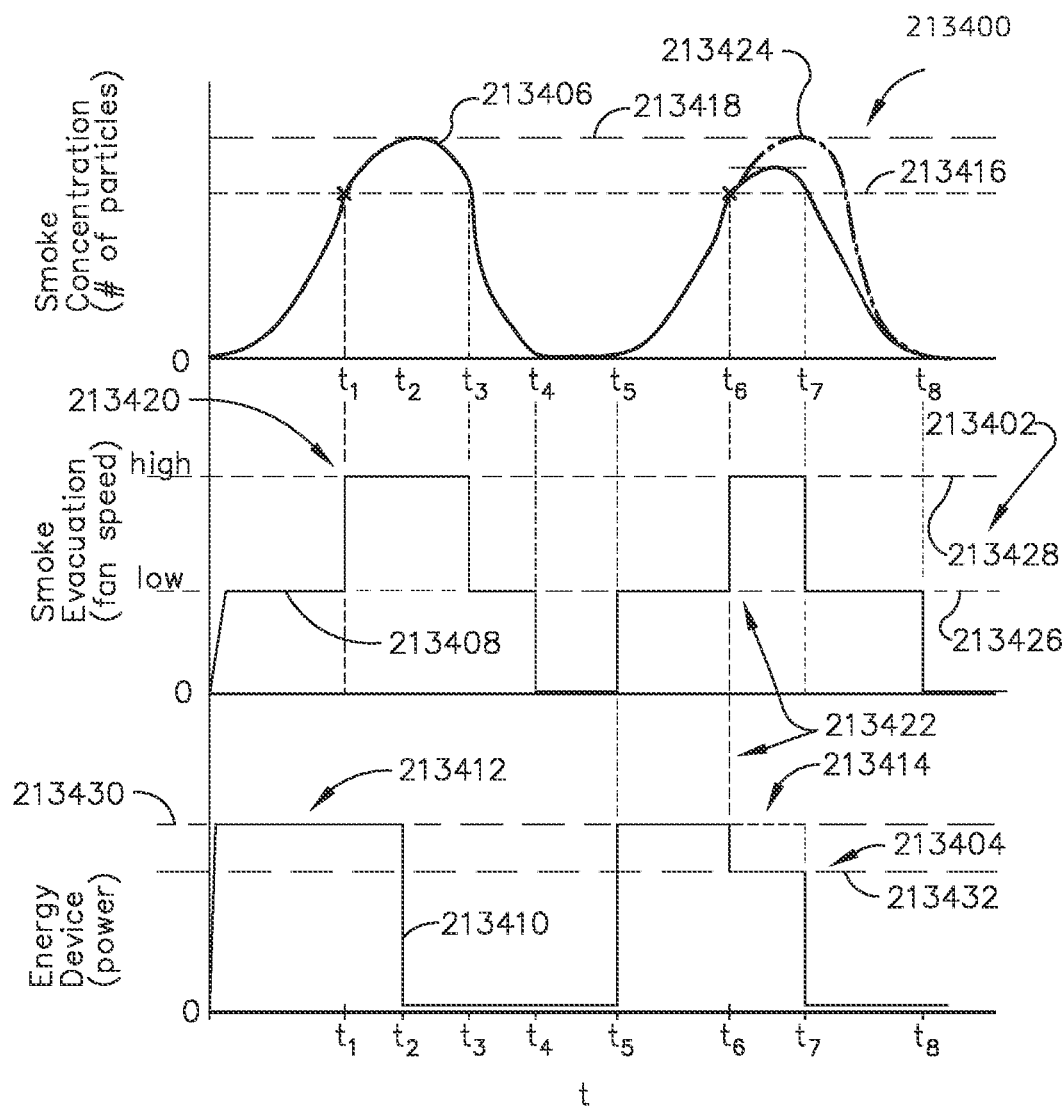

FIG. 24 is a series of graphs depicting particulate concentration, fan speed, and energy device power relative to time, in accordance with at least one aspect of the present disclosure.

Figure 25:
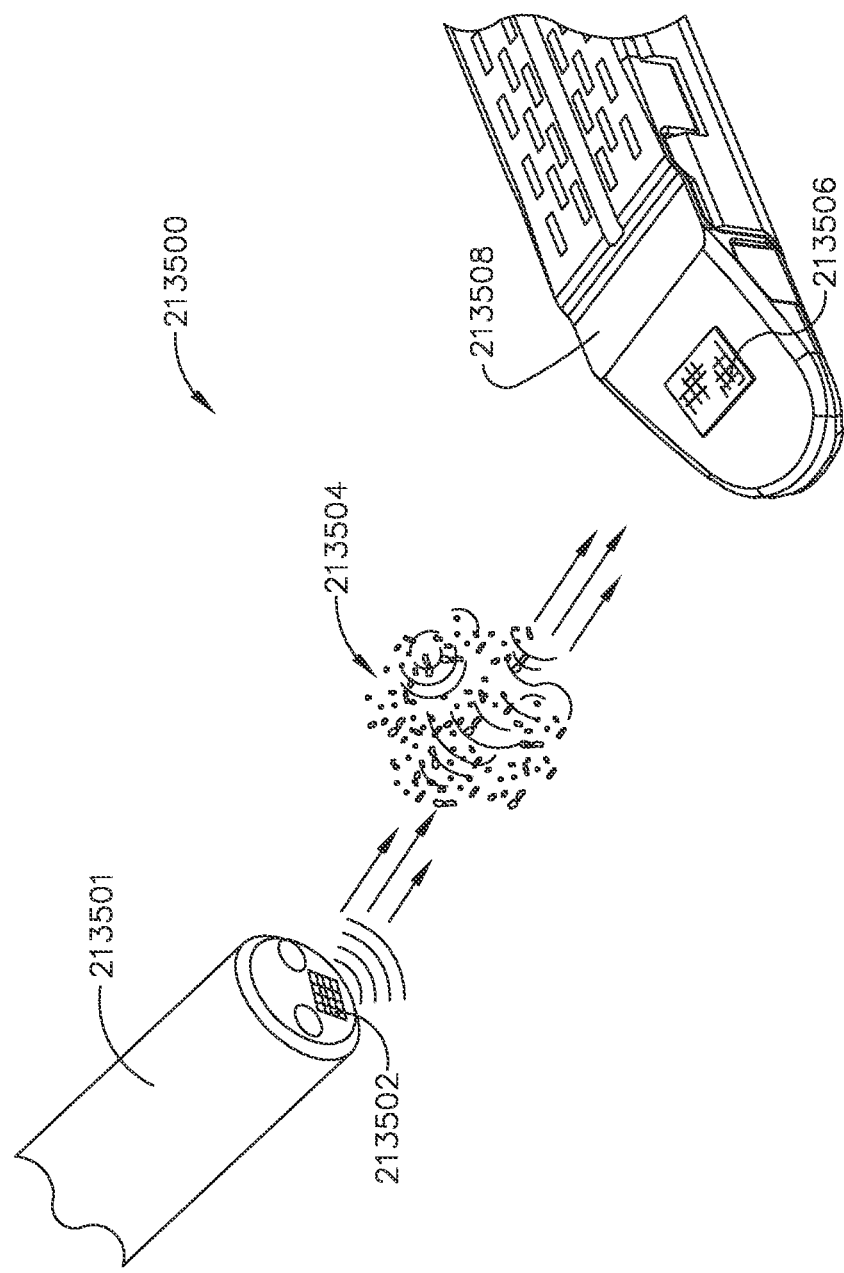

FIG. 25 is an ultrasonic pass-through particle detection system, in accordance with at least one aspect of the present disclosure.

Figures 26, 27:
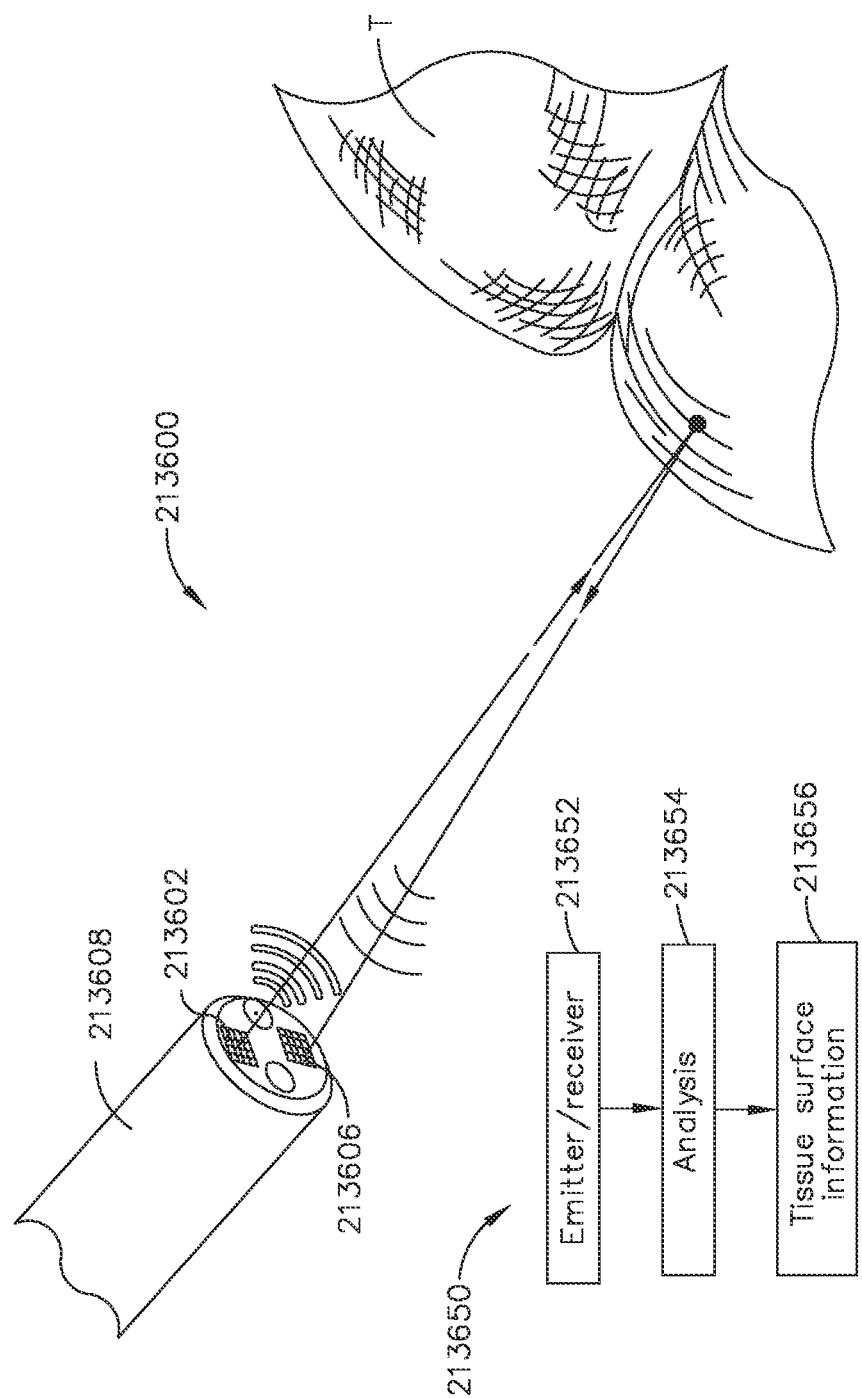

FIG. 26 is an ultrasonic reflection particle detection system, in accordance with at least one aspect of the present disclosure.

FIG. 27 is a flowchart for detecting tissue surface information using the ultrasonic reflection particle detection system of FIG. 26, in accordance with at least one aspect of the present disclosure.

Figure 28:
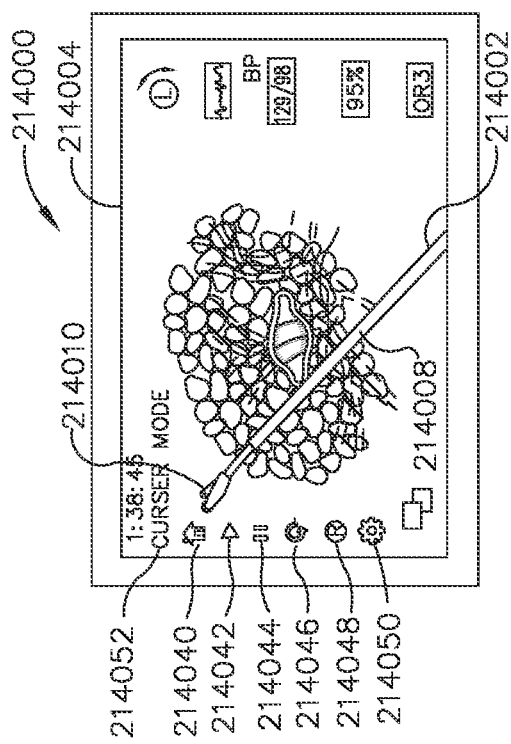
Figure 29:
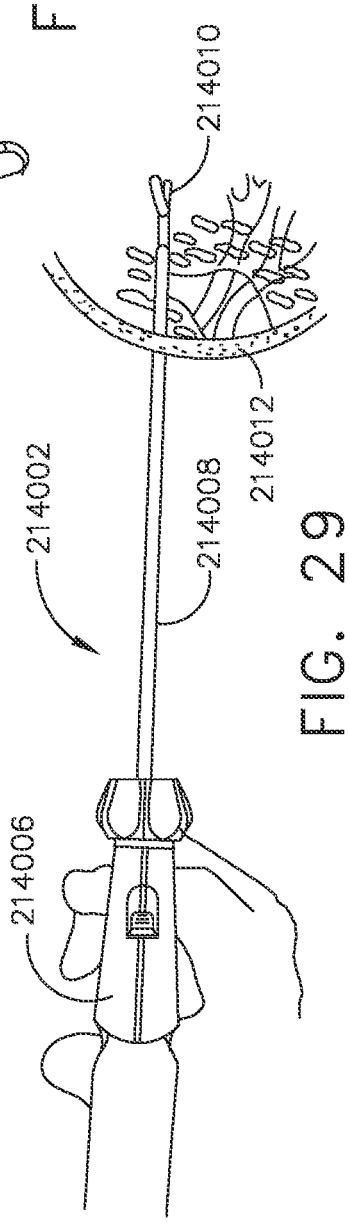

FIG. 28 is a view of a display screen for a surgical procedure, depicting a surgical site and a distal portion of a surgical device at the surgical site, in accordance with at least one aspect of the present disclosure, FIG. 29 is a view of the surgical device of FIG. 28 extending through a surgical barrier into the surgical site, in accordance with at least one aspect of the present disclosure.

Figure 30:
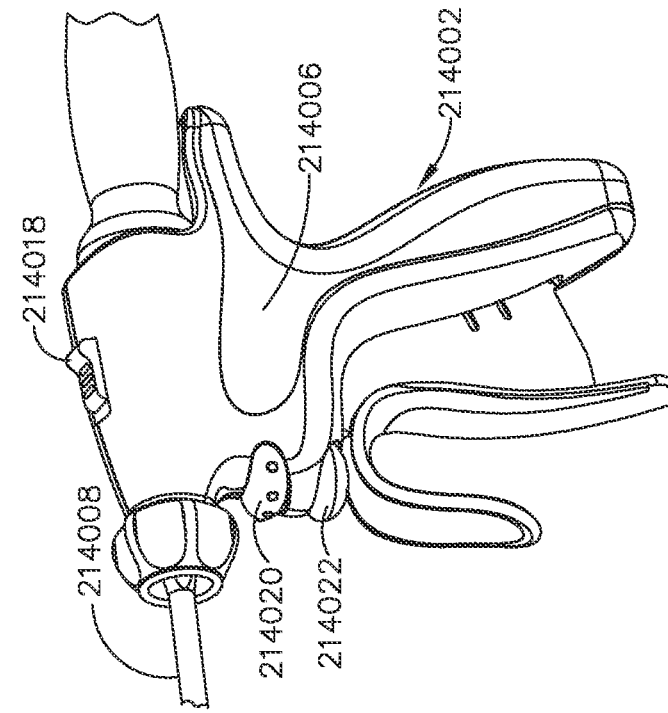

FIG. 30 is a perspective view of a handle portion of the surgical device of FIGS. 28 and 29, the handle portion having an input switch for switching the surgical device between operational modes, in accordance with at least one aspect of the present disclosure.

Figure 31:
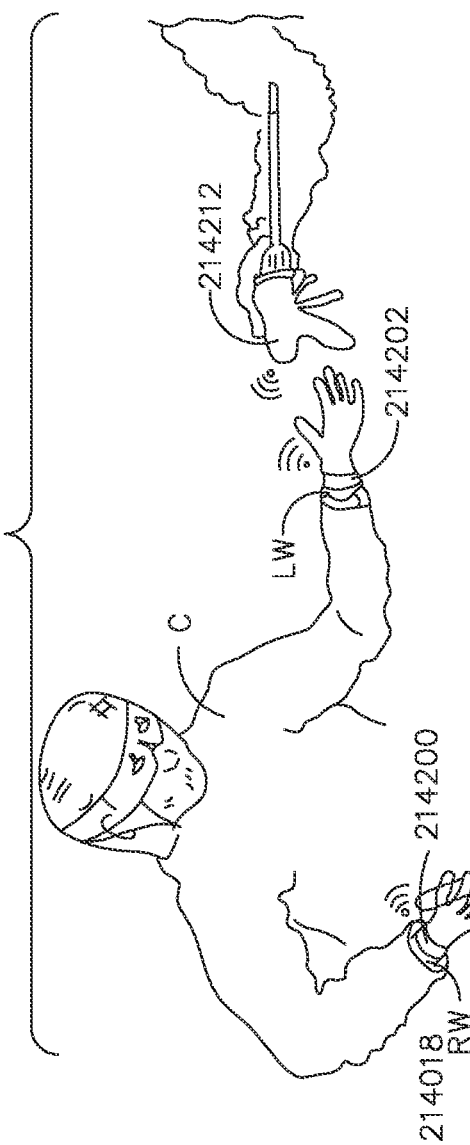

FIG. 31 is a diagram depicting wearable devices communicating with surgical instruments to facilitate pairing and handing off of the surgical instruments, in accordance with at least one aspect of the present disclosure.

Figure 32:
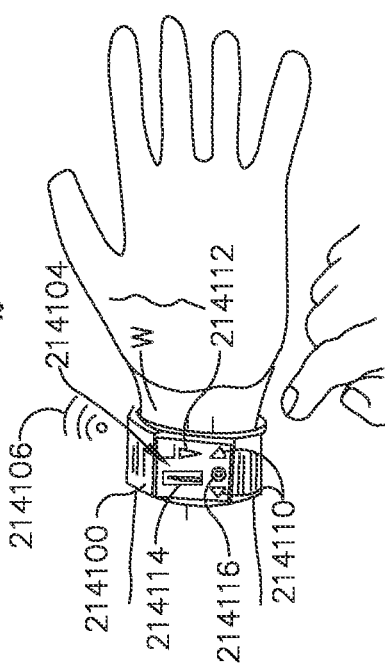

FIG. 32 is a diagram of a wearable wrist device, in accordance with at least one aspect of the present disclosure.

Figure 33:
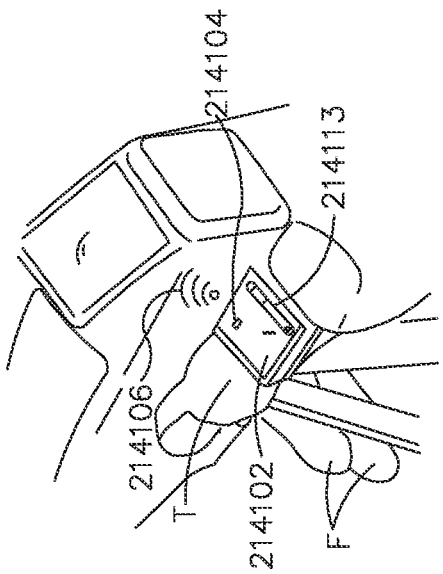

FIG. 33 is a diagram of a wearable ring device, in accordance with at least one aspect of the present disclosure.

FIG. 34A is a first view of a display screen, in which the display screen is configured to receive operator inputs to control a first surgical device—a combination energy device—in accordance with at least one aspect of the present disclosure.

FIG. 34B is a second view of the display screen of FIG. 34A, in which the display screen is configured to receive operator inputs to control a second surgical device—a stapler—in accordance with at least one aspect of the present disclosure.

DESCRIPTION

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY, now U.S. Pat. No. 11,937,769;

U.S. patent application Ser. No. 16/209,395, titled METHOD OF HUB COMMUNICATION, now U.S. Pat. No. 11,659,023;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Pat. No. 11,559,307;

U.S. patent application Ser. No. 16/209,416, titled METHOD OF HUB COMMUNICATION, PROCESSING, DISPLAY, AND CLOUD ANALYTICS, now U.S. Pat. No. 11,576,677;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Pat. No. 11,969,142;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Pat. No. 11,389,164;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Pat. No. 12,096,916;

U.S. patent application Ser. No. 16/209,447, titled METHOD FOR SMOKE EVACUATION FOR SURGICAL HUB, now U.S. Pat. No. 12,127,729;

U.S. patent application Ser. No. 16/209,453, titled METHOD FOR CONTROLLING SMART ENERGY DEVICES, now U.S. Pat. No. 11,589,888;

U.S. patent application Ser. No. 16/209,458, titled METHOD FOR SMART ENERGY DEVICE INFRASTRUCTURE, now U.S. Pat. No. 11,559,308;

U.S. patent application Ser. No. 16/209,465, titled METHOD FOR ADAPTIVE CONTROL SCHEMES FOR SURGICAL NETWORK CONTROL AND INTERACTION, now U.S. Pat. No. 11,304,699;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Pat. No. 11,109,866.

Applicant of the present application owns the following U.S. patent applications, filed on Nov. 6, 2018, the disclosure of each of which is herein incorporated by reference in its entirety:

U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY;

U.S. patent application Ser. No. 16/182,230, titled SURGICAL SYSTEM FOR PRESENTING INFORMATION INTERPRETED FROM EXTERNAL DATA;

U.S. patent application Ser. No. 16/182,233, titled SURGICAL SYSTEMS WITH AUTONOMOUSLY ADJUSTABLE CONTROL PROGRAMS;

U.S. patent application Ser. No. 16/182,239, titled ADJUSTMENT OF DEVICE CONTROL PROGRAMS BASED ON STRATIFIED CONTEXTUAL DATA IN ADDITION TO THE DATA;

U.S. patent application Ser. No. 16/182,243, titled SURGICAL HUB AND MODULAR DEVICE RESPONSE ADJUSTMENT BASED ON SITUATIONAL AWARENESS;

U.S. patent application Ser. No. 16/182,248, titled DETECTION AND ESCALATION OF SECURITY RESPONSES OF SURGICAL INSTRUMENTS TO INCREASING SEVERITY THREATS;

U.S. patent application Ser. No. 16/182,251, titled INTERACTIVE SURGICAL SYSTEM;

U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO THE HUB;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER;

U.S. patent application Ser. No. 16/182,246, titled ADJUSTMENTS BASED ON AIRBORNE PARTICLE PROPERTIES;

U.S. patent application Ser. No. 16/182,256, titled ADJUSTMENT OF A SURGICAL DEVICE FUNCTION BASED ON SITUATIONAL AWARENESS;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;

U.S. patent application Ser. No. 16/182,232, titled CONTROL OF A SURGICAL SYSTEM THROUGH A SURGICAL BARRIER;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES;

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING;

U.S. patent application Ser. No. 16/182,234, titled STAPLING DEVICE WITH BOTH COMPULSORY AND DISCRETIONARY LOCKOUTS BASED ON SENSED PARAMETERS;

U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING;

U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE; and U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION.

Applicant of the present application owns the following U.S. patent applications that were filed on Oct. 26, 2018, the disclosure of each of which is herein incorporated by reference in its entirety:

U.S. patent application Ser. No. 16/172,303, titled METHOD FOR OPERATING A POWERED ARTICULATING MULTI-CLIP APPLIER;

U.S. patent application Ser. No. 16/172,130, titled CLIP APPLIER COMPRISING INTERCHANGEABLE CLIP RELOADS;

U.S. patent application Ser. No. 16/172,066, titled CLIP APPLIER COMPRISING A MOVABLE CLIP MAGAZINE;

U.S. patent application Ser. No. 16/172,078, titled CLIP APPLIER COMPRISING A ROTATABLE CLIP MAGAZINE;

U.S. patent application Ser. No. 16/172,087, titled CLIP APPLIER COMPRISING CLIP ADVANCING SYSTEMS;

U.S. patent application Ser. No. 16/172,094, titled CLIP APPLIER COMPRISING A CLIP CRIMPING SYSTEM;

U.S. patent application Ser. No. 16/172,128, titled CLIP APPLIER COMPRISING A RECIPROCATING CLIP ADVANCING MEMBER;

U.S. patent application Ser. No. 16/172,168, titled CLIP APPLIER COMPRISING A MOTOR CONTROLLER;

U.S. patent application Ser. No. 16/172,164, titled SURGICAL SYSTEM COMPRISING A SURGICAL TOOL AND A SURGICAL HUB;

U.S. patent application Ser. No. 16/172,328, titled METHOD OF HUB COMMUNICATION WITH SURGICAL INSTRUMENT SYSTEMS;

U.S. patent application Ser. No. 16/172,280, titled METHOD FOR PRODUCING A SURGICAL INSTRUMENT COMPRISING A SMART ELECTRICAL SYSTEM;

U.S. patent application Ser. No. 16/172,219, titled METHOD OF HUB COMMUNICATION WITH SURGICAL INSTRUMENT SYSTEMS;

U.S. patent application Ser. No. 16/172,248, titled METHOD OF HUB COMMUNICATION WITH SURGICAL INSTRUMENT SYSTEMS;

U.S. patent application Ser. No. 16/172,198, titled METHOD OF HUB COMMUNICATION WITH SURGICAL INSTRUMENT SYSTEMS; and U.S. patent application Ser. No. 16/172,155, titled METHOD OF HUB COMMUNICATION WITH SURGICAL INSTRUMENT SYSTEMS.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR EMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. patent applications, filed on Aug. 24, 2018, the disclosure of each of which is herein incorporated by reference in its entirety:

U.S. patent application Ser. No. 16/112,129, titled SURGICAL SUTURING INSTRUMENT CONFIGURED TO MANIPULATE TISSUE USING MECHANICAL AND ELECTRICAL POWER;

U.S. patent application Ser. No. 16/112,155, titled SURGICAL SUTURING INSTRUMENT COMPRISING A CAPTURE WIDTH WHICH IS LARGER THAN TROCAR DIAMETER;

U.S. patent application Ser. No. 16/112,168, titled SURGICAL SUTURING INSTRUMENT COMPRISING A NON-CIRCULAR NEEDLE;

U.S. patent application Ser. No. 16/112,180, titled ELECTRICAL POWER OUTPUT CONTROL BASED ON MECHANICAL FORCES;

U.S. patent application Ser. No. 16/112,193, titled REACTIVE ALGORITHM FOR SURGICAL SYSTEM;

U.S. patent application Ser. No. 16/112,099, titled SURGICAL INSTRUMENT COMPRISING AN ADAPTIVE ELECTRICAL SYSTEM;

U.S. patent application Ser. No. 16/112,112, titled CONTROL SYSTEM ARRANGEMENTS FOR A MODULAR SURGICAL INSTRUMENT;

U.S. patent application Ser. No. 16/112,119, titled ADAPTIVE CONTROL PROGRAMS FOR A SURGICAL SYSTEM COMPRISING MORE THAN ONE TYPE OF CARTRIDGE;

U.S. patent application Ser. No. 16/112,097, titled SURGICAL INSTRUMENT SYSTEMS COMPRISING BATTERY ARRANGEMENTS;

U.S. patent application Ser. No. 16/112,109, titled SURGICAL INSTRUMENT SYSTEMS COMPRISING HANDLE ARRANGEMENTS;

U.S. patent application Ser. No. 16/112,114, titled SURGICAL INSTRUMENT SYSTEMS COMPRISING FEEDBACK MECHANISMS;

U.S. patent application Ser. No. 16/112,117, titled SURGICAL INSTRUMENT SYSTEMS COMPRISING LOCKOUT MECHANISMS;

U.S. patent application Ser. No. 16/112,095, titled SURGICAL INSTRUMENTS COMPRISING A LOCKABLE END EFFECTOR SOCKET;

U.S. patent application Ser. No. 16/112,121, titled SURGICAL INSTRUMENTS COMPRISING A SHIFTING MECHANISM;

U.S. patent application Ser. No. 16/112,151, titled SURGICAL INSTRUMENTS COMPRISING A SYSTEM FOR ARTICULATION AND ROTATION COMPENSATION;

U.S. patent application Ser. No. 16/112,154, titled SURGICAL INSTRUMENTS COMPRISING A BIASED SHIFTING MECHANISM;

U.S. patent application Ser. No. 16/112,226, titled SURGICAL INSTRUMENTS COMPRISING AN ARTICULATION DRIVE THAT PROVIDES FOR HIGH ARTICULATION ANGLES;

U.S. patent application Ser. No. 16/112,062, titled SURGICAL DISSECTORS AND MANUFACTURING TECHNIQUES;

U.S. patent application Ser. No. 16/112,098, titled SURGICAL DISSECTORS CONFIGURED TO APPLY MECHANICAL AND ELECTRICAL ENERGY;

U.S. patent application Ser. No. 16/112,237, titled SURGICAL CLIP APPLIER CONFIGURED TO STORE CLIPS IN A STORED STATE;

U.S. patent application Ser. No. 16/112,245, titled SURGICAL CLIP APPLIER COMPRISING AN EMPTY CLIP CARTRIDGE LOCKOUT;

U.S. patent application Ser. No. 16/112,249, titled SURGICAL CLIP APPLIER COMPRISING AN AUTOMATIC CLIP FEEDING SYSTEM;

U.S. patent application Ser. No. 16/112,253, titled SURGICAL CLIP APPLIER COMPRISING ADAPTIVE FIRING CONTROL; and U.S. patent application Ser. No. 16/112,257, titled SURGICAL CLIP APPLIER COMPRISING ADAPTIVE CONTROL IN RESPONSE TO A STRAIN GAUGE CIRCUIT.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DETECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. patent applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;

U.S. patent application Ser. No. 15/940,632, titled DATA STRIPPING METHOD TO INTERROGATE PATIENT RECORDS AND CREATE ANONYMIZED RECORD;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, titled SELF DESCRIBING DATA PACKETS GENERATED AT AN ISSUING INSTRUMENT;

U.S. patent application Ser. No. 15/940,649, titled DATA PAIRING TO INTERCONNECT A DEVICE MEASURED PARAMETER WITH AN OUTCOME;

U.S. patent application Ser. No. 15/940,654, titled SURGICAL HUB SITUATIONAL AWARENESS;

U.S. patent application Ser. No. 15/940,663, titled SURGICAL SYSTEM DISTRIBUTED PROCESSING;

U.S. patent application Ser. No. 15/940,668, titled AGGREGATION AND REPORTING OF SURGICAL HUB DATA;

U.S. patent application Ser. No. 15/940,671, titled SURGICAL HUB SPATIAL AWARENESS TO DETERMINE DEVICES IN OPERATING THEATER;

U.S. patent application Ser. No. 15/940,686, titled DISPLAY OF ALIGNMENT OF STAPLE CARTRIDGE TO PRIOR LINEAR STAPLE LINE;

U.S. patent application Ser. No. 15/940,700, titled STERILE FIELD INTERACTIVE CONTROL DISPLAYS;

U.S. patent application Ser. No. 15/940,629, titled COMPUTER IMPLEMENTED INTERACTIVE SURGICAL SYSTEMS;

U.S. patent application Ser. No. 15/940,704, titled USE OF LASER LIGHT AND RED-GREEN-BLUE COLORATION TO DETERMINE PROPERTIES OF BACK SCATTERED LIGHT;

U.S. patent application Ser. No. 15/940,722, titled CHARACTERIZATION OF TISSUE IRREGULARITIES THROUGH THE USE OF MONO-CHROMATIC LIGHT REFRACTIVITY;

U.S. patent application Ser. No. 15/940,742, titled DUAL CMOS ARRAY IMAGING;

U.S. patent application Ser. No. 15/940,636, titled ADAPTIVE CONTROL PROGRAM UPDATES FOR SURGICAL DEVICES;

U.S. patent application Ser. No. 15/940,653, titled ADAPTIVE CONTROL PROGRAM UPDATES FOR SURGICAL HUBS;

U.S. patent application Ser. No. 15/940,660, titled CLOUD-BASED MEDICAL ANALYTICS FOR CUSTOMIZATION AND RECOMMENDATIONS TO A USER;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, titled CLOUD-BASED MEDICAL ANALYTICS FOR SECURITY AND AUTHENTICATION TRENDS AND REACTIVE MEASURES;

U.S. patent application Ser. No. 15/940,706, titled DATA HANDLING AND PRIORITIZATION IN A CLOUD ANALYTICS NETWORK;

U.S. patent application Ser. No. 15/940,675, titled CLOUD INTERFACE FOR COUPLED SURGICAL DEVICES;

U.S. patent application Ser. No. 15/940,627, titled DRIVE ARRANGEMENTS FOR ROBOT-ASSISTED SURGICAL PLATFORMS;

U.S. patent application Ser. No. 15/940,637, titled COMMUNICATION ARRANGEMENTS FOR ROBOT-ASSISTED SURGICAL PLATFORMS;

U.S. patent application Ser. No. 15/940,642, titled CONTROLS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,680, titled CONTROLLERS FOR ROBOT-ASSISTED SURGICAL PLATFORMS;

U.S. patent application Ser. No. 15/940,683, titled COOPERATIVE SURGICAL ACTIONS FOR ROBOT-ASSISTED SURGICAL PLATFORMS;

U.S. patent application Ser. No. 15/940,690, titled DISPLAY ARRANGEMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Applicant of the present application owns the following U.S. Provisional patent applications, filed on Mar. 8, 2018, the disclosure of each of which is herein incorporated by reference in its entirety:

U.S. Provisional Patent Application No. 62/640,417, titled TEMPERATURE CONTROL IN ULTRASONIC DEVICE AND CONTROL SYSTEM THEREFOR; and U.S. Provisional Patent Application No. 62/640,415, titled ESTIMATING STATE OF ULTRASONIC END EFFECTOR AND CONTROL SYSTEM THEREFOR.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Surgical Hubs

Figure 1:
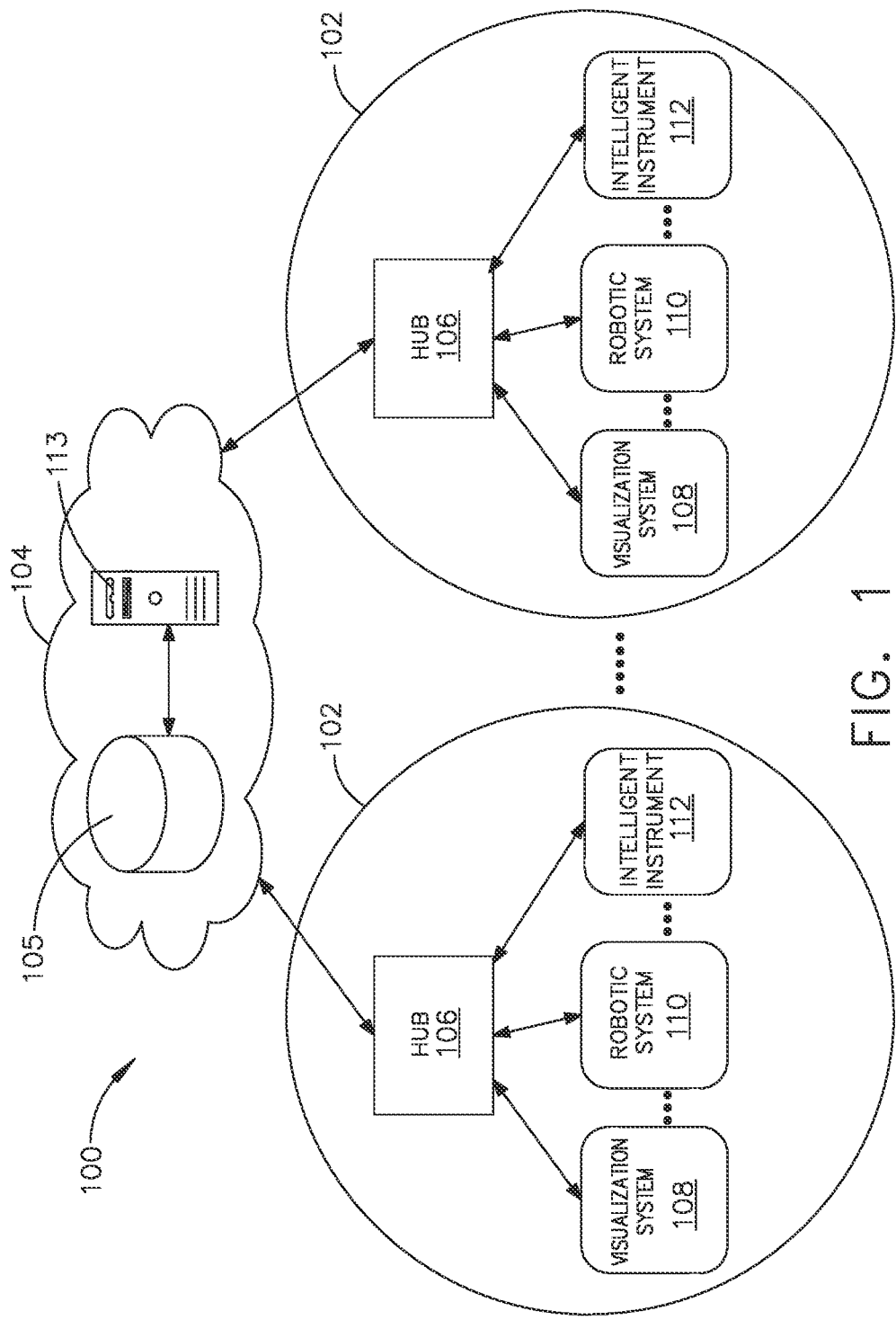
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

In various aspects, the intelligent instruments 112 as described herein with reference to FIGS. 1-7 may be implemented as an energy device 213000 (FIG. 16), a combination energy instrument 213100 (FIG. 18), a surgical stapler 213102 (FIG. 18), a suction/irrigation device 213104 (FIG. 18), a sterile field display 213108 (FIG. 18), a surgical device 213204 (FIGS. 19A and 19B), a surgical evacuation system 50400 (FIG. 21), an electrosurgical instrument 50630 (FIG. 22), an evacuation system 50600 (FIG. 22), an evacuation system 50900 (FIG. 23), a scope 213501 (FIG. 25), and a surgical device 213608 (FIG. 26), for example. In such instances, the intelligent instruments 112 (e.g., devices $1_a$-$1_n$), such as the combination energy instrument 213100 (FIG. 18), the surgical stapler 213102 (FIG. 18), the suction/ irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26), are configured to operate in a surgical data network 201 as described with reference to FIG. 8.

Figure 2:
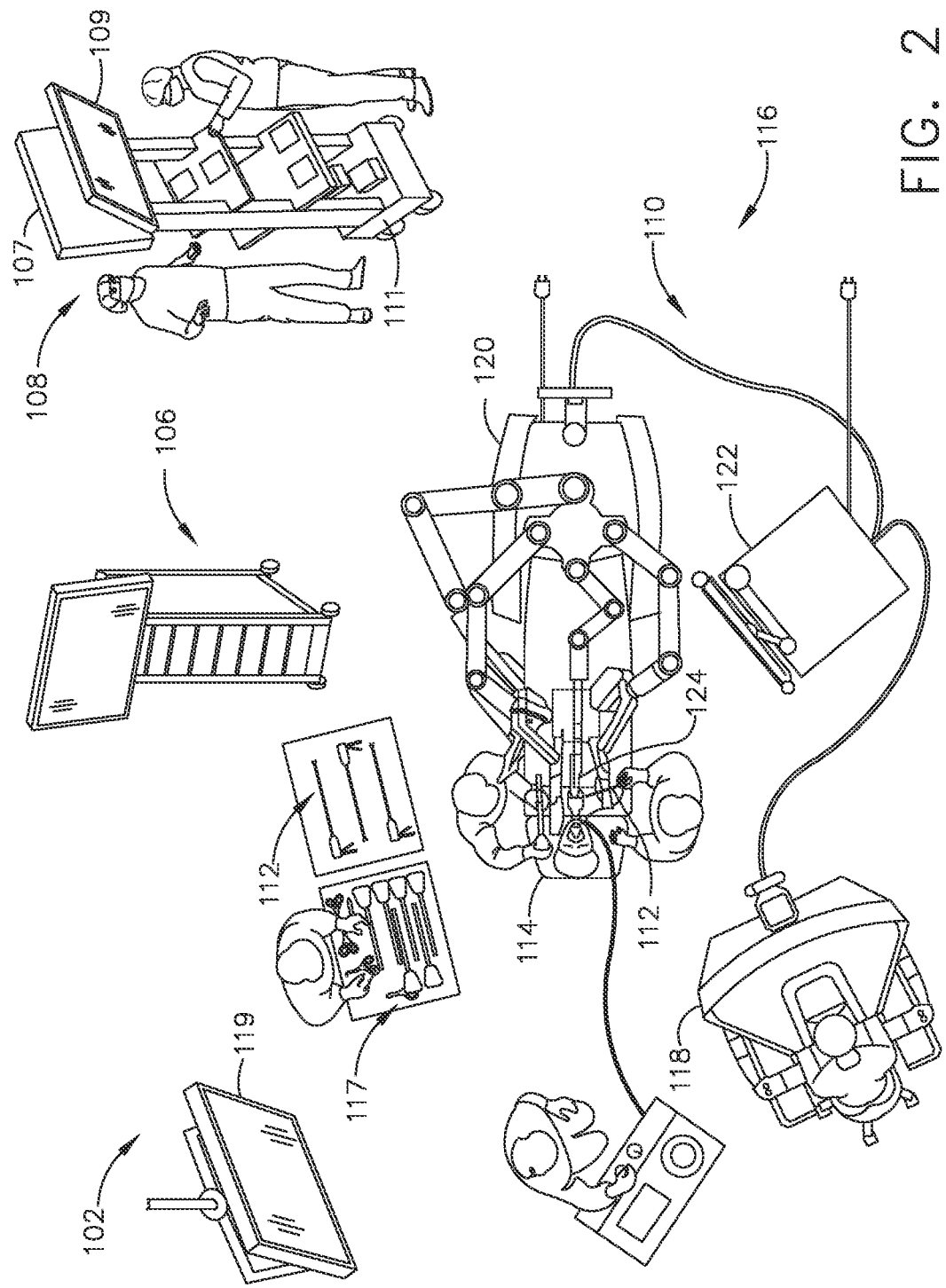
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
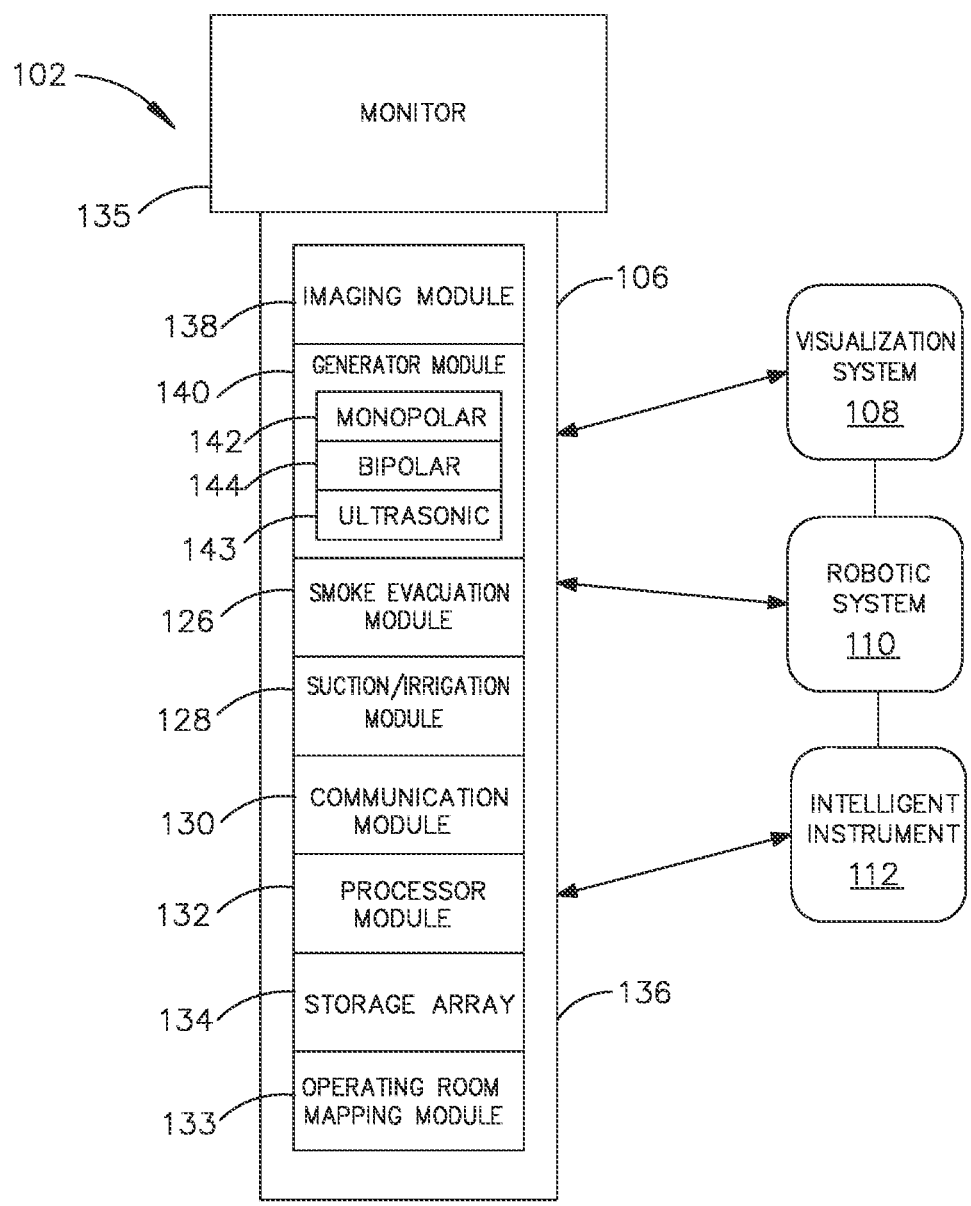
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140 (which can include a monopolar generator 142, a bipolar generator 144, and/or an ultrasonic generator 143), a communication module 130, a processor module 132, and a storage array 134. In certain aspects, as illustrated in FIG. 3, the hub 106 further includes a smoke evacuation module 126, a suction/irrigation module 128, and/or an OR mapping module 133.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
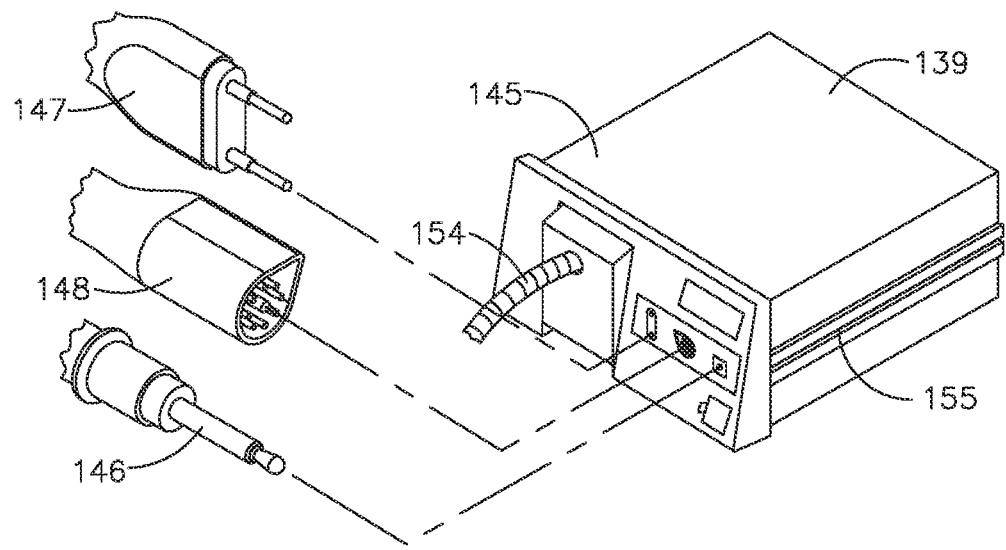
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
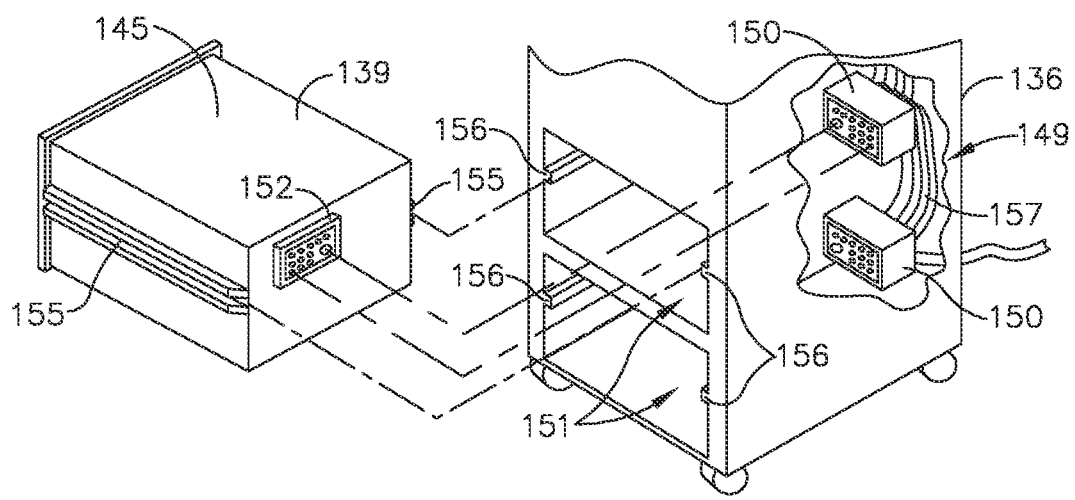
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
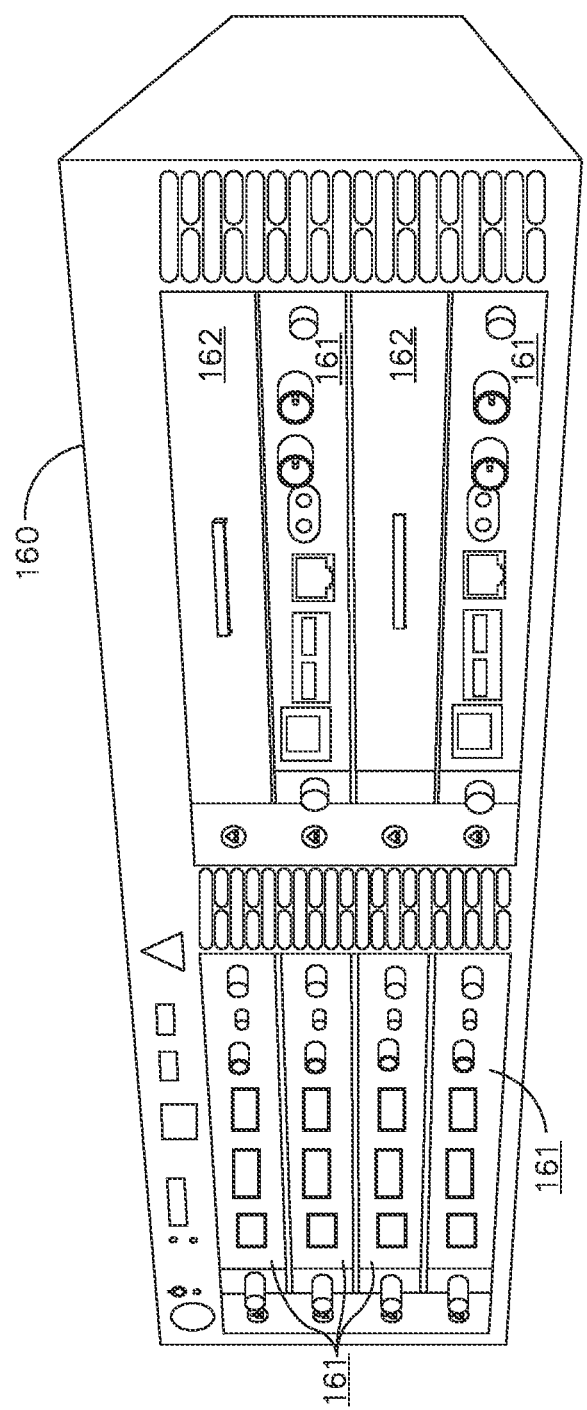
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
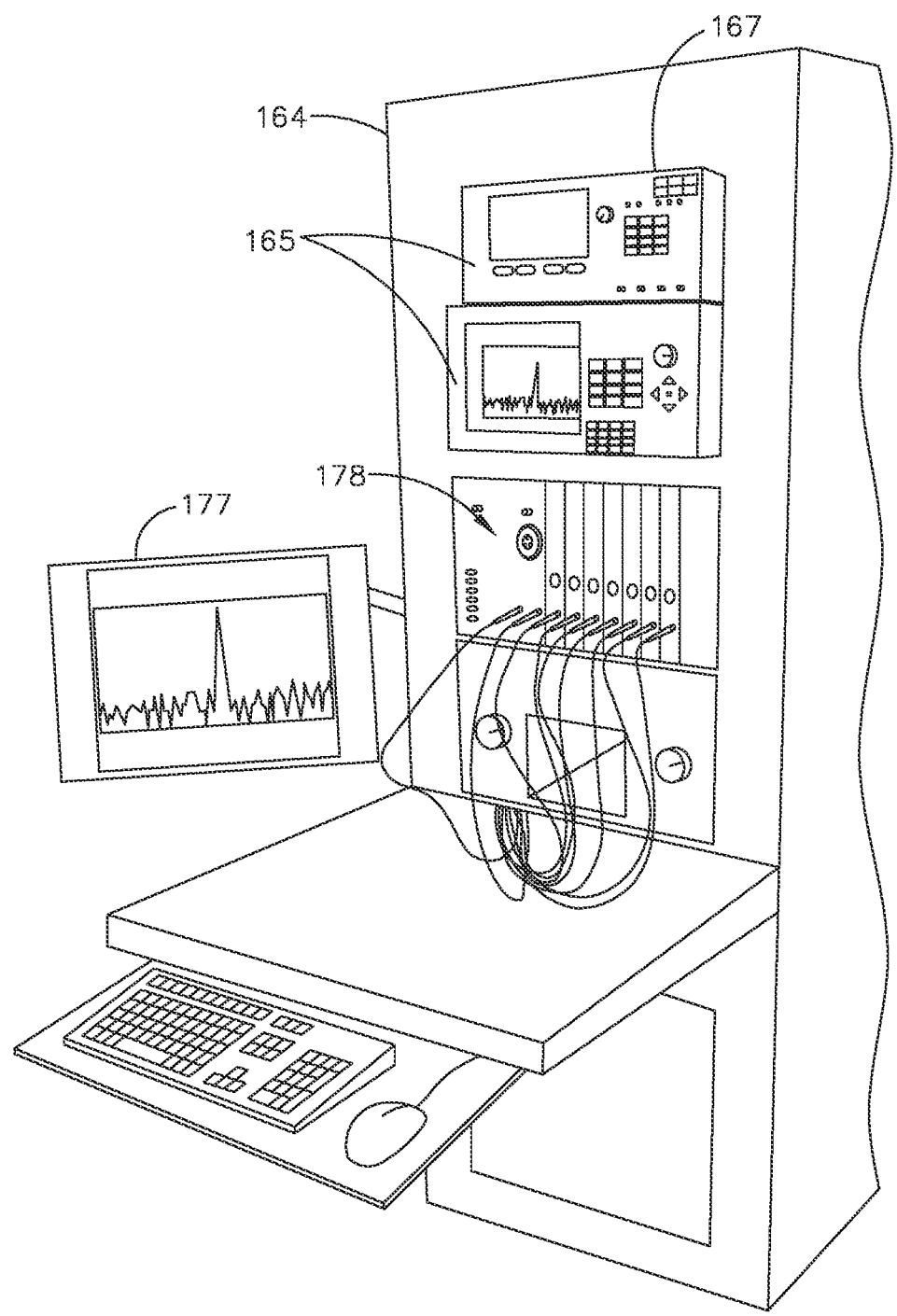
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
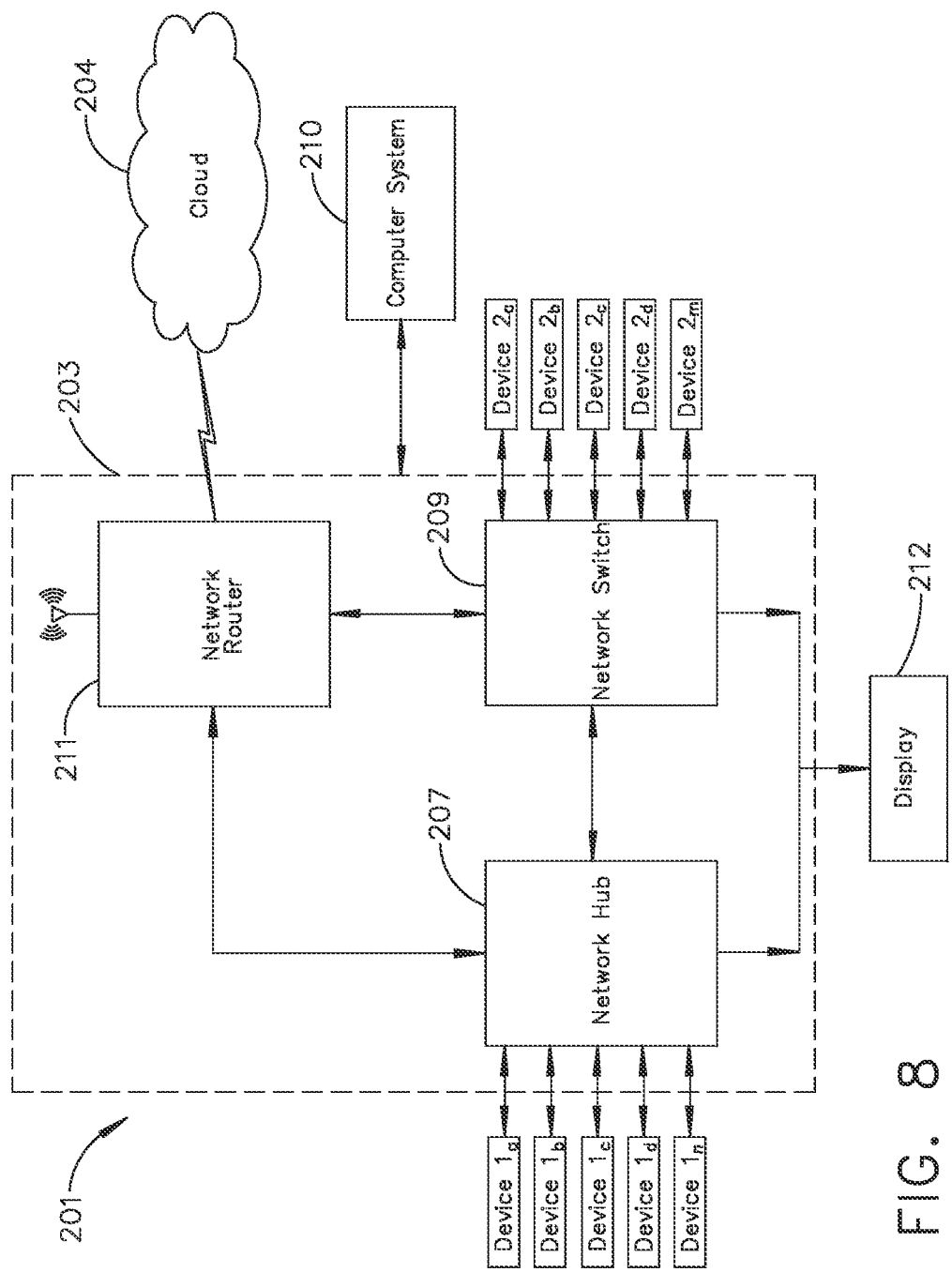
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
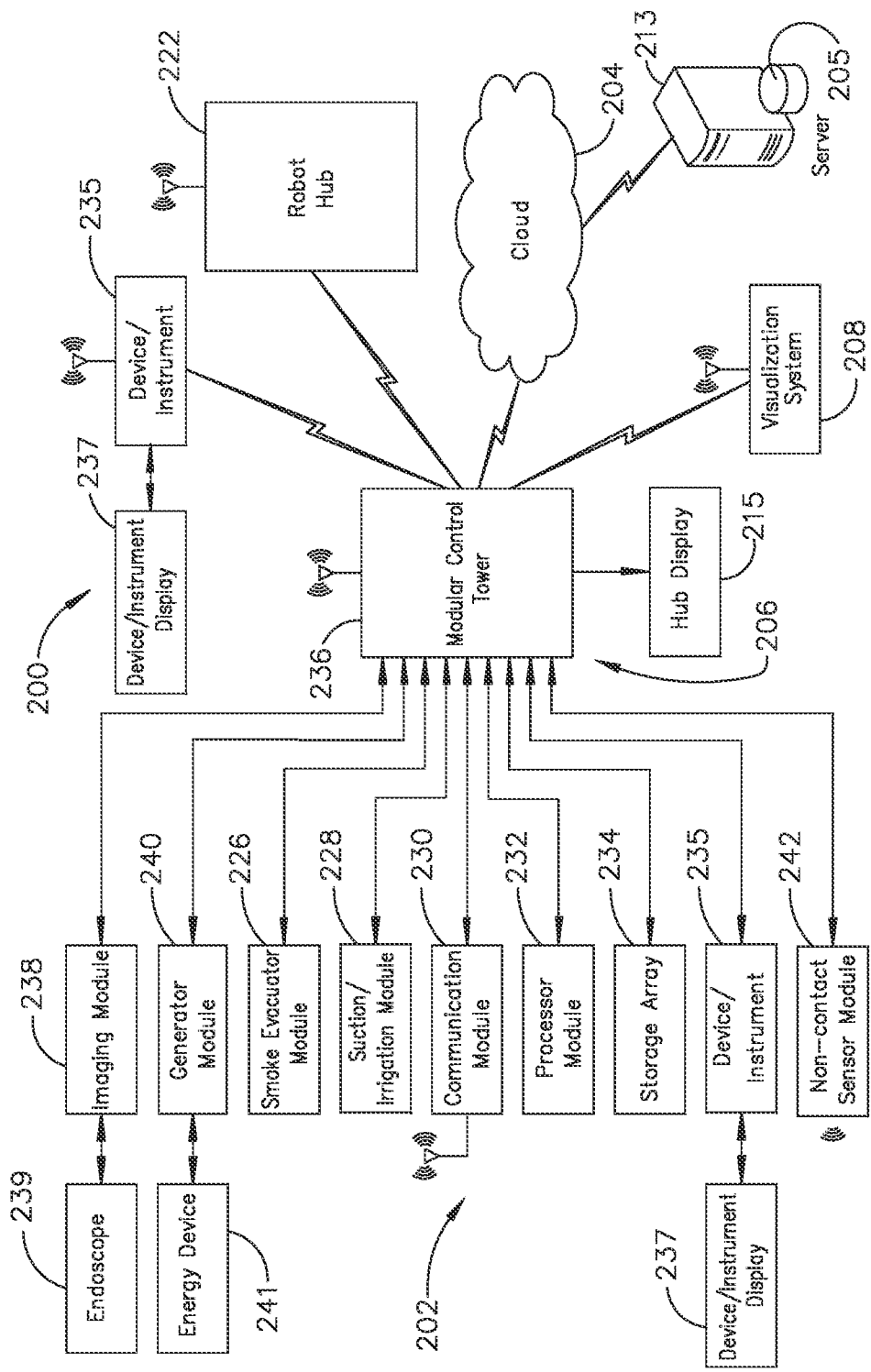
FIG. 9 illustrates a computer-implemented interactive surgical system, in accordance with at least one aspect of the present disclosure.
Figure 10:
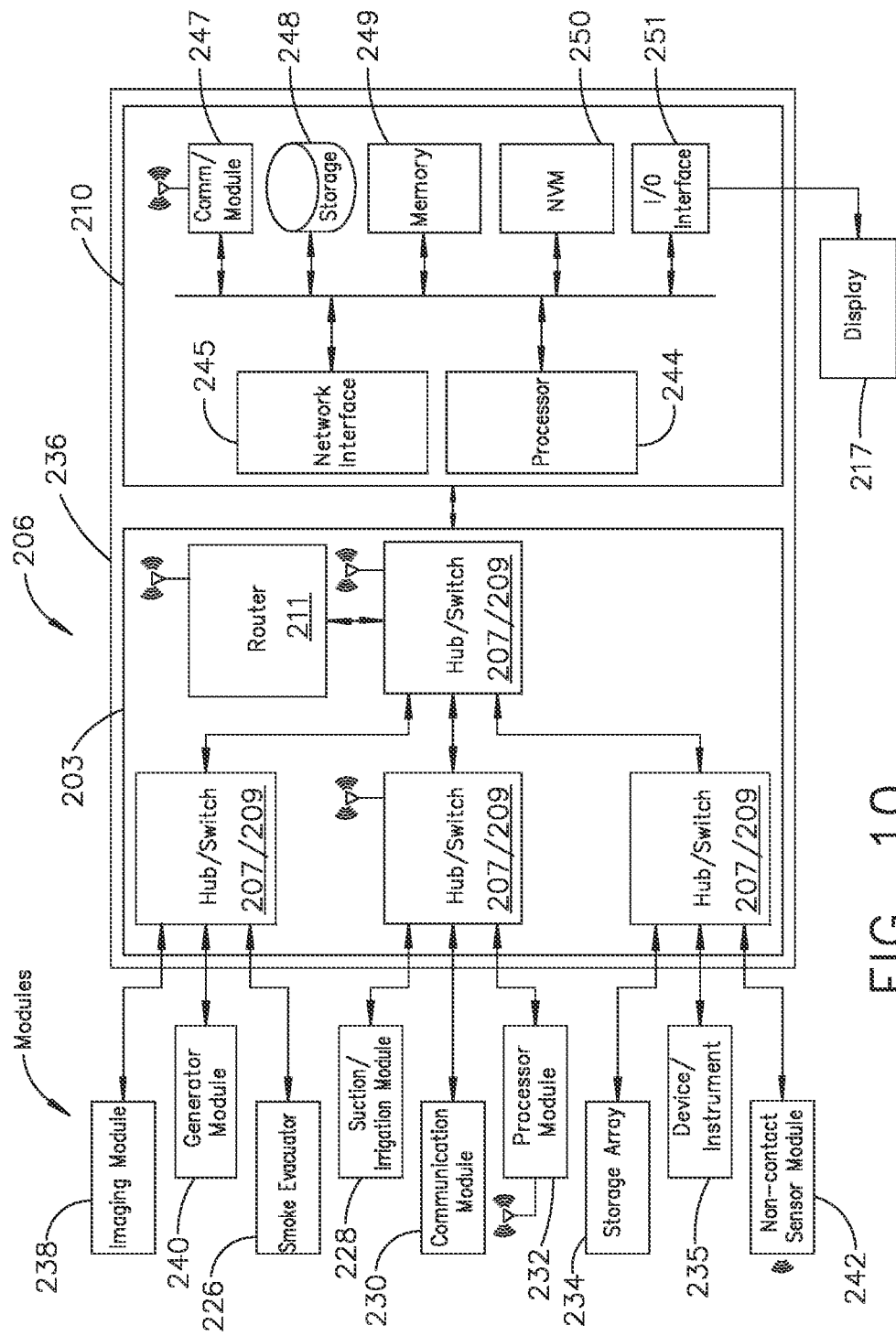
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

In various aspects, the devices/instruments 235 described with reference to FIGS. 9-10, may be implemented as the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26). Accordingly, the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS.

19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26) are configured to interface with the modular control tower 236 and the surgical hub 206. Once connected to the surgical hub 206, the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26) are configured to interface with the cloud 204, the server 213, other hub connected instruments, the hub display 215, or the visualization system 209, or combinations thereof. Further, once connected to hub 206, the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26) may utilize the processing circuits available in the hub local computer system 210.

Figure 11:
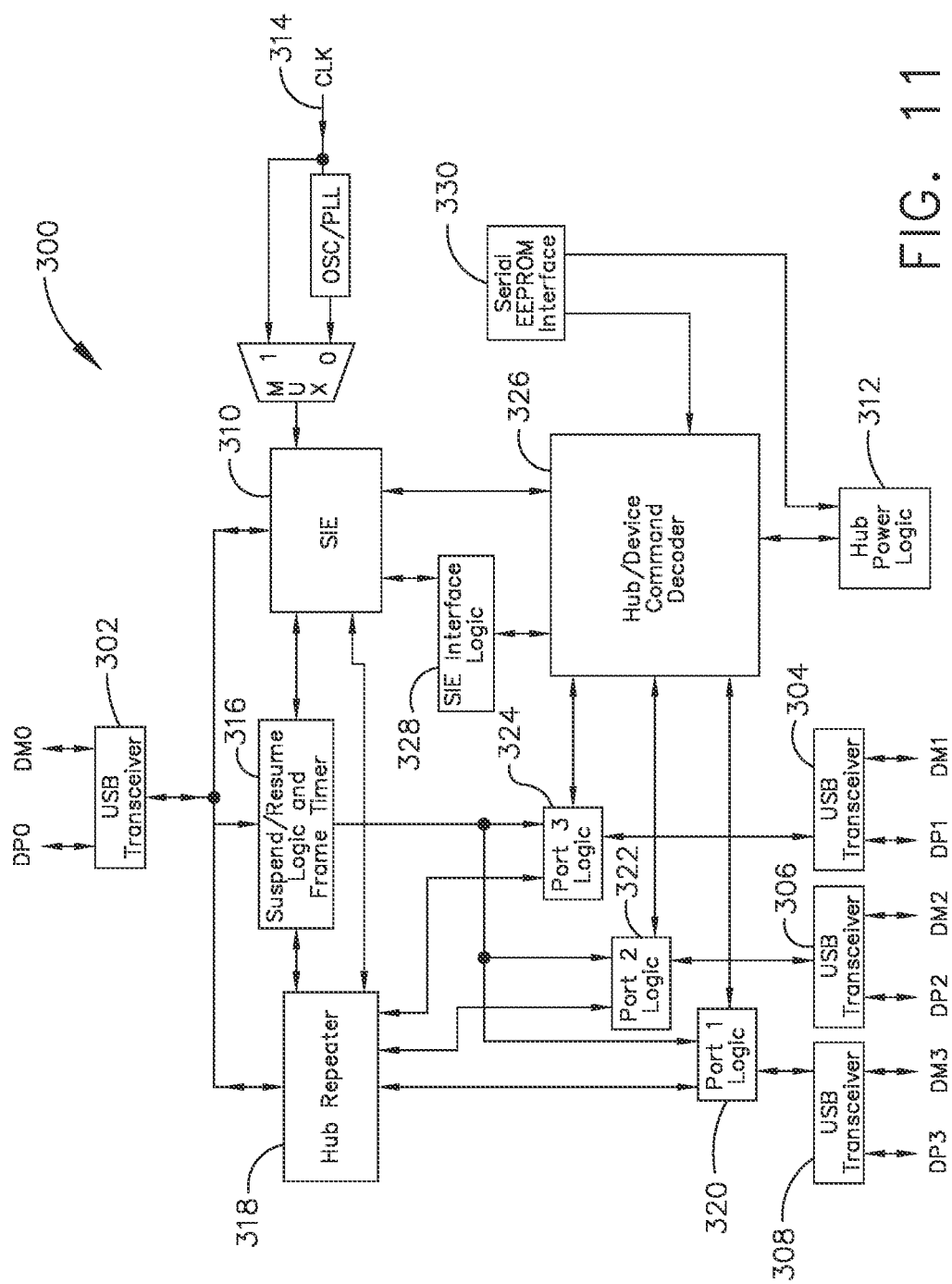
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic 328 to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Additional details regarding the structure and function of the surgical hub and/or surgical hub networks can be found in U.S. Provisional Patent Application No. 62/659,900, titled METHOD OF HUB COMMUNICATION, filed Apr. 19, 2018, which is hereby incorporated by reference herein in its entirety.

Cloud System Hardware and Functional Modules

Figure 12:
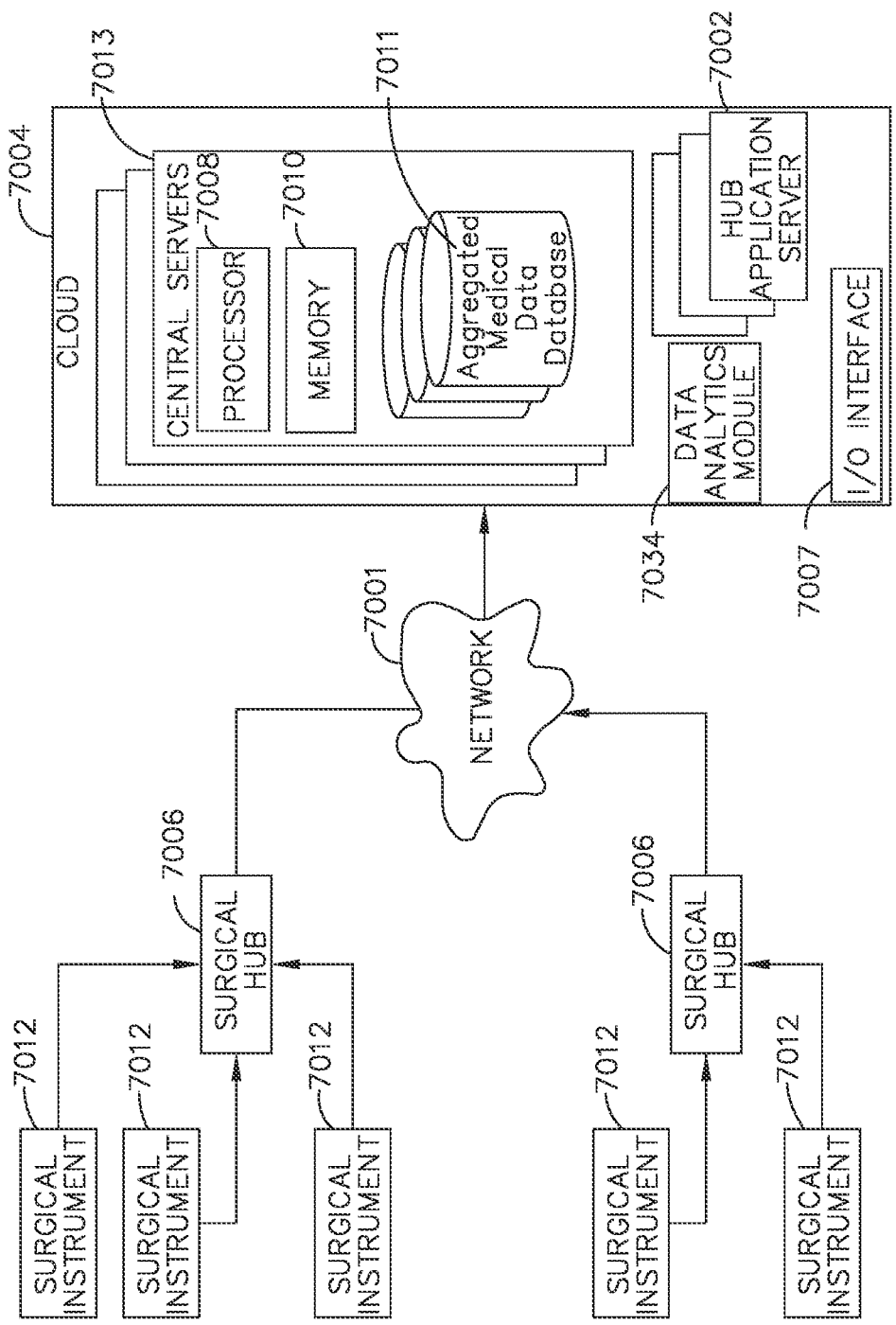
FIG. 12 is a block diagram of a cloud computing system comprising a plurality of smart surgical instruments coupled to surgical hubs that may connect to the cloud component of the cloud computing system, in accordance with at least one aspect of the present disclosure.

FIG. 12 is a block diagram of the computer-implemented interactive surgical system, in accordance with at least one aspect of the present disclosure. In one aspect, the computer-implemented interactive surgical system is configured to monitor and analyze data related to the operation of various surgical systems that include surgical hubs, surgical instruments, robotic devices and operating theaters or healthcare facilities. The computer-implemented interactive surgical system comprises a cloud-based analytics system. Although the cloud-based analytics system is described as a surgical system, it is not necessarily limited as such and could be a cloud-based medical system generally. As illustrated in FIG. 12, the cloud-based analytics system comprises a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 is communicatively coupled to one or more surgical instruments 7012. The hubs 7006 are also communicatively coupled to the cloud 7004 of the computer-implemented interactive surgical system via the network 7001. The cloud 7004 is a remote centralized source of hardware and software for storing, manipulating, and communicating data generated based on the operation of various surgical systems. As shown in FIG. 12, access to the cloud 7004 is achieved via the network 7001, which may be the Internet or some other suitable computer network. Surgical hubs 7006 that are coupled to the cloud 7004 can be considered the client side of the cloud computing system (i.e., cloud-based analytics system). Surgical instruments 7012 are paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 12, the cloud 7004 comprises central servers 7013 (which may be same or similar to remote server 113 in FIG. 1 and/or remote server 213 in FIG. 9), hub application servers 7002, data analytics modules 7034, and an input/output ("I/O") interface 7007. The central servers 7013 of the cloud 7004 collectively administer the cloud computing system, which includes monitoring requests by client surgical hubs 7006 and managing the processing capacity of the cloud 7004 for executing the requests. Each of the central servers 7013 comprises one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical data databases 7011 of the cloud 7004. In particular, the cloud 7004 may advantageously perform data analysis and operations on the aggregated data to yield insights and/or perform functions that individual hubs 7006 could not achieve on their own. To this end, as shown in FIG. 12, the cloud 7004 and the surgical hubs 7006 are communicatively coupled to transmit and receive information. The I/O interface 7007 is connected to the plurality of surgical hubs 7006 via the network 7001. In this way, the I/O interface 7007 can be configured to transfer information between the surgical hubs 7006 and the aggregated medical data databases 7011. Accordingly, the I/O interface 7007 may facilitate read/write operations of the cloud-based analytics system. Such read/write operations may be executed in response to requests from hubs 7006. These requests could be transmitted to the hubs 7006 through the hub applications. The I/O interface 7007 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 are configured to host and supply shared capabilities to software applications (e.g. hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 13.

The particular cloud computing system configuration described in the present disclosure is specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch controlled user interfaces such that clinicians may control aspects of interaction between the surgical instruments 7012 and the cloud 7004. Other suitable user interfaces for control such as auditory controlled user interfaces can also be used.

Figure 13:
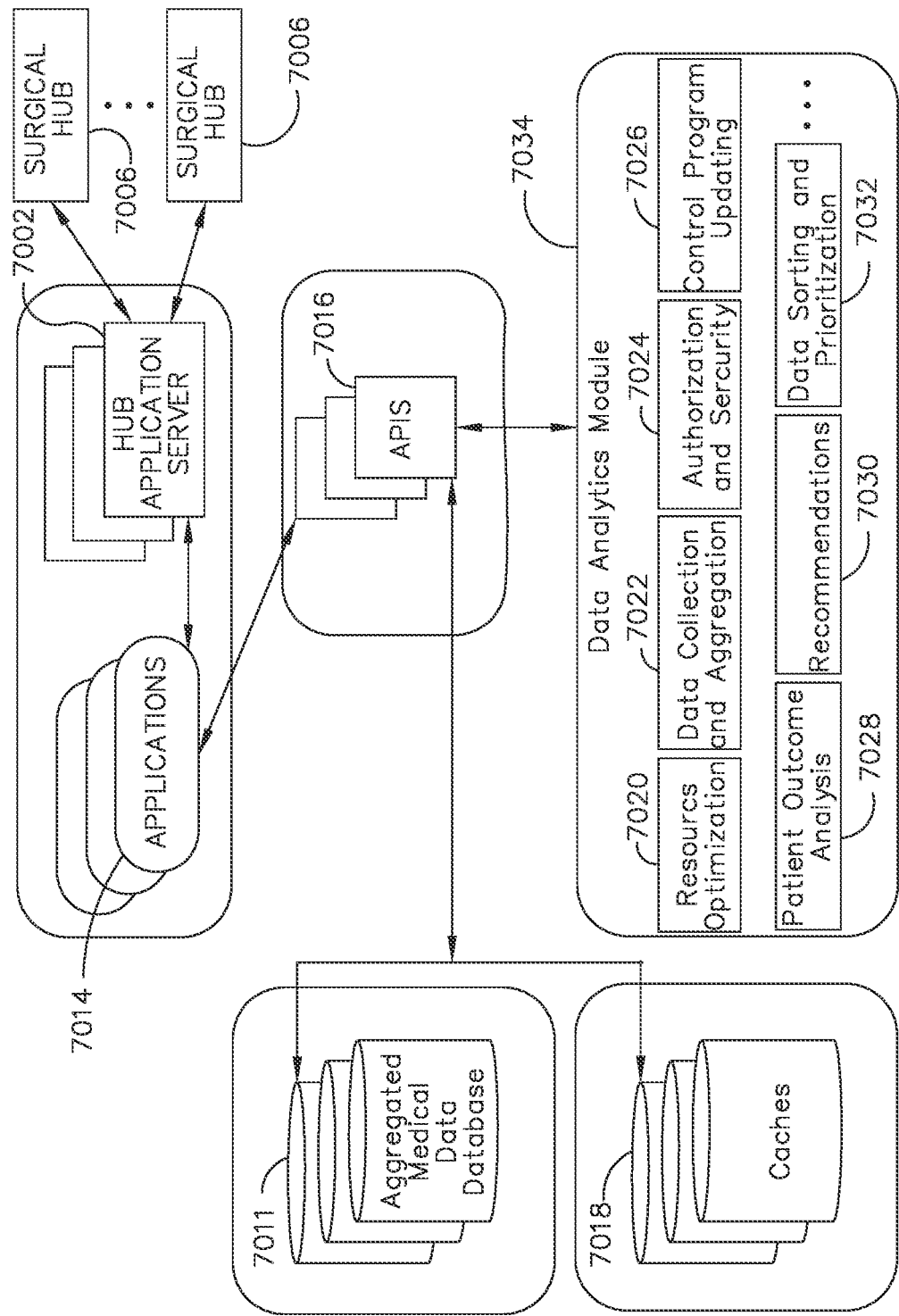
FIG. 13 is a functional module architecture of a cloud computing system, in accordance with at least one aspect of the present disclosure.

FIG. 13 is a block diagram which illustrates the functional architecture of the computer-implemented interactive surgical system, in accordance with at least one aspect of the present disclosure. The cloud-based analytics system includes a plurality of data analytics modules 7034 that may be executed by the processors 7008 of the cloud 7004 for providing data analytic solutions to problems specifically arising in the medical field. As shown in FIG. 13, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 define the set of protocols and routines corresponding to the hub applications 7014. Additionally, the APIs 7016 manage the storing and retrieval of data into and from the aggregated medical data databases 7011 for the operations of the applications 7014. The caches 7018 also store data (e.g., temporarily) and are coupled to the APIs 7016 for more efficient retrieval of data used by the applications 7014. The data analytics modules 7034 in FIG. 13 include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules are used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical hub 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently.

The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that are transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004.

Furthermore, for security purposes, the cloud could maintain a database of hubs 7006, instruments 7012, and other devices that may comprise a "black list" of prohibited devices. In particular, a surgical hub 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electro-surgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described above to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g. a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

In various aspects, the surgical instrument(s) 7012 described above with reference to FIGS. 12 and 13, may be implemented as the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26). Accordingly, the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26) are configured to interface with the surgical hub 7006 and the network 2001, which is configured to interface with cloud 7004. Accordingly, the processing power provided by the central servers 7013 and the data analytics module 7034 are configured to process information (e.g., data and control) from the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26).

Additional details regarding the cloud analysis system can be found in U.S. Provisional Patent Application No. 62/659,900, titled METHOD OF HUB COMMUNICATION, filed Apr. 19, 2018, which is hereby incorporated by reference herein in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 14:
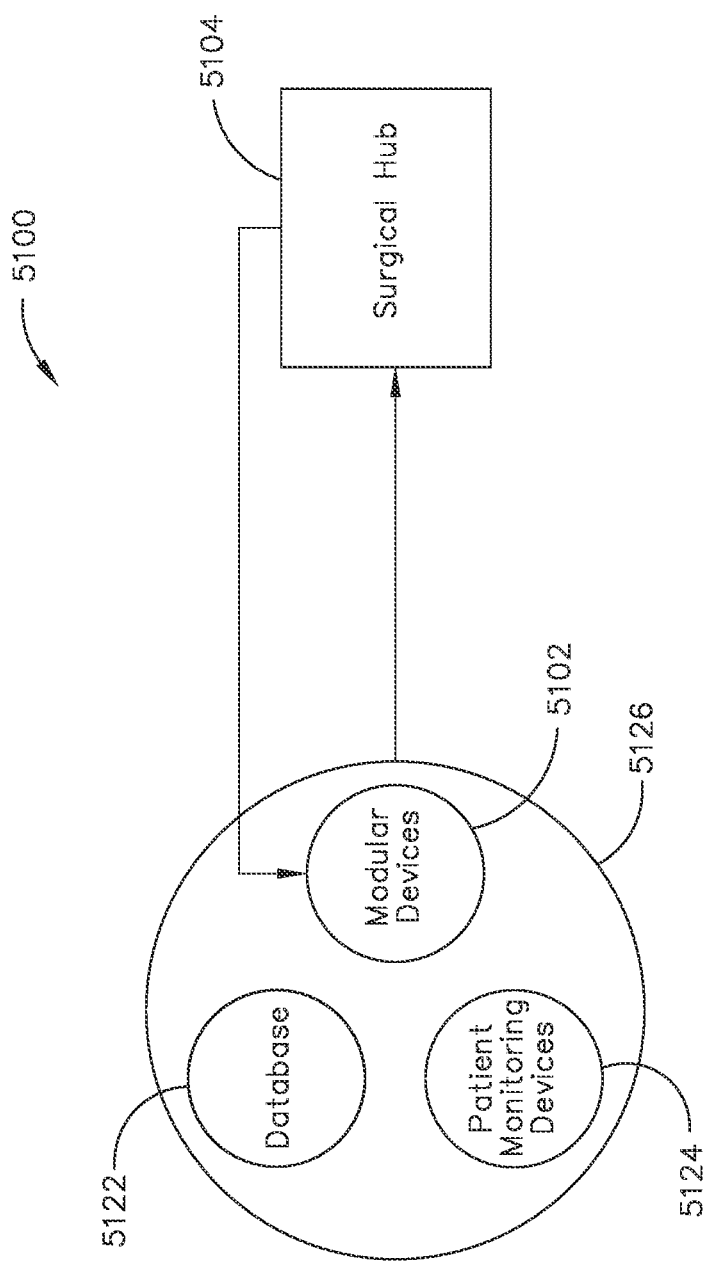
FIG. 14 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 14 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor).

A surgical hub 5104, which may be similar to the hub 106 in many respects, can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure scanned by a suitable scanner, for example, and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

In one aspect, as described hereinbelow with reference to FIGS. 24-40, the modular device 5102 is implemented as the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26). Accordingly, the modular device 5102 implemented as the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26) are configured to operate as a data source 5126 and to interact with the database 5122 and patient monitoring devices 5124. The modular device 5102 implemented as the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26) are further configured to interact with the surgical hub 5104 to provide information (e.g., data and control) to the surgical hub 5104 and receive information (e.g., data and control) from the surgical hub 5104.

Figure 15:
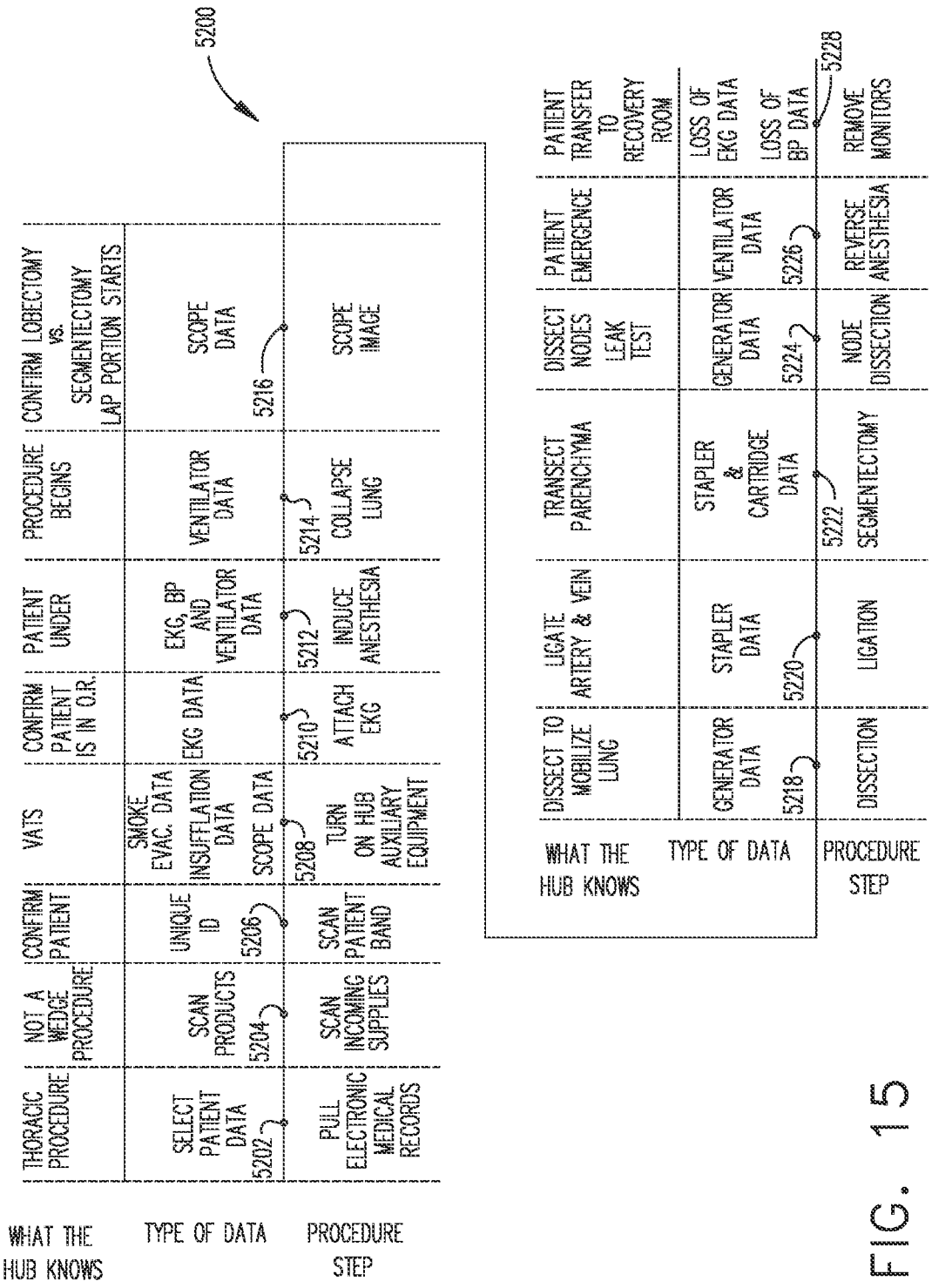
FIG. 15 is a timeline depicting situational awareness of a surgical hub, in accordance with at least one aspect of the present disclosure.

Referring now to FIG. 15, a timeline 5200 depicting situational awareness of a hub, such as the surgical hub 106 or 206 (FIGS. 1-11), for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 5204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 5206, the medical personnel scan the patient band via a scanner that is communicably connected to the surgical hub 106, 206. The surgical hub 106, 206 can then confirm the patient's identity based on the scanned data.

Fourth step 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 5210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 5212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 5212, the pre-operative portion of the lung segmentectomy procedure is completed and the operative portion begins.

Seventh step 5214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 5216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 5218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 5220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 5222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 5224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 5224, the incisions are closed up and the post-operative portion of the procedure begins.

Thirteenth step 5226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 5228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

In various aspects, the combination energy instrument 213100 (FIG. 18), the surgical stapler 213102 (FIG. 18), the suction/irrigation device 213104 (FIG. 18), the sterile field display 213108 (FIG. 18), the surgical device 213204 (FIGS. 19A and 19B), the surgical evacuation system 50400 (FIG. 21), the electrosurgical instrument 50630 (FIG. 22), the evacuation system 50600 (FIG. 22), the evacuation system 50900 (FIG. 23), the scope 213501 (FIG. 25), and the surgical device 213608 (FIG. 26) are configured to operate in a situational awareness in a hub environment, such as the surgical hub 106 or 206 (FIGS. 1-11), for example, as depicted by the timeline 5200. Situational awareness is further described in U.S. Provisional Patent Application Ser. No. 62/659,900, titled METHOD OF HUB COMMUNICATION, filed Apr. 19, 2018, which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

Adaptive Control Schemes and Interactive System Controls

In various aspects, a computer system, such as the computer system of a surgical hub, for example, can be configured to extract deeper context around captured data and then utilize this deeper context to improve indications of actionable items for the operator. Deeper context can include metadata and data combinations, in which data from different sources and/or obtained at different times (e.g., preoperatively, intraoperatively, postoperatively) is synthesized to determine relationships and/or correlations. In one instance, the context of the data can be informed by the situational awareness of the surgical hub during a surgical procedure, which can indicate actionable items, such as step-specific or timed adjustments and/or recommendations for the clinician. The system can be configured to implement an adjustable controls scheme with interdependent control aspects. For example, the system can be configured to provide an adaptive control scheme with interactive system controls based on the captured data.

In one aspect, a control for a surgical hub or hub-connected device can be configured to adjust its function (or have its function adjusted) based on a sensed situation or usage. The function can be adjusted by adjusting a scale or degree of the surgical function (e.g. a power level or clamping force), adjusting one or more thresholds of the surgical function (e.g. maximum and minimum power level limits), adjusting a resulting action of the surgical function (e.g. changing an energy modality), adjusting a type of measurement for affecting the surgical function (e.g. from an on-off activation to an operator-controlled variable activation), and/or adjusting a complementary action for the surgical function (e.g. adjusting a clamping force based on a selected energy modality), for example. Additional examples of adjustments to surgical functions are described herein.

In one aspect, the type of measurement can change between an on-off activation detection to a measurement of degree, such as with a strain gauge or Hall Effect sensor. For example, an actuator for a surgical function can act as an on-off actuator in a first mode corresponding to a first surgical state and a degree-based actuator in a second mode corresponding to a second surgical state. The degree-based actuator can be configured to adjust a firing stroke length and/or force, an end effector closure amount and/or clamping force, and/or an energy activation type and/or level, for example. In one aspect, an activation and/or deactivation threshold can be adjusted based on the time in the procedure and/or whether it is a precision-usage surgical step or a gross-usage surgical step, which can be informed by the situational awareness of the system, for example.

In one aspect, a surgical hub can be configured to prioritize a visual indication on a display within the operating room or surgical theater of actionable contextual secondary information gathered from the data available during the procedure. The prioritization can be based on the certainty and/or importance of the actionable information, for example. In one aspect, an activation or toggling icon for the actionable information can include highlighting where the normal graphical interface is less highlighted. The display can be on a surgical device or a main display (e.g., a display connected to the surgical hub), for example.

In certain instances, a clinician may want to use a surgical device for multiple surgical functions. For example, a surgical device can be used to coagulate blood vessels, cut tissue, and/or seal tissue. In order to achieve these different functions, the control scheme for the surgical device can be adjusted. For example, different power levels or thresholds can be utilized. Additionally or alternatively, different energy modalities (e.g., ultrasonic, bipolar, and monopolar) can be utilized. It can be desirable to switch between the different surgical functions quickly and without relying on complex controls on the surgical device and/or on a remote console. In certain instances, it can be desirable to implement such control scheme adjustments and adaptations with existing surgical devices and/or using surgical devices having minimal input controls, i.e. actuators.

In certain aspects, a surgical system can be configured to implement automatic changes in controls based on monitored conditions within the procedure. A single input control or actuator can be utilized to effect different surgical functions. The available surgical functions actuatable with the input control can depend on the surgical step or state of a surgical procedure. In various instances, a situationally-aware surgical hub or hub-connected surgical device can determine the surgical step and/or state from the situational awareness thereof. Accordingly, the system can be configured adjust devices' control schemes based on situational awareness of the user's intent. In one instance, in a first surgical state (determined by the situational awareness of the surgical hub), the power level of a transducer can be defined by a first range and, in a second surgical state (determined by the situational awareness of the surgical hub), the power level of the transducer can be defined by a second, different range. Additionally or alternatively, in a first surgical state (determined by the situational awareness of the surgical hub), a combination energy device can operate in a combination mode and, in a second surgical state (determined by the situational awareness of the surgical hub), the combination energy device can operate in an ultrasonic mode without the application of electrosurgical energy. The different surgical functions can be implemented by a single actuator, which can comprise a smart or intelligent actuator that is informed by the situational awareness of a surgical hub.

In one aspect, a surgical device can comprise an actuator configured to receive an input. The surgical device can further comprise a control circuit configured to receive a signal from a situationally-aware surgical hub indicative of a surgical state, receive an actuation signal from the actuator in response to the input, and implement a surgical function in response to the actuation signal. The surgical function can comprise a first surgical function when the surgical state corresponds to a first surgical state and a second surgical function when the surgical state corresponds to a second surgical state. The second surgical state can be different than the first surgical state and the second surgical function can be different than the first surgical function. In another aspect, a non-transitory medium storing computer readable instructions can, when executed, cause a machine, like an intelligent surgical device, to receive a signal from a situationally-aware surgical hub indicative of a surgical state, receive an actuation signal in response to an input applied to an actuator of a surgical device, and implement a surgical function in response to the actuation signal. The surgical function can comprise a first surgical function when the surgical state corresponds to a first surgical state and a second surgical function when the surgical state corresponds to a second surgical state. The second surgical state can be different than the first surgical state and the second surgical function can be different than the first surgical function. Alternative control scheme adjustments and adaptions are further described herein.

As further described herein, the function of a control, such as an actuator, for example, can be adjusted based on one or more factors, including the other instruments currently in use in the surgical theater, the step of the surgical procedure, and/or the input to a secondary control of the surgical device. Such factors can be determined, at least in part, from situational awareness, as further described herein.

Figure 16:
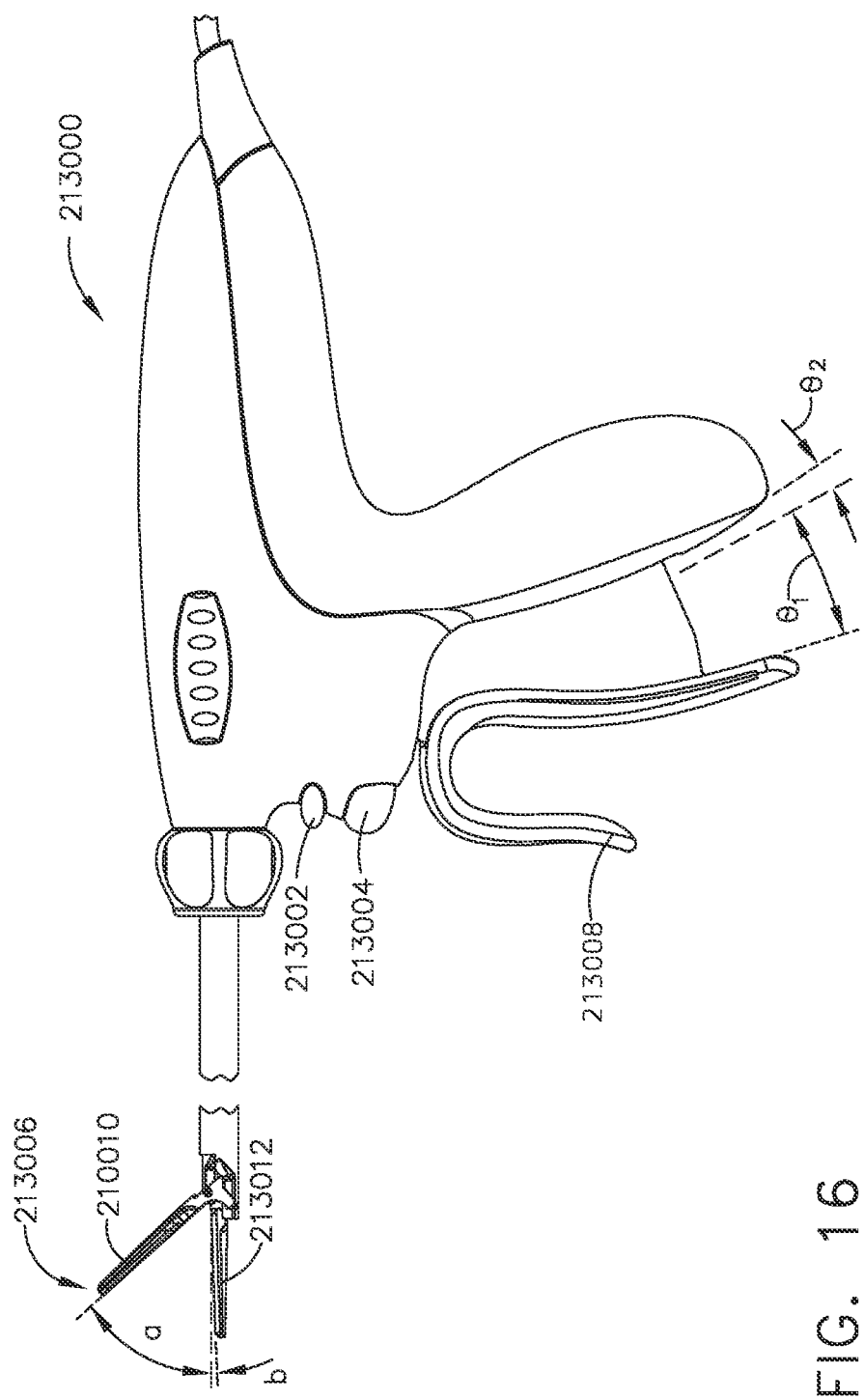
FIG. 16 is an elevation view of a surgical instrument including an end effector and a trigger, wherein the degree to which the end effector is closed is controlled by the degree to which the trigger is actuated, in accordance with at least one aspect of the present disclosure.

In some applications, the degree of displacement of an actuator and/or the input force on the actuator of a surgical device can affect the power (e.g. amplitude) limits of the surgical device. Referring now to FIG. 16, an energy device 213000 can include a first actuation button 213002 and a second actuation button 213004. In various instances, the first actuation button 213002 can correspond to a first power level, and the second actuation button 213004 can correspond to a second power level. For example, the first actuation button 213002 can comprise a higher, or maximum, power level, which can correspond to a cutting mode, and the second actuation button 213004 can comprise a lower, or minimum, power level, which can correspond to a coagulating mode. In such instances, the first actuation button 213002 can be referred to as a "cut button", and the second actuation button 213004 can be referred to as a "coagulation button."

The actuation buttons 213002, 213004 can have a spring bias aspect that allows the actuation buttons 213002, 213004 to act as on-off switches and also detect the force that an operator applies thereto. In one aspect, the actuation buttons 213002, 213004 can have a first or normal activation that accounts for a particular portion of the button's range of motion and a second or modified activation that accounts for another portion of the button's range of motion. For example, the first 70-80% of the button's range of motion can effect activation of energy and the remaining portion of the button's range of motion can adjust the energy level. In such instances, if the clinician were to compress either actuation button 213002, 213004 farther by overcoming the higher bias force, then the button could change function and not only apply the cut or coagulation energy level, but increase the power level from the level set on the generator. For example, the power level could be increased one level when the actuation buttons moves into the remaining portion of the button's range of motion. In this operation, the high-force actuation would act to both activate the energy and increase the power level of the energy.

In one aspect, the surgical functions controlled by the actuation buttons 213002, 213004 can be subject to the position of an end effector 213006 and/or a closure trigger 213008. For example, referring still to FIG. 16, movement of the closure trigger 213008 through a first range of motion (i.e. through a first angle $\theta_1$), can effect closure of the end effector 213006 a first amount, a first distance a. Movement of the closure trigger 213008 through a second range of motion (i.e. through a second angle $\theta_2$), can affect closure of the end effector 213006 a second amount, a second distance b. In certain instances, the first amount can correspond to a closure motion of jaws 213010, 213012, and the second amount can correspond to a clamping motion of the jaws 213010, 213012. The first jaw 213010 can be a clamp arm, which can move relative to the second jaw 213012 in certain instances. In other instances, the second jaw 213012 alone and/or both jaws 213010, 213012 can be moved by the closure trigger 213008 to close and/or clamp the end effector 213006.

The first actuation button 213002 and/or the second actuation button 213004 can implement different surgical functions based on the position of the closure trigger 213008 and/or the clamp arm 213010. For example, if the actuation buttons 213002, 213004 were activated when the jaws 213010, 213012 of the end effector 213006 are between the fully open and a partially-closed threshold (e.g., only closed ⅔ of the entire closure range), the actuation buttons 213002, 213004 can have respective first energy levels. Further, if the jaws 213010, 213012 are moved beyond the partially-closed threshold (e.g., over ⅔ closed), the first and second actuation buttons 213002, 213004 can have respective second energy levels. The second energy level for each button 213002, 213004 can be higher than the corresponding first energy levels for the respective actuation buttons 213002, 213004. For example, the energy levels can be higher when the jaws 213010, 213012 are more closed, such as when the jaws 213010, 213012 are actively clamping tissue therebetween.

Figure 17:
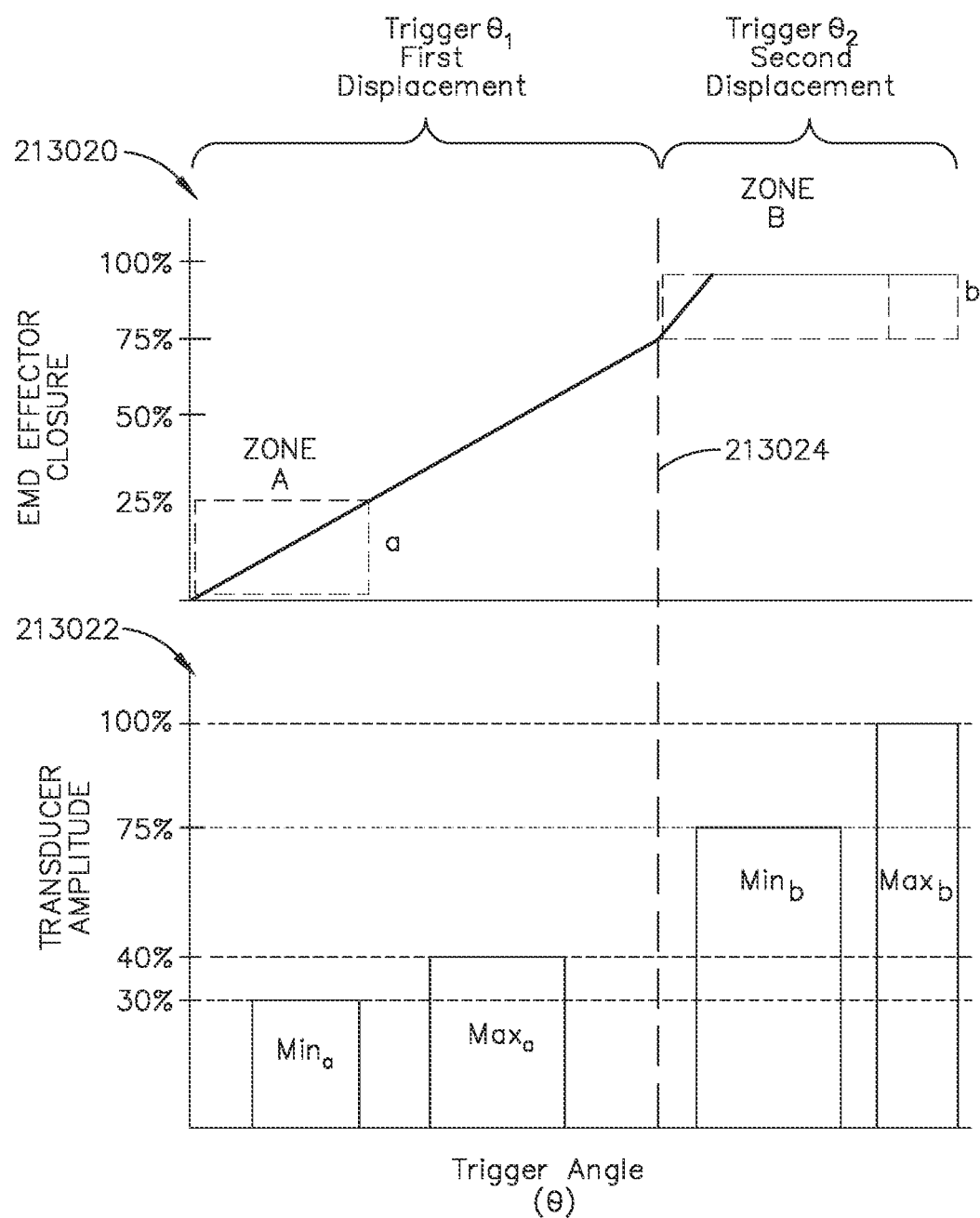
FIG. 17 is a pair of graphs depicting end effector closure and transducer amplitude relative to trigger angle for the surgical instrument of FIG. 16, in accordance with at least one aspect of the present disclosure.

A pair of graphs 213020, 213022 depicting jaw closure and transducer amplitude relative to trigger angle ($\theta$) for the energy device 213000 are depicted in FIG. 17. Referring to the graph 213020, a control algorithm for the energy device 213000 is configured to adjust the amplitude of an ultrasonic transducer according to the trigger angle ($\theta$), i.e. the degree to which the closure trigger 213008 (FIG. 16) is depressed. The amplitude can be adjusted at one or more thresholds, such as the trigger angle threshold 213024 indicated in FIG. 17.

More specifically, during a first range of motion of the closure trigger 213008 (e.g. through the first trigger displacement angle $\theta_1$) the first actuation button 213002 can activate energy at a first maximum threshold $Max_a$ and the second actuation button 213004 can activate energy at a first minimum threshold $Min_a$. During a second range of motion of the closure trigger 213008 (e.g. through the second trigger displacement angle $\theta_2$) the first actuation button 213002 can activate energy at a second maximum threshold $Max_b$ and the second actuation button 213004 can activate energy at a second minimum threshold $Min_b$. In the depicted graph 213022, the first minimum threshold $Min_a$ is different than the second minimum threshold $Min_b$ and the first maximum threshold $Max_a$ is different than the second maximum threshold $Max_b$. More specifically, the first minimum threshold $Min_a$ is less than the second minimum threshold $Min_b$ and the first maximum threshold $Max_a$ is less than the second maximum threshold $Max_b$. As shown in FIG. 17, the first minimum threshold $Min_a$ comprises 30% of the transducer amplitude limit, whereas the second minimum threshold $Min_b$ comprises 75% of the transducer amplitude limit. Additionally, the second maximum threshold $Max_b$ comprises 100% of the transducer amplitude limit, whereas the first maximum threshold $Max_a$ only comprises 40% of the transducer amplitude limit. Other threshold values are contemplated. For example, the second minimum threshold $Min_b$ can be less than the first maximum threshold $Max_a$.

In still other instances, the first minimum threshold $Min_a$ can be greater than the second minimum threshold $Min_b$ and/or the first maximum threshold $Max_a$ can be greater than the second maximum threshold $Max_b$. In still other instances, only one of the limits can be adjusted when the trigger displacement angle exceeds the trigger angle threshold 213024. For example, the second actuation button 213004 can maintain the first minimum threshold $Min_a$ during the entire range of motion of the closure trigger 213008, including the angles $\theta_1$ and $\theta_2$. In other words, the amplitude of the transducer can be maintained at 30% when the second actuation button 213004 is depressed regardless of the position of the first jaw 213010 and/or the closure trigger 213008. Additionally or alternatively, one or more of the limits can be adjusted at additional trigger angle thresholds.

Referring now to the graph 213020, a closure rate for the closure trigger 213008 can also be adjusted based on a detected surgical state and/or surgical step. For example, the closure trigger 213008 can be closed at a first rate during a first range of motion through the first trigger displacement range $\theta_1$, and the closure trigger 213008 can be closed at a second rate during a second range of motion through the second trigger displacement range $\theta_2$. More specifically, the first rate, which corresponds to a slope a/ZONE A, can continue until the closure trigger 213008 meets the trigger angle threshold 213024. In the depicted arrangements, the trigger angle threshold 213024 corresponds to 75% end effector closure. In other instances, the trigger angle threshold 213024 can define less than or more than 75% end effector closure, such as $\frac{2}{3}^{rd}$ closed and/or 90% closed, for example. Upon reaching the trigger angle threshold 213024, the closure rate can be increased to a second rate in ZONE B until the closure trigger 213008 is 100% closed. In other instances, the closure rate can be decreased upon reaching the trigger angle threshold 213024. Additionally or alternatively, the closure rate can be adjusted at additional trigger angle thresholds.

In various instances, the position of the closure trigger 213008 can indicate a surgical state of the surgical procedure. For example, the closure trigger 213008 can remain open during a first surgical step, be closed to a first degree during a second surgical step, and be closed to a second degree during a third surgical step. For example, open jaws can be used to cauterize blood vessels, partially closed jaws can be used to coagulate tissue, and/or completely closed jaws can be used to cut tissue. By monitoring the position of the closure trigger 213008, the control circuit is configured to determine the surgical state and/or step, and adjust a surgical function, i.e. a power level, of the hub-connected device based on the detected state and/or step. Situational awareness can further inform the determination. For example, during a certain type of surgical procedure and/or when treating a certain type of tissue, the maximum and/or minimum threshold(s) and/or trigger angle threshold(s) can be adjusted in a first manner and, during another type of surgical procedure and/or when treating another type of tissue, the maximum and/or minimum threshold(s) and/or trigger angle threshold(s) can be adjusted in a second manner. For example, lung tissue and stomach tissue can necessitate different responses. Additionally or alternatively, arteries and veins can necessitate different thresholds. Situational awareness can determine the surgical procedure and/or tissue type.

In various instances, one or more controls and/or actuators for a surgical device can be adjusted based on another control/actuator on the surgical device. Actuating a first control/actuator can cause a second control/actuator to have an adjusted function. Referring again to FIG. 16, for example, if the jaws 213010, 213012 of the energy device 213000 are open wide and energy is activated via one of the activation buttons 213002, 213004, a surgical system can sense or otherwise determine that the surgeon intends to use the instrument for a first surgical function, such as back cutting, for example. Accordingly, the minimum and maximum power levels (e.g., amplitude) can be set to their normal levels for the first surgical function. If the jaws 213010, 213012 of the energy device 213000 are more than half open, the energy actuation button(s) 213002, 213004 can drive an ultrasonic response only; however, if the jaws 213010, 213012 are more than half closed, the energy device 213000 can function in a standard combination ultrasonic-electrosurgical mode. As yet another example, if the jaws 213010, 213012 of the energy device 213000 are fully clamped at the highest compression level as ultrasonic energy is being applied and the user requests more pressure via the closure trigger 213008 while still actuating the maximum energy activation button 213002, the energy modality can automatically shift from ultrasonic to electrosurgical RF, and the energy device 213000 can further increase the pressure applied with the clamping jaw 213010.

In one aspect, controls can be adjusted according to the other instruments currently in use in the same surgical theater. For example, if a secondary energy device is within the field of view (e.g., the field of view of a scope) and a predefined key and/or sequence of control actuators are actuated, the surgical hub can adjust the controls for a primary energy device also within the field of view. In one instance, when the closure trigger and energy button are actuated on a primary energy device and a secondary device is within the field of view, a scalable adjustment control on the secondary energy device can be used to control the power level for the primary energy device. In such instances, the generator powering the primary energy device can be turned up or down with a control on the secondary energy device. Such remote control of a surgical function can only be enabled when a predefined sequence of surgical actions have been performed and/or during a particular step in a surgical procedure in various instances.

In another example, touching or contact between surgical devices can allow one of the surgical devices to adjust the controls of the other surgical device. For example, if a second surgical device touches a first surgical device, then a particular action or combination of actions performed by or on the second surgical device can cause a control algorithm to adjust a function of the first surgical device. For example, when the jaws of the second surgical device are in a fully open configuration, the jaws can press an actuation button on the first surgical device, and then an adjustment control on the second surgical device can be used to the change the power level of the first surgical device, such as the power provided by a generator, for example. Once the desired level is set, the second surgical device can be removed from contact with the first surgical device. Thereafter, the first and second surgical devices can operate as normal devices at the newly-set power level. In one instance, continuity sensors can be configured to detect the contact between the surgical devices.

In one aspect, controls for a surgical device can be adjusted according to the step of the surgical procedure being performed. Situational awareness can inform the surgical hub of the current and/or next step of the surgical procedure. For example, based on the previous surgical actions and/or the order of usage of the surgical device(s) and/or generator(s), a surgical hub can determine what particular step of a particular surgical procedure is being performed, such as whether the procedure is currently in a nodal dissection step, vessel transecting step, and so on. If the surgical hub determines that the energy device being used is in a fine dissection mode, the system can automatically adjust the function of the energy device's buttons to different settings, e.g., a lower power setting for use with this procedural step. In one implementation, the surgical hub and/or generator can determine the procedural specific step or context.

In another implementation, the system can learn and anticipate the procedural specific step or context by analyzing the particular clinician's most common usage at each stage of the surgical procedure and/or after a particular number or type of surgical instrument exchanges. In such a learned mode, the generator, in one aspect, does not initially implement any automatic adjustments to the controls. Rather, after monitoring the same clinician's behavior over a predetermined number of procedures that include the same steps, the surgical device can automatically change the button usage based on the monitored and past usage by the clinician. In various instances, the surgical device can provide notice to the clinician when the function of the controls is adjusted. For example, the surgical device can provide an auditory notice (e.g., a beep or verbal explanation), a visual cue (e.g. a flashing light and/or words on a screen), and/or a tactile warning (e.g. vibrations and/or movement of the surgical device or a portion thereof, such as the actuator button itself). In other instances, the surgical hub can recommend an adjustment to the controls. Recommendations from a surgical hub are further described herein.

In various aspects, controls for a surgical hub, surgical instruments, and other devices can be adjusted based on a screen in operation on a sterile field display. The controls of the surgical devices can be adjusted based on the displayed information. In one aspect, a control that normally controls panning or adjusting the focus of a visualization device (e.g., a scope) can be configured to adjust magnification if a hyperspectral imaging overlay is active, for example. Hyperspectral imaging is further described in U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

As another example, the on-handle controls for a surgical instrument in the field of view of a sterile field display can be adjusted by selections on the sterile field display. Moreover, the adjustments can be based on situational awareness in various instances. For example, the system can determine that a particular surgical device is being utilized and permit the functions of that surgical device to be controlled from a second device, such as a display screen within the sterile field. Referring now to FIG. 18, a surgical procedure involving a combination energy instrument 213100, a surgical stapler 213102, a suction/irrigation device 213104, and a sterile field display 213108 is shown. The combination energy device 213100 includes a single energy button 213110, which is configured to implement different energy modalities. For example, the combination energy device 213100 can operate in a bipolar mode, monopolar mode, ultrasonic mode, and/or various combinations thereof (e.g. a blended mode). In one instance, the combination energy device 213100 can operate in a monopolar-bipolar mode. In another instance, the combination energy device 213100 can operate in an ultrasonic-bipolar mode and, in still other instances, the combination energy device can operate in an ultrasonic-monopolar mode. The various energy modalities can be applied sequentially and/or blended together simultaneously.

In one aspect, the controls on the handle of a surgical instrument in the field of view of a sterile field display 213108 can be adjusted by selections on the sterile field display 213108. For example, the combination energy instrument 213100 includes a single button 213110, which can be configured to apply energy to selectively cut and coagulate tissue. The energy modality activated by the button 213110 can be adjusted with a selection on the sterile field display 213108.

In one aspect, the energy activation button 213110 can have an indicator that changes or otherwise indicates when the sterile field display 213108 is being used to change the function of the button 213110 and/or that the sterile field display 213108 has shared control of the button 213110. For example, the combination energy device 213100 can include an LED on the handle and/or the energy activation button 213110 itself that can change color and/or otherwise changes its appearance (e.g. change the color of the energy activation button 213110 and/or become illuminated with flashing and/or pulsing light) when adjusted from a secondary device, such as the sterile field display 213108. In one instance, the button 213110 can have a normal red hue projected through light channels from a multicolor LED for a cutting function, whereas a blue hue can be projected through the light channels from the multicolor LED for a coagulation function. When the sterile field display 213108 changes the surgical function to a blended energy modality, for example, the button 213110, which was red, can be changed to purple. In various instances, the interface area on the sterile field display 213108 can also include an indicator in a corresponding color (e.g. purple words and/or highlighting when the button 213110 is illuminated with a purple hue) to indicate that the functions between the displayed controls on the surgical field display 213108 and the combination energy device 213100 are linked.

Various surgical instruments can be controlled in different ways depending on the number and type of buttons/actuators thereon, as well as the desired surgical functions for the surgical instrument. For example, if a surgical instrument includes two buttons (e.g., a first button corresponding to a first power level that is suitable for coagulation and a second button corresponding to a second power level that is suitable for cutting) the sterile field display 213108 can be configured to adjust the functions of the first and second buttons. For example, one of the buttons can be utilized to activate monopolar energy and the other button can be configured to activate a blended energy. In such instances, the buttons can include an indicator (e.g. a color LED) that changes when the sterile field display 213108 is being used to change the function of the buttons and/or to indicate that the sterile field display 213108 has shared control of the buttons. The indicator can communicate the selected energy modality and/or how the energy modality was selected. For example, the first button can include a red-hued LED, and the second button can include a blue-hued LED. When the first button is configured to activate a blended energy modality, the red-hued LED can become purple-hued. Additionally, the interface area on the sterile field display 213108 can include a purple indicator.

In various instances, the sterile field display 213108 can allow a clinician to switch the functions of the buttons on the handle of the combination energy device 213100. In such instances, the color of the two buttons could be reversed. In another instance, the functions of the buttons can be changed. For instance, the second button (which previously corresponded to a power level suitable for cutting tissue, for example) can be changed to an energy activation button, and the first button (which previously corresponded to a power level suitable for coagulating tissue, for example) can be changed to a power level adjustment control. In such instances, each time the power level adjustment control is activated, the sterile field display 213108 can show the newly-selected power level. For example, the sterile field display 213108 can utilize a flashing icon to indicate a change to the generator power level. Thereafter, activation of the second button (currently acting as the energy activation button) can be used to activate and deactivate energy at the newly-set power level.

In still other instances, the button 213110 and/or other buttons on the combination energy device 213100 can be changed from on-off activation functions to a pressure-sensitive activation function. For example, a higher level of force applied to the button 213110 can be configured to increase the intensity of the energy activation such as by turning up the power level based on the force on the button 213110. Further, the sterile field display 213108 can be used to change the discrete on/off function of the button 213110 to a pressure-sensitive adjustment function. Further, the sterile field display 213108 and the button(s) 213110 can utilize different indications when the power level is changed. For instance, the light emitted from the button(s) could vary in intensity as the pressure-sensitive activation adjusts the power level of the combination energy device 213100. Additionally, the sterile filed display 213108 can indicate a color that is synchronized with the color of the button 213110 to indicate the current function and pairing.

In various instances, a surgical hub can be configured to provide recommendations to a clinician during a surgical procedure. For example, the surgical hub can aggregate data from multiple sources to determine a recommended surgical action. In various instances, the recommendations can be based on the situational awareness of the surgical hub. The relevancy or importance of a recommendation can depend on the surgical context or scenario. For example, a general recommendation can be escalated to a higher level based on data obtained by various data sources and/or sensors. Because a surgical hub is able to aggregate significant volumes of information, it can be helpful to prioritize recommendations for the clinician to avoid overwhelming the clinician with too much data at a given time. For example, if a clinician is constantly being interrupted with recommendations—of which some or many are non-relevant and/or unhelpful—the clinician may ignore the hub's recommendations entirely and/or disable a recommendation setting on the surgical hub. By prioritizing recommendations based on situational awareness, the clinician can be well-informed with respect to actionable and/or time-sensitive items.

In various instances, the importance of the recommendation can depend on a position of a surgical device. For example, actionable aspects can be highlighted or emphasized to the clinician. Additionally, non-actionable and/or non-critical aspects can be displayed discretely and/or selectively hidden from view. If the position of the surgical device indicates that a recommendation is actionable by the clinician, the surgical hub can emphasize the recommendation whereas the non-actionable recommendations can be displayed more discretely and/or selectively hidden from view. In such instances, actionable recommendations are selectively communicated to the clinician, which enables the clinician to consider the value of such a recommendation in a timely manner.

In various instances, for example, a surgical system can include a screen configured to selectively display a recommendation to a clinician in an operating room. The surgical system can also include a control circuit communicatively coupled to the screen and a situationally-aware surgical hub, wherein the control circuit is configured to receive a signal from the situationally-aware surgical hub indicative of a surgical state, determine a priority level of the recommendation based on the surgical state, and communicate the priority level of the recommendation via the display. In various instances, the control circuit comprises a processor and a memory communicatively coupled to the processor, the memory storing instructions executable by the processor to receive a signal from the situationally-aware surgical hub indicative of a surgical state, determine a priority level of the recommendation based on the surgical state, and communicate the priority level of the recommendation via the display. In various instances, a non-transitory computer readable medium stores computer readable instructions which, when executed, cause a machine, like an intelligent surgical device, to receive a signal from the situationally-aware surgical hub indicative of a surgical state, determine a priority level of the recommendation based on the surgical state, and communicate the priority level of the recommendation via the display.

In various aspects, a surgical system can be configured to provide a notification to a clinician when a specific aspect of contextual information is actionable. For example, FIGS. 19A and 19B depict a display screen 213200 including a recommendation 213202, 213202' for a clinician based on input from a situationally-aware surgical hub, such as the surgical hub 106 (FIGS. 1-3) or surgical hub 206 (FIG. 10) or surgical hub 7006 (FIG. 12). In various instances, the display screen 213200 includes a user interface overlay on the display screen 213200, which provides context-dependent recommendations. For example, the surgical system can highlight a data feed with an actionable icon to indicate that the underlying contextual information has an actionable aspect. In various instances, the recommendation feed can always be present; however, the recommendation is only emphasized when the recommendation is actionable. A recommendation can be emphasized with highlighting, flashing, and/or markings, for example. In other instances, the recommendations feed is only displayed when it includes an actionable item.

As shown in FIG. 19B, the recommendation 213202' is highlighted to indicate an elevated priority level based on an anticipated surgical act and the input from the situationally-aware surgical hub. More specifically, in FIG. 19A, a surgical device 213204 is shown in a first position, which is in a general vicinity of a diseased area 213206 of a lung 213208. In FIG. 19B, the surgical device 213204 has moved toward the diseased area 213206. Based on the trajectory of the surgical device 213204 and/or the position of the surgical device 213204, the surgical system can determine that the recommendation 213202 from FIG. 19A is now actionable and, thus, indicate the recommendation 213202' with highlighting as shown in FIG. 19B. In other words, a position change of the surgical device 213204 changes the confidence of the context-based recommendation. The increased confidence level corresponds to an elevated priority level for the recommendation 213202'.

The actionable aspect, or actionable item, can be a user-selected change in an instrument functional parameter in certain instances. For example, if friable tissue is detected by the system, the system can recommend an adjustment to protect the tissue. In one instance, the surgical system can recommend a reduction of the targeted clamping load of a stapler. Additionally or alternatively, the surgical system can recommend use of a surgical adjunct material, such as a buttress or tissue thickness compensator, for example. As another example, if the system detects comorbidity, such as the comorbidity of the patient and a mendicant, for example, that affects healing, the system can be configured to prompt or propose that the user adjust the compression wait time, utilize an adjunct, and/or utilize a reduced staple size.

In one aspect, the actionable aspect can be the automatic overlay of procedure-critical information during device placement. For example, referring again to FIGS. 19A and 19B, the display screen 213200 is configured to label and/or call-out the diseased area 213206 and/or nodules in proximity of the surgical devices. In various aspects, the automatic feature can be toggled between on and off depending on a user's preferences. Similarly, the recommendation feed can be toggled between on and off. In various instances, recommendations can only be displayed when they are actionable and/or elevated to a priority level above a predefined threshold that is preprogrammed and/or adjusted by an operator.

In one aspect, the system can be configured to highlight a data feed that has direct implications to a current surgical step or action. The relevant data within the surgical context might impact how the clinician conducts one or more of the subsequent functional tasks. For example, the data feed related to blood pressure measurements can be highlighted in certain instances, such as when the blood pressure measurement is unusually high or low. Unusually high or low blood pressure can affect how a clinician performs a transection of a large vessel with an energy device. Therefore, in various instances, when the situational awareness indicates that the clinician is preparing to perform the transection, the blood pressure data can be highlighted. As another example, the system can be configured to monitor the return path linkage to the patient. When the return path linkage is limited and a monopolar electrosurgical instrument is being utilized for dissection or mobilization, for example, the return path linkage data can be highlighted for the clinician.

In yet another example, near-infrared (NIR) fluorescence of indocyanine green (ICG) imaging can be highlighted based on actionable items determined by the situational awareness and/or context clues detected by one or more sensors at the surgical site. NIR fluorescence can be used to visualize anatomic structures, perfusion and perfusion defects as well as the lymphatic system, for example. The high penetration depth of NIR light can allow the visualization of the distribution of ICG up to a depth of 10 mm below the tissue surface. In liver surgery, the system can be used to visualize liver metastases or primary tumors of the liver. Exemplary applications include:

Visualization of perfusion, in which ischemic areas can be displayed in real-time more easily and efficiently, and/or perfusion can be examined, for instance in anastomoses, which can enable the surgeon to take intraoperative action, such as for rapid perfusion assessment of a planned resection zone, as well as of the subsequent anastomosis in a colon or esophageal resection and gastric bypass, for example, perfusion assessment of flap plasty in open surgery, visualization of liver segments, and multidisciplinary use in laparoscopic, endoscopic, and open surgery;

Visualization of the biliary tree anatomy, which can allow rapid and reliable identification of the biliary anatomy, for instance in cholecystectomy for reduced surgical duration and facilitated differentiation between cystic duct and common bile duct, as well as display of intraoperative bile leakage with ICG, such as following a partial hepatectomy, for example;

Visualization of hepatocellular carcinoma and metastases, including intraoperative visualization of metastases and hepatocellular carcinoma on or below the liver surface, diagnostics of superficial or near-surface micrometastases down to the millimeter range, easier definition of resection borders, and visualization of liver segments, for example; and Visualization of the lymphatic system, which allows real-time visualization of the entire lymphatic system draining a tumor, for example, and can avoid nuclear medicine imaging with detection rates comparing favorably with established methods of lymph node visualization, localization of lymphatic leakages, and multidisciplinary use, for instance in gynecology, urology, and general surgery.

NIR/ICG Visualization can be provided by OPALI® technology from KARL STORZ, which is described at www.karlstorz.com/ie/en/nir-icg-near-infrared-fluorescence.htm, for example. The NIR/ICG data can be emphasized or highlighted to the clinician when the visualization is important for how the surgeon performs the subsequent step based on the situational awareness and anticipated surgical steps.

In another example, a surgical system can be configured to highlight an alternative imaging or analysis system when the surgical system detects that the imaging or analysis system is detecting something relevant to the current step or current task of a surgical device. For example, the system can highlight the laser Doppler scanning array function when a dissector is about to intersect with a significant vessel or underlining structure. As another example, the system can highlight computed tomography (CT) imaging when a stapler appears to be placed within the limits of a marginal tissue area. The various recommendations to the clinician can be communicated on a display screen within the sterile field. In various instances, one or more recommendations can be further emphasized with an auditory and/or tactile indication in the sterile field, such as a verbal warning and/or beep when the recommendation is actionable and/or time-sensitive.

In various instances, a recommendation is actionable when the recommendation can be implemented within a predefined time and/or number of surgical steps. For example, a recommendation can be actionable if it should be implemented within the upcoming minutes (e.g. 1-2 minutes) of the procedure. In certain instances, a recommendation can be actionable if it should be implemented within the next 5, 10, or 30 seconds of the procedure, for example. The time frame can be determined by a clinician's reaction skills, for example. In certain instances, a first type of emphasis for the recommendation can be provided at a first time, and a second type of emphasis can be provided at a later time when the recommendation is more time-sensitive/urgent. In still other instances, the recommendation can be provided when it relates to the next surgical step expected based on the situational awareness of the clinician. In other instances, recommendations can be provided two steps before it should be implemented. The reader will appreciate that the various time-based and step-based settings for actionable recommendations can be predefined and/or adjusted by a clinician and/or operator. In certain instances, actionable recommendations can be required, such as during a surgical training session, for example. In other instances, actionable recommendations can be optional and/or customizable by the clinician.

In various aspects, a surgical system can be configured to implement a data bridge for the clinician. Various techniques for interfacing the data within the surgical hub to a display for use by a clinician are described herein. For example, intraoperative surgical data can be contributed to the implementation and tracking of post-operative care metrics.

FIG. 20 depicts a block diagram 213300 illustrating intraoperative surgical data 213302 being correlated with predicted outcomes 213304 and corresponding recommendations 213306 being provided. For example, intraoperative surgical data 213302 can be correlated with prior outcomes to determine the predicted outcomes 213304 based on the intraoperative surgical data 213302 to inform the clinician(s) about key concerns, recommendations, and potential best practices. Further, the intraoperative surgical data 213302 can be correlated to prior case history to predict outcomes of care metrics flagged by an operator or organization, such as a hospital or health system. Predicted outcomes 213304 that are based on the data correlations can include, for example, the patient's length of stay, re-admission rates, re-operation rates, time to chest tube removal, time to colon motility, and the number, type, and severity of insurance or other clinically-coded events (e.g., ICD-9 or ICD-10 codes for bleeding related complications, transfusions, and so on). Further, the intraoperative data set can, in some aspects, be comprehensive of all available primary and secondary data sources from the procedure (e.g., EMR, situational awareness learnings, video, and so on).

The block diagram 213300 refers to a Lower Anterior Resection (LAR) procedure, in which a tumor is located deep in the patient's pelvis. Firing information, which can be obtained from a video and/or various sensors, for example, indicates the margin is suboptimal, which corresponds to an increased chance of cancer reoccurrence. The firing information also indicates that significant tension is placed on the colon, which corresponds to an increased risk of leaking. Furthermore, the firing information indicates that the firing line is not perpendicular, which corresponds to an increased time to colon mobility. The intraoperative surgical data 213302 also monitors the procedure time. In the example of FIG. 20, the procedure time is characterized as "very long" with extensive dissection and significant colon manipulation. In combination, these factors also correspond to an increased chance of cancer reoccurrence. The data bridge can acquire additional data as well, such as the medications delivered and/or patient demographics, for example, which can further correspond to various predicted outcomes and/or comorbidities. Based on the various predicted outcomes 213304, the surgical hub can provide various recommendations for post-operative care, including aggressive oncology follow-up treatment, placement of a rectal drain, increased dietary restrictions, a hospital cost analysis, and an anticipated length-of-stay (LOS) can inform the hospital bed assignments and/or requirements.

In various aspects, a surgical system can be configured to detect movement, velocity, acceleration, and/or orientation of elements, such as particulate matter and/or aerosol particles, for example, within a scope's field of view (FOV). By detecting one or more of these properties, the surgical system can increase the depth of data that is extractable during a surgical procedure and/or can illuminate aspects of the surgical procedure for a clinician. For example, the system can be configured to determine active actionable events for the clinician's attention.

Properties of fluid flow at a surgical site can be an indicator of an actionable item, or adjustment, for a surgical hub and/or clinician. Fluid flow includes the flow of smoke, insufflation fluids, blood, contrast agents, and/or dye, for example. In various instances, properties of fluid flow can correspond to different surgical events, such as increased smoke generation during an energy treatment, detection of bleeding, perfusion assessment, and/or detection of a leaking anastomosis. Based on the actionable item determined by a detected property, or properties, of fluid flow, a recommendation can be provided. However, without the detection and/or monitoring of one or more properties of fluid flow, it can be difficult to determine various actionable items and corresponding recommendations.

In various instances, by detecting and/or monitoring one or more properties of fluid flow, an increased depth of data can be extracted for analysis by a surgical hub. As a result, actionable items can be identified and/or identified more expediently and corresponding recommendations can be provided and/or implemented in a timely manner. In certain instances, a surgical hub can automatically implement an adjustment and/or alert the clinician to an actionable item.

In one aspect, a surgical system comprises a sensor configured to detect a property of airborne particles in a fluid within a patient's abdominal cavity, a surgical device configured to implement a surgical function, and a control circuit comprising a processor and a memory communicatively coupled to the processor, wherein the control circuit is communicatively coupled to the sensor and the surgical device. The control circuit can be configured to receive an input signal from the sensor indicative of the property of airborne particles in the fluid and, in response to the input signal, provide an output signal to the surgical device indicative of an adjustment to the surgical function. The surgical system can be configured to detect airborne particulates and aerosols within the insufflation gases within a body (e.g., the abdomen), for example. In one aspect, the detection methods include, for example, optical, laser refractive, ultrasonic, and/or magnetic resonance. In one aspect, functional adjustments can include, for example, affecting the power level of the generator, the venting of the space, the degree of smoke evacuation, the degree of filtration, and/or application of a secondary condenser to induce condensation. In one aspect, the adjustment can result in a proportionate increase in a system that was already active, the addition of a second effect or function to the already active one, and/or the swapping out of one actuation or function for another system entirely. Various adjustments are further described herein.

Detecting one or more properties of fluid flow at a surgical site can encompass one or more measurement systems and/or methods further described herein. For example, optical measurement systems and/or ultrasonic measurement systems can be employed. Optical measurement systems include laser Doppler velocimetry (LDV) or laser Doppler flowmetry (LDF), particle image velocimetry (PIV), and/or near-infrared (NIR) fluorescence of indocyanine green (ICG), for example, which are further described herein. Ultrasonic measurement systems include non-contact pass-through ultrasound detection and non-contact reflection ultrasound detection, for example, which are also further described herein. The various techniques for detecting and/or imaging particle flow can be employed in a number of surgical uses including smoke detection and control of evacuation, aerosol and particulate differentiation, bleeding detection, perfusion assessment to identify anatomical structures, dye identification, differentiation of broken superficial surface reflection, and identification of flowing, leaking, and/or oozing fluids on a surface, for example. Various surgical uses are further described herein.

LDV, which is often referred to as LDF in a clinical or medical application, is a technique in which the Doppler shift in a laser beam is used to measure the velocity in transparent or semi-transparent fluid flows and/or the linear or vibratory motion of opaque, reflecting surfaces. In one instance, two beams of collimated, monochromatic, and coherent laser light cross in the flow of the fluid being measured. The two beams are usually obtained by splitting a single beam, thus ensuring coherence between the two beams. Lasers with wavelengths in the visible spectrum (390-750 nm) can be used, such as He—Ne, Argon ion, and/or laser diode, which allow the beam path to be observed. In other instances, wavelengths outside of the visible spectrum can be utilized, which can avoid distracting a clinician and/or interference with other imaging/visualization systems, for example. Transmitting optics focus the two beams to intersect at the focal point of the beam. The intersecting beams can interfere and generate a set of straight fringes, for example. As particles entrained in the fluid pass through the fringes, they reflect light that is then collected by a receiving optics and focused on a photodetector. The reflected light fluctuates in intensity, the frequency of which is equivalent to the Doppler shift between the incident and scattered light, and is thus proportional to the component of particle velocity that lies in the plane of the two beams. If the LDV sensor is aligned with the flow such that the fringes are perpendicular to the flow direction, the electrical signal from the photodetector is proportional to the full particle velocity. By combining three devices (e.g.; He—Ne, Argon ion, and laser diode lasers) with different wavelengths, all three flow velocity components can be simultaneously measured in various instances.

In various instances, a PIV system can be utilized to determine two-dimensional or three-dimensional vector fields for a fluid flow. PIV is an optical method of flow visualization that can be used to obtain instantaneous velocity measurements and related properties in fluids. The fluid includes tracer particles that are assumed to faithfully follow the flow dynamics of the fluid. The fluid with entrained particles is illuminated so that the particles are visible, and the motion of the particles is used to calculate speed and direction (the velocity field) of the flow. A PIV sensor can include a camera, such as a digital camera with a Charge-Coupled Device (CCD) chip, a strobe or laser with an optical arrangement to limit the physical region illuminated, such as a cylindrical lens used to convert a light beam to a line or sheet, a synchronizer to act as an external trigger for control of the camera and the laser, and seeding or tracer particles within the fluid under investigation. A fiber optic cable or liquid light guide can connect the laser to the lens setup, and PIV software can be used to post-process the optical images, for example.

In a two-dimensional PIV application, a laser light sheet of light scattering particles is illuminated through two consecutive frames, which are captured to create a two-dimensional map of particle movement and the vectors of the movement. For stereo PIV, or three-dimensional PIV, two or more cameras can be utilized at predefined angles to one another to capture the two consecutive frames and another camera can be configured to enable out-of-plane measurement. In one aspect, time-resolved particle tracking can enable the evaluation of particle tracks or paths, as well as a determination of the volume and velocity of the particles.

Surgical uses for the optical particle detection and tracking techniques and systems described herein can include, for example, smoke detection applications, bleeding detection applications, perfusion assessment applications, and dye identification applications. Various example applications are further described herein.

In one application, detection of the presence and/or concentration of smoke in an internal cavity, such as an abdomen cavity, for example, can be utilized for rate control of insufflation equipment, rate control or activation of the smoke evacuation equipment, and/or adaptation of generator algorithm parameters to minimize smoke generation. Smoke evacuation systems are further described herein.

In various instances, a surgical hub can be communicatively coupled to a smoke evacuation system. Smoke is often generated during a surgical procedure that utilizes one or more energy devices. Energy devices use energy to affect tissue. In an energy device, the energy is supplied by a generator, as further described herein. Energy devices include devices with tissue-contacting electrodes, such as an electrosurgical device having one or more radio frequency (RF) electrodes, and devices with vibrating surfaces, such as an ultrasonic device having an ultrasonic blade. For an electrosurgical device, a generator is configured to generate oscillating electric currents to energize the electrodes. For an ultrasonic device, a generator is configured to generate ultrasonic vibrations to energize the ultrasonic blade.

Many surgical systems employ a surgical evacuation system that captures the resultant smoke from a surgical procedure, and directs the captured smoke through a filter and an exhaust port away from the clinician(s) and/or from the patient(s). For example, an evacuation system can be configured to evacuate smoke that is generated during an electrosurgical procedure. The reader will appreciate that such an evacuation system can be referred to as a "smoke evacuation system" though such evacuation systems can be configured to evacuate more than just smoke from a surgical site. Throughout the present disclosure, the "smoke" evacuated by an evacuation system is not limited to just smoke. Rather, the smoke evacuation systems disclosed herein can be used to evacuate a variety of fluids, including liquids, gases, vapors, smoke, steam, or combinations thereon. The fluids can be biologic in origin and/or can be introduced to the surgical site from an external source during a procedure. The fluids can include water, saline, lymph, blood, exudate, and/or pyogenic discharge, for example. Moreover, the fluids can include particulates or other matter (e.g. cellular matter or debris) that is evacuated by the evacuation system. For example, such particulates can be suspended in the fluid. Example smoke evacuation systems, as well as various subassemblies and/or components thereof, are depicted in FIGS. 21-23. Smoke evacuation systems are further described in U.S. patent application Ser. No. 16/024,066, titled SURGICAL EVACUATION SENSING AND MOTOR CONTROL, filed Jun. 29, 2018, which is incorporated by reference herein in its entirety.

In certain instances, a processor can be located within an evacuator housing of a surgical evacuation system. For example, referring to FIG. 21, a processor 50408 and a memory 50410 therefor are positioned within an evacuator housing 50440 of a surgical evacuation system 50400. The processor 50408 is in signal communication with a motor driver 50428, various internal sensors 50430, a display 50442, the memory 50410, and a communication device 50418. The communication device 50418 can include a transceiver configured to communicate over physical wires or wirelessly. The communication device 50418 may further include one or more additional transceivers. The transceivers may include, but are not limited to cellular modems, wireless mesh network transceivers, Wi-Fi® transceivers, low power wide area (LPWA) transceivers, and/or near field communications transceivers (NFC). The communication device 50418 may include or may be configured to communicate with a mobile telephone, a sensor system (e.g., environmental, position, motion, etc.) and/or a sensor network (wired and/or wireless), a computing system (e.g., a server, a workstation computer, a desktop computer, a laptop computer, a tablet computer (e.g., iPad®, GalaxyTab® and the like), an ultraportable computer, an ultramobile computer, a netbook computer and/or a subnotebook computer; etc. In at least one aspect of the present disclosure, one of the devices may be a coordinator node.

The transceivers may be configured to receive serial transmit data via respective universal asynchronous receiver-transmitters (UARTs) from the processor 50408 to modulate the serial transmit data onto an RF carrier to produce a transmit RF signal and to transmit the transmit RF signal via respective antennas. The transceiver(s) are further configured to receive a receive RF signal via respective antennas that includes an RF carrier modulated with serial receive data, to demodulate the receive RF signal to extract the serial receive data and to provide the serial receive data to respective UARTs for provision to the processor 50408. Each RF signal has an associated carrier frequency and an associated channel bandwidth. The channel bandwidth is associated with the carrier frequency, the transmit data and/or the receive data. Each RF carrier frequency and channel bandwidth is related to the operating frequency range(s) of the transceiver(s). Each channel bandwidth is further related to the wireless communication standard and/or protocol with which the transceiver(s) may comply. In other words, each transceiver may correspond to an implementation of a selected wireless communication standard and/or protocol, e.g., IEEE 802.11 a/b/g/n for Wi-Fi® and/or IEEE 802.15.4 for wireless mesh networks using Zigbee routing.

The communication device 50418 can allow the processor 50408 in the surgical evacuation system 50400 to communicate with other devices within a surgical system. For example, the communication device 50418 can allow wired and/or wireless communication to one or more external sensors 50432, one or more surgical devices 50444, one or more hubs 50448, one or more clouds 50446, and/or one or more additional surgical systems and/or tools. The reader will readily appreciate that the surgical evacuation system 50400 of FIG. 21 can be incorporated into an intelligent electrosurgical system in certain instances. The surgical evacuation system 50400 also includes a pump 50450, including a pump motor 50451 thereof, an evacuation conduit 50436, and an exhaust 50452. Various pumps, evacuation conduits and exhausts are further described herein. The surgical evacuation system 50400 can also include a sensing and intelligent controls device. The sensing and intelligent controls device includes sensor algorithms and communication algorithms that facilitate communication between the smoke evacuation system and other devices to adapt their control programs.

The surgical evacuation system 50400 can be programmed to monitor one or more parameters of a surgical system and can affect a surgical function based on one or more algorithms stored in a memory in signal communication with a processor of a surgical hub and/or hub-connected surgical device and/or the processor 50408 within the surgical evacuation system 50400. Various exemplary aspects disclosed herein can be implemented by such algorithms, for example. For example, intelligent surgical evacuation systems and adjustment algorithms are further described in U.S. patent application Ser. No. 16/024,066, titled SURGICAL EVACUATION SENSING AND MOTOR CONTROL, filed Jun. 29, 2018, which is incorporated by reference herein in its entirety.

An electrosurgical system can include a signal generator, an electrosurgical instrument, a return electrode, and a surgical evacuation system. The generator may be an RF wave generator that produces RF electrical energy. Connected to the electrosurgical instrument is a utility conduit. The utility conduit includes a cable that communicates electrical energy from the signal generator to the electrosurgical instrument. The utility conduit also includes a vacuum hose that conveys captured/collected smoke and/or fluid away from a surgical site. Such an exemplary electrosurgical system 50601 is shown in FIG. 22. More specifically, the electrosurgical system 50601 includes a generator 50640, an electrosurgical instrument 50630, a return electrode 50646, and an evacuation system 50600. The electrosurgical instrument 50630 includes a handle 50632 and a distal conduit opening 50634 that is fluidically coupled to a suction hose 50636 of the evacuation system 50600. The electrosurgical instrument 50630 also includes an electrode that is powered by the generator 50640. A first electrical connection 50642, e.g., a wire, extends from the electrosurgical instrument 50630 to the generator 50640. A second electrical connection 50644, e.g., a wire, extends from the generator 50646 to an electrode, i.e., the return electrode 50646. In other instances, the electrosurgical instrument 50630 can be a bipolar electrosurgical instrument. The distal conduit opening 50634 on the electrosurgical instrument 50630 is fluidically coupled to the suction hose 50636 that extends to a filter end cap 50603 of a filter that is installed in an evacuator housing 50618 of the evacuation system 50600.

In other instances, the distal conduit opening 50634 for the evacuation system 50600 can be on a handpiece or tool that is separate from the electrosurgical instrument 50630. For example, the evacuation system 50600 can include a surgical tool that is not coupled to the generator 50640 and/or does not include tissue-energizing surfaces. In certain instances, the distal conduit opening 50634 for the evacuation system 50600 can be releasably attached to an electrosurgical tool. For example, the evacuation system 50600 can include a clip-on or snap-on conduit terminating at a distal conduit opening, which can be releasably attached to a surgical tool.

The electrosurgical instrument 50630 is configured to deliver electrical energy to target tissue of a patient to cut the tissue and/or cauterize blood vessels within and/or near the target tissue, as described herein. Specifically, an electrical discharge is provided by the electrode tip to the patient in order to cause heating of cellular matter of the patient that is in close contact with or adjacent to electrode tip. The tissue heating takes place at an appropriately high temperature to allow the electrosurgical instrument 50630 to be used to perform electrosurgery. The return electrode 50646, or return pad, can be placed under the patient during the surgical procedure, in order to complete the circuit and provide a return electrical path to the generator 50640 for energy that passes into the patient's body.

The heating of cellular matter of the patient by the electrode tip, or cauterization of blood vessels to prevent bleeding, often results in smoke being released where the cauterization takes place, as further described herein. In such instances, because the evacuation conduit opening 50634 is near the electrode tip, the evacuation system 50600 is configured to capture the smoke that is released during a surgical procedure. Vacuum suction may draw the smoke into the conduit opening 50634, through the electrosurgical instrument 50630, and into the suction hose 50636 toward the evacuator housing 50618 of the evacuation system 50600. In various instances, the electrosurgical system 50601 and/or the evacuation system 50600 can include a control circuit including a processor and memory, as described herein with respect to the control schematic in FIG. 21.

Referring now to FIG. 23, another evacuator housing 50918 for an evacuation system 50900 is depicted. The evacuator housing 50918 defines a flow path 50904 between an inlet 50922 to the evacuator housing 50918 and an outlet 50924 to the evacuator housing 50918. Intermediate the inlet 50922 and the outlet 50924, a fluid trap 50960, a filter 50970, and a pump 50906 are sequentially arranged. The evacuator housing 50918 can include a socket or a receptacle 50971 dimensioned to receive a modular fluid trap and/or a replaceable filter 50970. At a diverter valve 50934, fluid can be directed into a condenser 50935 of the fluid trap 50960 and the smoke can continue toward the filter 50970. In certain instances, the fluid trap 50960 can include baffles, such as the baffles 50964, and/or splatter screens, such as the screen 50962, for example, for preventing the captured fluid from splashing out of the fluid trap 50960. The filter 50970 includes a pleated ultra-low penetration air (ULPA) filter 50942 and a charcoal filter 50944. A sealed conduit or tube 50905 extends between the various in-line components. The evacuator housing 50918 also includes sensors 50830, 50832, 50836, 50838, 50840, 50846, 50848, 50850, 50852, and 50854 which are further described herein and in U.S. patent application Ser. No. 16/024,066, titled SURGICAL EVACUATION SENSING AND MOTOR CONTROL, filed Jun. 29, 2018, which is incorporated by reference herein in its entirety.

Referring still to FIG. 23, the evacuator housing 50918 also includes a centrifugal blower arrangement 50980 and a recirculating valve 50990. The recirculating valve 50990 can selectively open and close to recirculate fluid through the fluid trap 50960. For example, if the fluid detection sensor 50836 detects a fluid, the recirculating valve 50990 can be opened such that the fluid is directed back away from the filter 50970 and back into the fluid trap 50960. If the fluid detection sensor 50836 does not detect a fluid, the valve 50990 can be closed such that the smoke is directed into the filter 50970. When fluid is recirculated via the recirculating valve 50990, the fluid can be drawn through a recirculation conduit 50982. The centrifugal blower arrangement 50980 is engaged with the recirculation conduit 50982 to generate a recirculating suction force in the recirculation conduit 50982. More specifically, when the recirculating valve 50990 is open and the pump 50906 is activated, the suction force generated by the pump 50906 downstream of the filter 50970 can generate rotation of the first centrifugal blower, or first squirrel cage, 50984, which can be transferred to the second centrifugal blower, or second squirrel cage, 50986, which draws the recirculated fluid through the recirculating valve 50990 and into the fluid trap 50960.

In various aspects of the present disclosure, the control schematics of FIG. 21 can be utilized with the various surgical systems, evacuation systems, sensor systems and evacuator housings of FIGS. 22 and 23.

Smoke evacuated from a surgical site can include liquids, aerosols, and/or gases, and/or can include material of different chemical and/or physical properties, such as particulate matter and particles of different sizes and/or densities, for example. The different types of materials evacuated from a surgical site can affect the efficiency of the surgical evacuation system and the pump thereof. Moreover, certain types of material can require the pump to draw excessive power and/or can risk damaging the motor for the pump.

The power supplied to the pump can be modulated to control the flowrate of smoke through the evacuation system based on input from one or more sensors along the flow path. Output from the sensors can be indicative of a state or quality of the smoke evacuation system and/or one or more properties of the evacuated smoke such as the type(s) and ratios of matter, chemical properties, density, and/or size of particulates, for example. In one aspect of the present disclosure, a pressure differential between two pressure sensors in the evacuation system can indicate the state of the region therebetween such as the state of a filter, a fluid trap, and/or the overall system, for example. Based on the sensor input, an operational parameter of the motor for the pump can be adjusted by changing the current supplied to the motor and/or the duty cycle, which is configured to change the motor speed.

In one aspect of the present disclosure, by modulating the flowrate of smoke through the evacuation system, the efficiency of the filter can be improved and/or the motor can be protected from burnout.

A surgical evacuation system can include one or more particle counters, or particle sensors, for detecting the size and/or concentration of particulate within the smoke. Referring again to FIG. 23, the particle sensors 50838 and 50848 are depicted. The reader will readily appreciate that various particle measurement means are possible. For example, a particle sensor can be an optical sensor, a laser sensor, a photoelectric sensor, an ionization sensor, an electrostatic sensor, and/or combinations thereof. Various particle sensors are further described herein.

In various instances, the speed of the motor and, thus, the speed of the pump can be adjusted based on the particulate concentration detected by the one or more particle sensors in a surgical evacuation system. For example, when the particle sensor(s) detect an increased concentration of particulate in the flow path, which can correspond to an increased quantity of smoke in the flow path, the speed of the motor can be increased to increase the speed of the pump and to draw more fluid into the smoke evacuation system from the surgical site. Similarly, when the particle sensor(s) detects a decreased concentration of particulate in the flow path, which can correspond to a decreased quantity of smoke in the flow path, the speed of the motor can be decreased to decrease the speed of the pump and to reduce suction from the surgical site. Additional and alternative adjustment algorithms for the surgical evacuation system are further described herein. Moreover, in certain instances, based on the sensor data from the smoke evacuation system, a generator in the surgical system can be controlled to adjust the amount of smoke generated at the surgical site, as further described herein.

In addition to particle sensors positioned along the flow path of the surgical evacuation system, the system can include one or more sensors for detecting the particulate concentration in the ambient room, for example, in the operating room or surgical theater. Referring again to FIG. 23, the air quality particle sensor 50852 is installed on an external surface of the evacuator housing 50918. Alternative locations for the air quality particle sensor 50852 are also envisioned.

In at least one instance, a particle sensor can be positioned downstream of the filter and, in certain instances, can be positioned at or near the outlet of the filter. For example, the particle sensor 50848 is positioned downstream of the filter 50970 and the pump 50906 in the smoke evacuation system 50900. Because the particle sensor 50848 is positioned downstream of the filter(s) 50970, the particle sensor is configured to confirm that the filter(s) 50970 have removed sufficient particulate from the smoke. In various instances, such a sensor can be adjacent to the exhaust outlet 50924 of the evacuator housing 50918. In one aspect of the present disclosure, an electrostatic particle sensor can be utilized. For example, the exhaust outlet 50924 can include an electrostatic particulate sensor that the exhaust flows past downstream of the filtration system and prior to being exhaust into the surgical theater.

The particulate concentration detected by one or more sensors of the surgical evacuation system can be communicated to a clinician in a number of different ways. For example, the evacuator housing 50918 and/or the evacuation device can include an indicator, such as one or more lights and/or display screens. For example, an LED on the evacuator housing 50918 may change color (e.g. from blue to red)

depending on the volume of particulate detected by the sensor(s). In other instances, the indicator can include an alarm or warning, which can be tactile, auditory, and/or visual, for example. In such instances, when the particulate concentration in the ambient air detected by the air quality sensor (e.g. the particle sensor 50852) exceeds a threshold amount, the clinician(s) in the surgical theater can be notified by the indicator(s).

In certain instances, a surgical evacuation system can include an optical sensor. The optical sensor can include an electronic sensor that converts light, or a change in the light, into an electronic signal. The optical sensor can utilize a light scattering method to detect and count particles in the smoke to determine the concentration of particles in the smoke. In various instances, the light is laser-based. For example, in one instance, a laser light source is configured to illuminate particles as the particles move through a detection chamber. As the particles pass through the laser's beam, the light source is refracted, obscured, redirected, and/or absorbed. The scattered light is recorded by a photo detector, and the recorded light is analyzed. For example, the recorded light can be converted to an electrical signal indicative of the size and quantity of the particles, which corresponds to the particulate concentration in the smoke. The particulate concentration in the smoke can be calculated in real-time by a laser optical sensor, for example. In one aspect of the present disclosure, at least one of the particle sensors 50838, 50848, 50852 are laser optical sensors. Various alternative sensing techniques and sensor arrangements are further described herein and in U.S. patent application Ser. No. 16/024,066, titled SURGICAL EVACUATION SENSING AND MOTOR CONTROL, filed Jun. 29, 2018, which is incorporated by reference herein in its entirety.

Based on the presence and concentration of smoke in an abdomen cavity, the generator algorithm for minimizing or controlling the smoke generation can be adapted. For example, information/knowledge gained from previous surgical events, such as an earlier firing and/or energy activation, can be used to adjust one or more parameters of a generator control algorithm. Referring now to FIG. 24, a series of graphs 213400, 213402, and 213404 are depicted in which particle count 213406, fan speed 213408, and energy device power 213410 are shown relative to time (t). The particle count 213406 can be detected with the various sensors and/or detection techniques disclosed herein. One or more surgical functions and/or one or more devices can be adjusted in response to the detected particle count 213406, which corresponds to the smoke concentration at the surgical site (e.g. in an internal cavity of the patient). Additionally, the type and/or degree of adjustment can depend on knowledge gained during previous firings and/or activations.

The energy device power 213410 is provided during a first activation 213412 from time $t_0$ to time $t_2$ and during a second activation 213414 from time $t_5$ to time $t_7$. Knowledge gained during the first activation 213412 can be utilized to adjust the control algorithm of a control circuit applied during the second activation 213414. The control circuit can be encompassed in a surgical hub and/or smoke evacuator as depicted in the control schematic of FIG. 21, for example Referring still to FIG. 24, when the energy device is activated for the first activation 213412, the energy device power 213410 is set to a predefined power level 213430, and the particle count 213406 begins to increase toward a first threshold 213416. The predefined power level 213430 can be a clinician-selected power level. For example, the predefined power level 213430 can be preprogrammed on the surgical device and/or at the surgical hub. In certain instances, the surgical device can be configured to operate at different predefined power levels depending on the actuators and/or control buttons activated by the clinician.

At time $t_1$, as the first activation 213412 continues, the particle count 213406 increases above the first threshold 213416 to a peak value 213418 at time $t_2$ when the first activation 213412 ends. In response to the particle count 213406 exceeding the first threshold 213416 at time $t_1$, a control circuit in signal communication with the smoke evacuator, is configured to implement a first adjustment 213420. For example, the control circuit is configured to increase the fan speed 213408 from a low setting 213426 to a high setting 213428.

After the first activation 213412 ends at time $t_2$, the particle count 213406 can begin to decrease from the peak value 213418; however, the smoke evacuator can continue to operate at the high setting 213428 until time $t_3$ when the particle count 213406 drops below the first threshold 213416. In response to the particle count 213406 decreasing below the first threshold 213416, the fan speed 213408 can be decreased to the low setting 213426 and, in various instances, can be turned off when the particle count 213406 drops to zero at time $t_4$. In other instances, the smoke evacuator can include additional speeds which can correspond to additional particle count thresholds and/or can be scaled in proportion to the particle count 213406, for example. In various instances, the smoke evacuator can operate at a ultra-low setting and/or cycle on-and-off when in a sleep or resting mode when the particle count is zero and/or below a minimum threshold value.

At time $t_5$, when the second activation 213414 is initiated, the particle count 213406 again begins to increase and the fan speed 213408 can be set at the low setting 213426 to extract the smoke from the surgical site. In various instances, before any smoke is detected, the smoke evacuator can be activated in response to an activation of the energy device. As shown in FIG. 24, in certain instances, the particle count 213406 can continue to increase during the second activation 213414 while the fan speed 213408 is set to the low setting 213426 and, at time $t_6$, as the second activation 213414 continues, the particle count 213406 again increases above the first threshold 213416. If the control circuit were to implement the first adjustment 213420 again, the particle count 213406 would again follow the hypothetical curve 213424 to the peak value 213418 at time $t_7$ when the second activation 213414 ends. However, in response to the particle count 213406 again exceeding the first threshold 213416 at time $t_6$ in the second activation 213416, the control circuit is configured to adapt the control algorithm and implement a second adjustment 213422 that is different than the first adjustment 213420.

For example, in addition to increasing the fan speed 213408 from the low setting 213426 to the high setting 213428 at time $t_6$, the control circuit is configured to decrease the energy device power 213410 below the predefined power level 213430. For example, the control actuated by the clinician can correspond to the predefined power level 213430; however, a control circuit for the surgical hub can adjust the energy device power 213430 to an adjusted power level 213432. The adjusted power level 213432 in FIG. 24 is less than the predefined power level 213430. In other instances, the hub-controlled adjustment can increase the energy device power 213410 and/or otherwise adjust the energy device power, such as by applying pulses of varying duration and/or frequency (e.g. pulse width modulation and/or pulse frequency modulation) and/or adjusting the energy modality, for example.

The second adjustment 213422 can be learned or developed based on the system's response to the first adjustment 213420. For example, if the peak value 213418 obtained when implementing the first adjustment 213420 is still considered to be too high and/or associated with undesirable consequences, such as obstructing the clinician's view and/or interfering with the application of energy to tissue, for example, the control circuit can seek a different adjustment. As described herein, the second adjustment 213422 includes the first adjustment 213422 (i.e. adjusting the fan speed 213408 from the low setting 213426 to the high setting 213428) and the additional adjustment to the energy device power 213410. In other instances, the second adjustment 213422 can replace the first adjustment 213420.

In certain instances, the second adjustment 213422 can adjust a threshold and/or degree of the first adjustment 213420. For example, the second adjustment 213422 can include increasing the fan speed 213408 to a level that is greater than the high setting 213428. In various instances, the second adjustment 213422 can include a modification to the first adjustment 213420 that is proportional to a desired effect. For example, if the first adjustment 213410 increased the fan speed 213408 by 10% and obtained a 10% reduction in smoke concentration, the second adjustment 213422 could be a 15% reduction in fan speed 213408 to obtain a desired 15% reduction in smoke concentration.

The first and second adjustments described herein are example adjustments. Adjustments can include changing the power level of a generator, power level of a smoke evacuator, venting of a space, and degree and/or type of filtration and/or condensation-induction in a smoke evacuation system, for example.

As described herein, the techniques for improved identification and tracking of particles, which can determine the directionality and velocity of a fluid, for example, can be utilized in various surgical applications. For example, the improved techniques can be used for smoke detection applications, as further described herein. Additionally or alternatively, based on the directionality and/or velocity of the smoke, the surgical system can be configured to adjust the smoke evacuation motor control to clear the smoke more quickly and then slow down to minimize noise in the operating room (OR). As another example, the system can increase insufflation recirculation to evacuate the particulate away from the active field of operation. For example, if a sensor detects the smoke moving toward a treatment region where a clinician is actively working and/or treating, it can be desirable to increase the circulation within the cavity to quickly move the obstructing particulate (i.e. smoke) away from the treatment region.

In one application, improved techniques for the identification and tracking of particles can be utilized for bleeding detection. Based on the directionality and velocity of the flow, the control circuit and/or surgical hub can determine and/or recommend a subsequent step to address the bleeding. In another application, the improved techniques for identification and tracking of particles can be utilized for perfusion assessment in tissue. Perfusion assessment can be utilized to identify anatomical structures, for example. In one example, NIR illumination of ICG can be used to image perfusion in a lung segment. Visualization of such perfusion can be used to identify/demarcate an intersegmental plane for segmentectomy procedures, for example. Thereafter, the control circuit and/or surgical hub can determine and/or recommend a subsequent step. For example, the control circuit and/or surgical hub can recommend a particular surgical device and/or location. In certain instances, the control circuit and/or surgical hub can guide the surgical device to the desired location.

In one application, the improved techniques for the identification and detection of particles can be used with migration of dye, which can enable the system to highlight a leak path. The size and location of the leak can be determined, for example. In one instance, when leak testing an anastomosis, a leak path may be identified from the colon into the abdomen. In various instances, the identification of a leak path can inform the clinician's decision-making process. For example, a recommendation regarding how and/or when to address the leak path can be provided to the clinician. In certain instances, contextual information provided by the hub can affect the recommendation provided to the clinician. Contextual information can indicate the probability of a functional leak taking into account the current pressure within the colon dye fluid, the viability of the tissue from computerized topography (CT) imaging and/or instrument manipulation forces, and/or patient-specific complicating factors, which can be identified in an electronic health record (EHR), for example. The recommendation can include suggestions for viable products to reinforce the anastomosis based on the identification of detected implications (e.g., the size of leak, the location of the leak with respect to "dog ears" or lateral intersection margins/stapled corners, and/or compression loads detected in the circular stapler). Additionally or alternatively, the recommendations can include the proposal of an overlaying of reinforcement agents like fibrin, thrombin, and/or oxidized regenerated cellulose (ORC), for example. Additionally or alternatively, the recommendations can include a proposal to over-sew or re-staple a portion of the line due to tissue tension or collateral blood supply issues, for example.

In various instances, the detection of one or more properties of fluid flow at a surgical site can encompass one or more of the various measurements systems and/or techniques further described herein. For example, optical measurement systems, such as laser Doppler velocimetry (LDV) or laser Doppler flowmetry (LDF), particle image velocimetry (PIV), and/or near-infrared (NIR) fluorescence of indocyanine green (ICG), for example, can be utilized. In other instances, instead of a camera/optical measurement system, detection and/or measurements can utilize an alternative sensing array to track particles. For example, ultrasonic measurements systems, such as non-contact pass-through ultrasound detection and non-contact reflection ultrasound detection, for example, can be utilized.

In one aspect, non-contact pass-through ultrasound can be utilized for particle detection. Referring to an ultrasonic pass-through particle detection system 213500 in FIG. 25, an ultrasound emitter 213502 can be positioned within the patient's body (e.g. within an abdominal cavity) similar to an optical scope. In various instances, the emitter 213502 can be positioned on a distal end of a scope 213501 for an imaging system. The scope can include a camera that views the surgical site and transmits the view(s) to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. In other instances, the emitter 213502 can be a separate and distinct device from a scope. The ultrasound emitter 213502 is configured to transmit a curtain of homogeneous sound, which passes through a fluid 213504 (e.g. moving particles such as smoke particulate and/or steam aerosols) and is received on the opposite side of the fluid 213504 by a receiver 213506. The receiver 213506 can be positioned on a surgical device, such as an end effector and/or a distal nose of a staple cartridge 213508 received within an elongate channel of an end effector, for example. In other instances, the receiver 213506 can be positioned on a separate and distinct surgical tool. As various sound waves pass from the emitter 213502 through the fluid 213504, certain waves can be blocked by the fluid 213504. Based on the sound waves received by the receiver 213506, the ultrasonic pass-through particle detection system 213500 is configured to determine the Doppler shift, i.e., the speeding up or slowing down of the sound waves, which corresponds to the properties of the fluid's flow.

Surgical uses for the ultrasonic pass-through particle detection system 213500 include, for example, smoke detection applications and control of evacuation, including detection of the velocity, directionality, and concentrations of particulates in the flow and detection of flow patterns and/or dispersion rates, for example. Surgical uses also include the differentiation between aerosol particles and particulates (e.g. distinguishing smoke from steam). Such distinctions can be helpful when adjusting a smoke evacuation system, such as changing the fluid flow path to address aerosols within the flow path, which may damage a particulate matter filter if not properly extracted, for example. Additional surgical applications for particle detection and monitoring, such as ultrasound techniques utilizing the ultrasonic pass-through particle detection system 213500, for example, are further described herein. Moreover, a surgical system and/or control circuit therefor can be configured to utilize information from such an ultrasonic pass-through particle detection system to adjust and/or suggest a surgical function during a surgical procedure.

In one aspect, non-contact reflection sound detection can be utilized for particle detection. Referring now to FIG. 26, an ultrasonic reflection particle detection system 213600 is shown. Similar to the ultrasonic pass-through technique described above with respect to FIG. 25, the ultrasonic reflection particle detection system 213600 includes an emitter, or transmitter/sound source, 213602 and a receiver 213606. However, this ultrasonic reflection particle detection system 213600 differs from the ultrasonic pass-through particle detection system 213500 in that the emitter 213602 and the receiver 213606 are co-located on the same surgical device 213608. In other instances, the emitter 213602 and the receiver 213606 can be positioned on separate devices but located adjacently to one other. In various instances, the surgical device 213608 can be a scope like the device 213502 (FIG. 25), for example.

The ultrasonic reflection particle detection system 213600 is configured to detect reflected sound waves. The reflection and refraction of the sound waves will depend on the surface properties of the tissue T that the surgical device 213608 is targeting. Since the surgical device 213608 is not in contact with the tissue T, it is configured to sense the superficial aspects of the tissue T, e.g. the surface features of the tissue T and not properties/features deep within the tissue T. For example, referring to the flowchart 213650 in FIG. 27, data from the emitter 213602 and the receiver 213606 regarding the sound wave properties is obtained at block 213652 and provided to a control circuit for analysis at block 213654. The control circuit is configured to determine tissue surface information at block 213656. Various control circuits for receiving input signals, calculating tissue surface information, and providing outputs can be incorporated into the various control circuits described herein. For example, algorithms for determining the tissue surface information from the input signals can be stored in the memory of the various control circuits described herein.

Surgical uses for the ultrasonic reflection particle detection systems include, for example, differentiation of broken superficial surface reflection and the detection of flowing or oozing fluids on a tissue surface. For example, sound reflection that indicates broken or interrupted superficial tissue features can be used to detect unhealthy tissue features, such as infection, adhesions, scarring, remodeling, and cancer. Such tissue features can correspond to a tissue surface that is more interrupted and, thus, that causes increased refraction and dampening of the ultrasound waves in comparison to healthy tissue, which typically defines a continuous, uninterrupted surface. Flowing or oozing fluids on the surface of the tissue can also create different Doppler effects on the sound waves that are directed toward the surface while producing a sound reflection that is different than the reflection for a solid tissue surface. Furthermore, the more fluid that is present, the greater the sound absorption that the fluid can induce due to absorbing a portion of the energy of the sound wave. Additionally, Doppler effects on the sound wave would result in a Doppler wave shift in the sound wave depending on whether the fluid is moving towards or away from the transmitter and receiver. Directionality of the fluid flow can be detected. In various instances, varying the range of frequencies emitted by the transmitter would allow the system to further refine the surface tension, modulus, and or viscosity of the detected fluid, for example. A surgical system or control circuit therefor can be configured to utilize information from such an ultrasonic reflection particle detection system to adjust and/or suggest a surgical function during a surgical procedure.

In various aspects, the system can be configured to monitor the material in the flow being removed/evacuated from the abdomen by a smoke evacuation system or filtered and replaced by an irrigation/insufflation system, for example, with the various techniques described herein for the identification and detection of particles along a flow path. In certain instances, the system can be configured to detect particles within the extracted gasses and directly measure their flow rate. In one aspect, an ultrasonic pass-through array can be placed at a crossing between the passage that is extracting the insufflation gasses or filtering the insufflation gasses, for example. Such an array can be configured to detect particles passing through and, thus, can be used to determine the type and concentration of the particles flowing therethrough. An alternative to the ultrasonic pass-through array is a laser counter array which can be placed similarly. The laser counter array can measure a blocked laser light wave passing from one side of the passage to the other or the refraction of light off of the particles.

In various instances, vortex-shedding can be used in combination with either the ultrasonic pass-through array or laser counter array, described above. Vortex-shedding is configured to detect the size of the particles and their flow rate, rather than merely using the presence or concentration of the particles given a predefined flow rate. When utilizing a vortex-shedding flowmeter, there are no moving parts or elements within the flow that are necessary to measure the flow. Advantageously, this can improve the ability to clean the detection system and reuse it, and/or can minimize the buildup of bodily fluids within the detection system, for example.

Control Through Surgical Barriers

In various instances, digital surgical devices can be controlled through one or more surgical barriers. Surgical barriers include physical sterile barriers, intangible sterile barriers, and the walls of a patient's body. In one aspect, a first operating room system located within a sterile field can be indirectly commanded and controlled through the use of a second operating room system, which can have a primary operating mode and a secondary operating mode, which is designed for interacting with the first operating room system to provide commands and control. For example, in the primary operating mode, the second operating room system can effect a primary surgical function. In the secondary operating mode, the primary surgical function can be disabled. Moreover, in the secondary operating mode, the second operating room system can command and control the first operating room system. For example, a surgical instrument can be configured to effect tissue in the first operating mode and to command and control an imaging system and/or a display thereof in the second operating mode.

In certain instances, a clinician may want to provide input to a remote surgical system and/or to a surgical hub communicatively coupled to the remote surgical system from within the sterile field. For example, a clinician holding a first operating room system (e.g. a surgical device) may want to provide commands or inputs to another operating room system (e.g. an imaging or visualization system and/or display thereof) positioned outside the sterile field. In certain instances, it can be desirable to utilize the first operating room system to communicate or interact with the other operating room system through a surgical barrier, such as the boundary of the sterile field and/or a patient's body.

To facilitate such an interaction, the first operating room system can include a plurality of operating modes including a primary mode and a secondary mode. The first operating room system can switch between operating modes to selectively interact with the second operating room system. In such instances, the clinician can interact with the second operating room system without handing off or setting down the first operating room system and/or without removing the first operating room system from the surgical site.

For example, a surgical system can include a first device comprising a first control circuit and a second device configured to effect a surgical function, wherein the second device comprises a second control circuit in signal communication with the first control circuit, and wherein the second control circuit is configured to selectively toggle the second device between a secondary operating mode, in which the second device is configured to indirectly control the first device, and a primary operating mode, in which the second device is configured to control the surgical function. Each control circuit can include a processor and a memory communicatively coupled with the processor, wherein the memory stores instructions executable by the processor to receive an input signal. In response to the input signal, the second control circuit can switch between the primary operating mode and the secondary operating mode. In the primary operating mode, the second control circuit can actuate a surgical function, for example. When in the secondary operating mode, the second control circuit can control a display screen, for example. In various instances, a non-tangible computer readable medium can store computer readable instructions which, when executed, causes a surgical device to receive an input signal. In response to the input signal, the second control circuit can switch between the primary operating mode and the secondary operating mode. In the primary operating mode, the second control circuit can actuate a surgical function, for example. When in the secondary operating mode, the second control circuit can control a display screen, for example.

In one aspect, a surgical device can interface with a primary display to adjust and/or control the primary display. For example, the primary display can be controlled through a visual interface using a secondary control function of the surgical tool. Stated differently, the surgical device can be depicted on the primary display and can act as a cursor or indicator on the display to interact with a user interface of the display. Moreover, inputs to the surgical device can be inputs to the display and/or a surgical hub including the display. In such instances, the surgical device can be an input device for an interaction technique, user interface technique or input technique, which uses a combination of hardware and software to allow a computer (or control circuit thereof) to perform a task. The output can be displayed on the primary display and/or communicated to a surgical hub, as output resulting from a mouse click and/or selection provides an input command, which can be displayed or otherwise communicated via a computer monitor, for example.

Referring to FIGS. 28-30, a surgical system 214000 includes a surgical device 214002 and a display screen 214004. The display screen 214004 (FIG. 28) can be incorporated into an imaging system. For example, the imaging system can include an endoscope housing an endoscopic camera and the display screen 214004, which is configured to display the images obtained by the endoscopic camera. An endoscope is further described in U.S. patent application Ser. No. 11/277,290, titled DISPOSABLE ENDOSCOPE DEVICES, filed Mar. 23, 2006, now U.S. Patent Pub. No. 2007/0225556, which is incorporated by reference herein in its entirety. Reusable endoscopes are also contemplated.

In various instances, the display screen 214004 can be a video monitor, which is operably configured to display a live-feed of images from the surgical site. The display screen 214004 can depict a live, real-time video of the surgical site during a surgical procedure. Additionally or alternatively, the display screen 214004 can be configured to display an augmented reality view of the surgical site. For example, the display screen 214004 can depict hidden anatomical structures and/or hidden surgical devices. Such an augmented reality view can be toggled on and off, for example. The display screen 214004 also includes a graphical user interface. An operator can interact with the graphical user interface to provide input commands or controls to the display system and/or a surgical system communicatively coupled to the display system, as further described herein.

The surgical device 214002 is a handheld surgical instrument including a handle 214006, an elongate shaft 214008 extending distally from the handle 214006, and an end effector 214010 extending distally from the elongate shaft 214008. The end effector 214010 is configured to effect tissue. In one instance, the handheld surgical device can be an ultrasonic device. In such instances, the end effector 214010 can include an ultrasonic blade. A clamp arm can be positioned opposite the ultrasonic blade to facilitate clamping of tissue against the ultrasonic blade in various instances. Additionally or alternatively, the end effector 214010 can include tissue-contacting electrodes that are configured to deliver RF current to the tissue. In certain instances, the end effector 214010 can include a reciprocating knife, stapler, clip applier, and/or grasper, for example. In certain instances, the surgical device 214002 can include a housing that can be releasably coupled to a robotic arm. In such instances, the surgical device 214002 can be controlled by a clinician at a surgeon's console for the robotic surgical system.

The surgical device 214002 is configured to switch between a first mode and a second mode. The first mode can be an operational mode in which the surgical device 214002 is configured to perform a surgical function. For example, in the first mode, the surgical device 214002 can be configured to apply vibrational energy to tissue. The second mode can be a cursor mode or control mode, in which the surgical device 214002 can be configured to provide inputs to the display screen 214004. The inputs can be configured to adjust the information displayed on the display screen 214004 and/or provide inputs to a connected surgical system, such as a surgical hub like the surgical hubs 106 and 206 (FIGS. 1-11), the surgical hub 7006 (FIGS. 12 and 13), and the surgical hub 5104 (FIG. 14), for example.

Referring primarily to FIG. 29, the surgical device 214002 extends through a surgical barrier 214012 into the surgical site. The surgical barrier 214012 is an anatomical wall of a patient. The surgical device 214002 can also extend through a sterile field boundary that forms another surgical barrier. At the surgical site, an imaging system is configured to obtain views of the surgical site and the surgical device 214002. For example, a distal portion of the surgical device 214002, i.e. the grasping tips/jaws of the end effector 214010 and a portion of the shaft 214008, appear on the display screen 214004. In a first mode, the end effector 214010 can perform a surgical function, such as engaging, effecting, and/or treating tissue. The first mode can be considered a primary mode in that the end effector 214010 is performing its primary function as a surgical tool (e.g. a grasper can grasp tissue, an energy device can apply energy to tissue, a stapler can staple tissue, and so on). In the primary mode, the end effector 214010 is configured to directly effect tissue.

The end effector 214010 can toggle or switch between the primary mode and the second mode, which can be referred to as a secondary mode. The selected mode can be displayed on the display screen 214004. For example, the display screen 214004 in FIG. 28 shows a cursor mode icon 214052 to indicate that the end effector 214010 is acting as a cursor in a secondary mode. In the secondary mode, the end effector 214010 can be used to interact with the display screen 214004 and indirectly control the visualization system or a surgical system communicatively coupled thereto. The end effector 214010 shown on the display screen 214004 can function as a pointer or cursor for the graphical interface shown on the display screen 214004. In such instances, the clinician does not have to take his or her hands off of the surgical device 214002 or remove the surgical device 214002 from the patient's body to engage the display screen 214004 and provide input to the display screen 214004. In various instances, the camera of the imaging device (e.g. a laparoscopic camera) can be configured to track movement of the surgical devices at the surgical site. For example, the camera can scan or otherwise adjust its field of view to follow one or more surgical devices (or portions thereof) around the surgical site. In various instances, the clinician can select which surgical device(s) and/or portion(s) thereof are tracked by the camera. In such instances, the camera can track the end effector 214010, which can ensure the end effector 214010 is depicted on the display screen 214004 when the surgical device 214002 is in the secondary mode.

In the secondary mode, the surgical device 214002 can be used as an input device like a computer mouse or joystick, for example, to move a cursor around the interface on the display screen 214004 to manipulate the functions shown on the display screen 214004. When the displayed portion of the device is utilized as a cursor, the device tip (i.e., "cursor") can press buttons on the display screen 214004, and drag and drop display items, circle and/or highlight a portion of the video (e.g., point out the tumor or unique anatomical features) to be referenced later. For example, the device tip can select a home screen icon 214040 to return to a home screen, a play icon 214042 to play a video of the surgical procedure obtained by an endoscope, a pause icon 214044 to pause the video, a rewind icon 214046 to re-watch or replay a portion of the video, a record icon 214048 to record a new portion of the surgical procedure, and/or a setting icon 214050 to adjust a setting and/or view on the display screen 214004. In one aspect, activating the secondary mode (or cursor control mode) can change the way the tool functions while in this mode. For example, button(s), trigger(s) and/or other actuator(s) can have different functions in different modes.

The operating mode of the surgical device 214002 can be selected by the clinician. For example, the clinician can selectively toggle or switch the surgical device 214002 between the primary mode and the secondary mode. In one instance, the secondary mode can be activated by a voice command. In another instance, a tactile action by a clinician can activate the secondary mode. Referring primarily to FIG. 30, the surgical device 214002 includes a manual switch 214018, which can enable the clinician to switch between operating modes. A first position of the manual switch 214018 can correspond to the primary mode, and a second position of the manual switch 214018 can correspond to the secondary mode. The clinician can move the manual switch 214018 to toggle the surgical device 214002 between operating modes.

In one example, the surgical device 214002 is an ultrasonic surgical instrument like the HARMONIC ACE® shears by Ethicon Endo-Surgery, LLC. Such an ultrasonic surgical instrument can include a plurality of input actuators, such as maximum and minimum power buttons 214020 and 214022. The maximum power button 214020 can generate ultrasonic energy at a first energy level, or within a first range, in the primary mode, and the minimum power button 214022 can generate ultrasonic energy at a second energy level, or in a second range, in the primary mode. The second energy level, or second range, can be less than the first energy level, or first range. In various instances, the buttons 214020, 214022 can define a range of positions corresponding to different levels and/or can detect the operator's force and adjust the energy level accordingly. For example, at least one of the buttons 214020, 214022 can define a rotary element to scroll between levels and/or selections, similar to a rotary wheel on a computer mouse, for example.

In the secondary mode, the ultrasonic sealing and cutting function can be disabled and the maximum and minimum power buttons 214020 and 2104022 on the surgical device 214002 can act like buttons of a computer mouse. The clinician can point the tip of the surgical device 214002 (as displayed on the display screen 214004) at something displayed on the display screen 214004 and the buttons can then interact with the display screen 214004, as described above. The dual-button input features of the surgical device 214002 can be intuitive to a clinician familiar with a two-button computer mouse, for example. In various instances, the two-buttons can be used to select icons, drag and drop icons, and/or adjust and interact with various features of the display screen 214004, as further described herein.

In various instances, the display screen 214004 is communicatively coupled to a surgical hub, such as the surgical hubs 106 or 206 (FIGS. 1-11), the surgical hub 7006 (FIGS. 12 and 13), or the surgical hub 5104 (FIG. 14), for example. In one instance, the primary display 119 for the visualization system 108 (see FIG. 2) can be the display screen 214004. In such instances, the visualization system 108 and the display screen 214004 thereof can be coupled to the imaging module 138 (see FIG. 3) of the surgical hub 106. Moreover, the situational awareness of the surgical hub 106 can be configured to implement intelligent adjustments and/or recommendations to a clinician during a surgical procedure. For example, a situational awareness module of the surgical hub 106 can suggest that a clinician confirm a complete tissue seal, staple line alignment, and/or tumor removal, and, in response to the recommendation, the clinician can switch the surgical device 214002 from the primary mode to the secondary mode to interact with the display screen 214004. The clinician may interact with the display screen 214004 by zooming in on the tissue seal, augmenting the view on the display screen 214004 to check the tissue seal, and/or selecting a measurement tool from the graphical interface to measure the length of the tissue seal and/or another anatomical structure/landmark distance, for example. The clinician can respond to the surgical hub's prompt/recommendation without removing the surgical device 214002 from the surgical site and without taking his or her hands off the surgical device 214002.

In various instances, the clinician can interact with the display screen 214004 to control and/or provide input to the surgical hub. In instances in which the display screen 214004 is positioned outside of the sterile field, like the primary display 119 in FIG. 2, for example, the clinician can exercise control of the display screen 214004 outside of the sterile field through various surgical barriers, including the sterile field boundary and the patient's body. In other words, the clinician can indirectly control and/or command a second operating room system outside the sterile field with a first operating room system from completely within the sterile field.

In various aspects, a wearable device, i.e. a "wearable", can be configured to facilitate interaction with one or more communicatively coupled devices. For example, a clinician's wearable device within a sterile field can be used to interact with a surgical system outside of the sterile field. The wearable device can be an interactive device that is configured to interact with a remote system. In various instances, the wearable device can identify the wearer, i.e. the clinician wearing the device, and can identify surgical device(s) within a range of positions around the wearable device. Such a wearable device can determine if and how a clinician is holding a particular surgical device, for example. A wrist-worn wearable 214100 is shown in FIG. 32, and a finger-worn wearable 214102 is shown in FIG. 33. The wrist-worn wearable 214100 can be attached to the clinician's wrist "W" like a watch or a bracelet, for example. The finger-worn wearable 214102 can be attached to the clinician's thumb "T" or a finger "F" on the clinician's hand like a ring, for example.

The wearables 214100, 214102 each include a communication module 214104, which facilitates communication between the wearable 214100, 214102 and another surgical system. The communication modules 214104 can enable RFID tagging and/or near-field communication. The communications modules 214104 can emit a wireless signal 214106 indicative of a command or control from the clinician. For example, the wearables 214100 and 214102 can include a graphical user interface and/or a touchscreen. The clinician can engage the touchscreen or otherwise provide inputs to the graphical user interface to implement an adjustment to another surgical device. In one instance, the wearables 214100 and/or 214102 can be in signal communication with a visualization system and/or a display screen thereof. For example, the clinician can engage arrows 214110 on the user interface to pan the view on a primary display in a surgical theater, can adjust a zoom feature 214112 (FIG. 32) or 214113 (FIG. 33) to enlarge or reduce a view on the primary display, and/or select one or more icons 214114, 214116 on the user interface to adjust a view and/or data displayed on the display screen. Alternative graphics and input features are contemplated.

In one aspect, wearable devices can assist the clinician in interacting with displays, such as a primary display like the primary display 119 (FIG. 2) located outside the sterile field. For example, a wearable device can allow input from a surgeon to select, advance, re-size, and gesture with respect to a graphical user interface on the wearable device to adjust or control the primary display. For example, inputting a zoom-in operation on the wearable device can enlarge a portion of the video feed on the primary display. In one instance, the wearable device can include a simplified and/or minimized version of the information on the primary display, similar to a mobile device page displaying a simplified and/or minimized version of the information available on a desktop site. The wearable device can include a graphical user interface and a touchscreen, such that inputs to the graphical user interface on the touchscreen can be communicated to the primary display. In one such implementation, a clinician can interact with a sealed capacitive interactive surface on the wearable device, which can be worn like a watch of a wristband, with capacitive-infused latex gloves, for example.

In various instances, the wearable device can be tracked with image and/or object recognition techniques. For example, the image and/or video data can be processed utilizing a variety of machine vision, image processing, object recognition, and optical tracking techniques to track characteristics, properties, actions, and movements of the wearable device. For example, the wearable device can be recognized from images captured by the one or more cameras in the surgical theater utilizing a variety of image and/or object recognition techniques, including appearance and feature-based techniques. For example, the captured images can be processed utilizing an edge detection algorithm (e.g., a Canny edge detector algorithm) to generate outlines of the various objects within each image. An algorithm can then compare the templates of target objects (e.g. the target wearable device(s)) to the images containing the outlined objects to determine whether any of the target objects are located within the images. As another example, an algorithm can extract features from the captured images. The extracted features can be then be fed to a machine learning model (e.g., an artificial neural network or a support vector machine) trained via supervised or unsupervised learning techniques to correlate a feature vector to the targets. The features can include edges (extracted via a Canny edge detector algorithm, for example), curvature, corners (extracted via a Harris & Stephens corner detector algorithm, for example), and so on. Object recognition and tracking are further described in U.S. patent application Ser. No. 16/182, 255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, filed Nov. 6, 2018, and in U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE, filed Nov. 6, 2018, which are incorporated by reference herein in their respective entireties.

In certain instances, the wearable device can include an array of magnetics, which can be detected by a sensor within the surgical theater. Based on the position(s) of the wearable device detected by the sensor, the surgical system can determine movement of the wearable device. The movement can correspond to gestures by the clinician, for example. In such instances, the surgical system can determine one or more gestures by the clinician and, in various instances, such gestures can be communicated to another surgical system, such as an imaging system. For example, the gestures can correspond to input commands to a display screen of the imaging system. Magnetic sensing arrays are further described in U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE, filed Nov. 6, 2018, which is incorporated by reference herein in its entirety.

As another example, a wearable device can enable tracking of surgical devices by pairing with the surgical devices during a hand-off, such as when a handheld surgical instrument is picked up and/or handed to a clinician, for example. Referring primarily to FIG. 31, a clinician C is wearing two wearable devices-a first wearable device 214200 is on the clinician's right wrist RW, and a second wearable device 214202 is on the clinician's left wrist LW. The wearable devices 214200, 214202 can be configured to determine which surgical device is positioned in which hand of the clinician. For example, the first wearable device 214200 can pair with a first surgical device 214210 in the clinician's right hand, and the second wearable device 214202 can pair with a second surgical device 214212 when the second surgical device 214212 is handed to the clinician. In one implementation, the wearable device 214200 and/or 214202 can include a built-in RFID tag or near-field communication device that allows a handle within the hand of the clinician to recognize which clinician is holding the surgical device such that the surgical device can be automatically paired or repaired to the clinician. For example, the clinician's desired settings and/or most-frequently used features/adjustments specific to that particular surgical device can appear on the screen of the wearable device and/or be highlighted on the screen. Although wrist-worn devices are shown in FIG. 31, the reader will appreciate that alternative devices, such as rings and/or gloves, for example, are contemplated. Moreover, in certain instances, the clinician may only wear a wearable device on one wrist, such as the wrist of his dominant side, for example. In various instances, the wearable device can determine the orientation of the surgical tool with respect to the wearable device and, thus, with respect to the clinician's hand. In such instances, the surgical system may adjust the displays and controls based on the detected orientation of the surgical device in the clinician's hand.

For example, a first arrangement of controls and/or selections can be used for a right-handed clinician and a second, different arrangement of controls and/or selections can be used for a left-handed clinician. Additionally or alternatively, the arrangement of controls and/or availability of certain controls can depend on whether the surgical device is positioned in the clinician's dominant hand or non-dominant hand and/or based on the situational awareness from a surgical hub. In various instances, a wearable device can identify the clinician for example, and thus, include clinician-customized settings, including identification of the clinician's dominant hand, for example.

In various instances, the control of a surgical device can be shared by different control devices and/or the control of the surgical device can switch between multiple control devices. For example, a surgical device can include an autonomous control mode, in which the control inputs are provided by the device itself. For example, a clinician can engage an actuator on the surgical device (e.g. a button, switch, toggle, trigger, etc.) to actuate a surgical function (e.g. energy activation, clamping, firing, etc.) of the surgical device. Handheld surgical tools and robotic surgical tools can operate in an autonomous control mode, for example. For robotic surgical tools, the input control(s) can be at the surgeon's control console. For a handheld surgical tool, the input control(s) can be on the handle, for example.

In certain instances, the surgical device can be controlled and/or subjugated by another surgical device, which can selectively issue control inputs to the surgical device. In such instances, the surgical device can be referred to as a "controlled surgical device" and the other surgical device can be referred to as a "controlling surgical device." In one aspect, a mobile device having wireless communication features, such as a smart phone or tablet, for example, can be a controlling surgical device, which is selectively configured to provide control inputs to a controlled surgical device. Such a mobile device can be positioned in the sterile field. Additionally or alternatively, a wearable device can be a controlling surgical device, which is configured to provide control inputs to a controlled surgical device, as further described herein. In still other instances, a controlling surgical device, which can be paired and/or communicatively coupled to a controlled surgical device via a surgical hub, for example, can be configured to provide input controls to the controlled surgical device. In other instances, a display screen can be a controlling surgical device, which is configured to provide input controls to a controlled surgical device and/or a controlling surgical device can interact with a visualization system (e.g. as a cursor on a display screen) to provide input controls to the visualization system and/or another connected surgical device, i.e. the controlled surgical device(s). In the foregoing examples, the controlled surgical device can maintain at least some degree of autonomous control while the controlling surgical device(s) selectively exercise varying degrees of control over the controlled surgical instrument as well. In other instances, the input controls of the controlled surgical device can be disabled when control by a controlling surgical device is enabled and/or activated. In various instances, multiple surgical devices (including the controlled surgical device itself in certain instances) can simultaneously share control over the controlled surgical device. The reader will appreciate that various interactions of control interactions are contemplated in instances in which a surgical hub couples multiple surgical devices together into a cooperative surgical system.

In instances in which multiple surgical devices share control and/or alternative between control functionalities, a clinician may want to know which controlling surgical devices have control over a controlled surgical device at a particular time during the surgical procedure. For example, a surgical system can provide tactile, audible and/or visual indications to the clinician regarding the control mode.

In one aspect, the surgical system can provide various tactile, audio, and/or visual cues to the clinicians via a user interface, for example. The surgical system can highlight, emphasize, or otherwise bring attention to display cues on the user interface. Additionally or alternatively, the surgical system can nest or overlay data and key information. For example, certain information can be provided with an augmented reality view on the user interface and/or over a live feed of images, video, or other real-time data obtained by the surgical system. In another aspect, the surgical system can provide reinforced indication of a control function and/or a limitation thereof. For example, when control by a surgical device is disabled or otherwise not viable, the surgical device, control, or display can vibrate to communicate that the control input is not accepted.

As an example, if situational awareness indicates that a gross motor step is being performed during a surgical procedure, a clinician within the sterile field can be enabled to manipulate the position of a controlled surgical instrument via a controlling surgical device from within the sterile field, such as with a mobile tablet computer or wearable device located within the sterile field. However, if situational awareness indicates that a fine motor step is being performed during the surgical procedure, the control functionality of the controlling surgical device can be disabled such that only a clinician operating the surgical device, such as the clinician at the surgeon's console, for example, can provide input controls to the controlled surgical device. In such instances, the controlling surgical device can provide a tactile, auditory, and/or visual notice to the clinician within the sterile field to indicate that such control features are disabled. For example, the controlling surgical device can simply enter a "sleep" mode such that inputs cannot be provided by the sterile field clinician. In certain instances, the controlling surgical device can provide a verbal notice and/or beep, for example, to communicate that the desired control functionality is not viable. Additionally or alternatively, the controlling surgical device can vibrate or otherwise provide haptic feedback when the clinician in the sterile field attempts to provide a non-viable control input.

As another example, autonomous control of a surgical device can override control of the surgical device by another surgical device in various instances. For example, if a clinician at the surgeon's console is actively controlling a robotic tool, then a secondary control, such as the control input(s) provided by a clinician within the sterile field via a controlling surgical device, can be ignored. However, when the clinician at the surgeon's console stops actively controlling the robotic tool, the control inputs from the controlling surgical device within the sterile field can control the robotic tool. When the robotic tool is being controlled by the controlling surgical device within the sterile field, a user interface at the robotic console can utilize tactile, auditory, and/or visual cues to communicate that control is being shared with a controlling surgical device. Similarly, when the robotic tool is being controlled by the clinician at the surgeon's console, a user interface on the controlling surgical tool can indicate that its control functionality is disabled.

In various instances, controls for a surgical device can be configured to interface with one or more display(s) to communicate the interaction between the various controls. For example, a controlling surgical device can be configured to provide secondary control functionality over a controlled surgical device. Moreover, one or more indications can indicate or otherwise communicate the paired control function between the controlled surgical device and the controlling surgical devices. Such indications can be provided on one or more displays, such as the non-sterile displays 107 and 109, the primary display 119, the hub display 135, and/or a display in the surgeon's console 118 as depicted in FIGS. 2 and 3, for example. In one aspect, a touchscreen on a surgical device can be used by a clinician to interact with a primary surgical hub display. For example, a surgical device in the sterile field can include a capacitive touchscreen display. Surgical devices such as handheld surgical instruments, robotic tools, wearables, and display screens can include a touchscreen within the sterile field. In various instances, a clinician in the sterile field can slide, scroll, and/or otherwise configure a primary surgical hub display from the touchscreen within the surgical field. For example, by scanning, zooming, or otherwise adjusting the view on the touchscreen within the sterile field, the clinician can scan, zoom, or otherwise adjust the primary display for the surgical hub.

In various instances, a secondary device can contain controls that are only pairable with other devices to link command and control functions. For example, the secondary device can be a controller for controlling one or more other surgical devices. In various instances, the secondary device, or controlling surgical device, can be a screen located within the sterile field. For example, the secondary device can be a mobile device, such as a tablet or mobile phone, for example, that includes a screen. The screen can be a touchscreen, for example, which is configured to receive control input from a clinician in the sterile field. Additionally or alternatively, the display can include an embedded LED that highlights the control functionality in a way that pairs or connects the control functionality to a particular controlled surgical device.

Referring to FIGS. 34A and 34B, a display 214400 is shown. The display 214400 depicts a first plurality of information 214402 in FIG. 34A and a second plurality of information 214404 in FIG. 34B. A user can switch between the different views of FIGS. 34A and 34B by interacting with the display 214400. For example, the display 214400 includes a capacitive screen. In various instances, the clinician can interact with the display 214400 by touching an interface portion thereof. The display 214400 is configured to communicate different types of information to the clinician. For example, the display 214400 can communicate patient-specific information by selecting the PATIENT icon 214410, procedure-specific information by selecting the PROCEDURE icon 214412, and device-specific information by selecting the DEVICE icon 214414. The DEVICE icon 214414 has been selected in FIGS. 34A and 34B, as indicated with the highlighting around the DEVICE icon 214414. In other instances, the selected icon 214410, 214412, 214414 can be communicated in another manner, such as showing the selected icon 214410, 214412, 214414 in a different size, in a different position, in a different color, in a different style, and/or with another identifier such as an arrow or symbol relative thereto. Because the DEVICE icon 214414 is selected in FIGS. 34A and 34B, the device-specific information is portrayed. For example, the surgical devices being utilized during the surgical procedure are listed. In various instances, the display 214400 can selectively provide input commands to one or more of the surgical devices during the surgical procedure.

The listed surgical devices are a combination energy surgical device indicated with the first icon 214420, a surgical stapler indicated with the second icon 214422, and a suction/irrigation device indicated with the third icon

214424. The icons 214420, 214422, 214424 are textual words in FIGS. 34A and 34B; however, in other instances, the icons 214420, 214422, and 214424 can include graphics and/or can be symbols, such as a symbolic representation of the surgical device, for example. In certain instances, less than three or more than three surgical devices can be listed. In certain instances, only controllable surgical devices can be listed. In other instances, all of the surgical devices used during a surgical procedure can be listed; however, a clinician may only be able to select the controllable surgical devices from the list. Alternative surgical devices (e.g. an ultrasonic device, an electrosurgical device, a clip applier, a grasper, a knife, etc.) are contemplated.

The icon 214420 corresponding to the combination energy surgical device has been selected in FIG. 34A, and the icon 214422 corresponding to the stapler has been selected in FIG. 34B, as indicated with the highlighting around the respective icon 214420, 214422. In other instances, the selected icon 214420, 214422, 214424 can be communicated in another manner, such as showing the selected icon 214420, 214422, 214424 in a different size, in a different position, in a different color, in a different style, and/or with another identifier such as an arrow or symbol relative thereto. Because the icon 214420 corresponding to the combination energy surgical device has been selected in FIG. 34A, the available input commands correspond to commands for the combination energy surgical device. For example, a clinician can select a mode from the following list of modes 214430: ultrasonic, monopolar, bipolar, and blended. Alternative modes are also contemplated. The clinician can select the mode to control the energy modality applied by the combination energy surgical device. In other instances, additional adjustments can be controlled from the display 214400, such as the power level, duration, frequency, and so on. In various instances, the user input to the display 214400 can be communicated to the surgical hub by one or the various communication protocols described herein. Similarly, the surgical hub can relay the user input to the combination energy surgical device.

Referring now to FIG. 34B, because the icon 214422 corresponding to the surgical stapler has been selected, the available input commands correspond to commands for the surgical stapler. For example, a clinician can select a surgical function from a plurality of modes 214432 likes a clamping mode and a firing mode. In various instances, the modes 214432 can include additional sub-categories or adjustments, which can be selected from a menu. For example, clamping and/or firing can be performed manually or automatically, and/or the speed can be selected from a number of speeds, such as slow, medium, and fast. Alternative modes are also contemplated. The clinician can select the mode to control the surgical function of the surgical stapler. In various instances, the user input to the display 214400 can be communicated to the surgical hub by one or the various communication protocols described herein. Similarly, the surgical hub can relay the user input to the surgical stapler.

In various instances, pairing(s) between the display 214400 and the surgical device(s) can be communicated to the clinician. For example, the display 214400 can include at least one embedded LED that can be illuminated in a color that matches a color of a controlled surgical device and/or a color identifier on the controlled surgical device. In one aspect, the controlled surgical device can include a similar LED color identifier, for example. The embedded LED in the display 214400 can be illuminated in red, and a red LED on the paired surgical device can be illuminated to indicate pairing. In various instances, the display 214400 can be configured to control multiple surgical devices and, in such instances, multiple colors can be displayed on the display 214400 and the corresponding colors can be provided on respective identifiers throughout the surgical theater. For example, when the clinician has selected the first icon 214420 (FIG. 34A) corresponding to the combination energy surgical device, a portion of the display 214400 (e.g. the first icon 214420) can be illuminated in a particular color and an LED on the combination energy surgical device can be illuminated in the same color. Similarly, when the clinician has selected the second icon 214422 (FIG. 34B) corresponding to the surgical stapler, a portion of the display 214400 (e.g. the second icon 214422) can be illuminated in a particular color and an LED on the surgical stapler can be illuminated in the same color. Different colors can be assigned to different surgical devices. In various instances, the icons 214420, 214422, 214424 on the display can be illuminated in different colors and/or the icons can be highlighted with different colors. For example, the shapes around the selected icon 214420, 214422, 214424 can be a particular color that corresponds to an indicator on the paired surgical device.

The identifier on a controlled surgical device (e.g. the combination energy surgical device, surgical stapler, or suction/irrigation device) can be displayed in different ways or styles to communicate different control states. For example, when control by the display 214400 is disabled, the identifier can display a first pattern or style (e.g. the identifier can be a non-illuminated LED). When control by the secondary device is enabled, the identifier can display a second pattern or style (e.g. the identifier can be an illuminated LED), and/or when the secondary device is pairing with the controlled surgical device, the identifier can display a third pattern or style (e.g. the identifier can be a flashing LED). As described above, the color of the LED can corresponds to the color on the display 214400.

In various instances, one control interface can be used for activation of a surgical function and the other control interface can be used for sequencing through the instrument's modes. For example, a single trigger on the surgical device can effect different surgical functions, and the particular surgical function can be determined by the control interface on the display 214400. More specifically, with respect to FIG. 34A, a trigger or actuator on a combination energy surgical device can apply ultrasonic energy to tissue; however, if another mode was selected by the clinician, the same trigger or actuator would apply a different energy modularity to the tissue. In various instances, energy modalities and/or power levels can be controlled by the display 214400. Referring now to FIG. 34B, a trigger or actuator on the surgical stapler can be configured to clamp when the clamp function is selected on the display 214400, and the trigger can be configured to fire when the fire function is selected on the display 214400. Additionally adjustments (e.g. manual or automatic, clamping speed, firing speed, etc.) can be adjusted on the display 214400.

In other instances, multiple control devices can have activation capabilities for the same surgical device. For example, the display 214400 can include an activation control, which activates the surgical function on the surgical device. In certain instances, the power level for each activation can differ between the different control devices.

In one aspect, control of a secondary function can allow fine control from one controller and gross control from another controller. Secondary functions can include articulation of an end effector and distal head rotation, for example. In such instances, when gross control is desired, an integral or built-in device control, e.g. an autonomous control on the surgical device, can control the function. When fine control is desired, a secondary controller, such as the display 214400 can control the function. For example, when a clinician is utilizing another aspect of a surgical device, such as gripping a trigger for example, the fine control functionality can still be implemented with the secondary controller that is paired to the surgical device to create fine movements of the secondary function. In certain instances, certain functions like articulation and distal head rotation can be locked out when another function, like energy activation, clamping, or firing, is in operation. However, when the secondary controller for the secondary function is activated by another clinician or by another hand of the same clinician, the fine adjustment can be permitted though the clinician is using another control to operate the other function. In this mode of operation, the secondary function can have a limited operational envelope to ensure that the forces it applies and/or the rate at which it is operated are limited to produce the desired fine control or fine precision. Additionally or alternatively, it may override certain threshold limits to some extent because it is being directly controlled.

EXAMPLES

Various aspects of the subject matter described herein are set out in the following numbered examples:

Example 1: A computer-implemented method for contextually controlling a surgical device, the method comprising: receiving, by a computer system, perioperative data from the surgical device, the perioperative data associated with a surgical procedure; receiving, by the computer system, images from a scope, the images visualizing the surgical device during the surgical procedure; determining, by the computer system, an attribute of the surgical device from the images; determining, by the computer system, procedural context data based at least on the perioperative data and the attribute of the surgical device; and controlling, by the computer system, the surgical device according to the procedural context data.

Example 2: The computer-implemented method of Example 1, wherein the attribute comprises a type, an orientation, a position, a velocity, or an acceleration of the surgical device.

Example 3: The computer-implemented method of any one of Examples 1-2, wherein controlling the surgical device comprises changing, by the computer system, a state of the surgical device.

Example 4: The computer-implemented method of any one of Examples 1-3, wherein controlling the surgical device comprises changing, by the computer system, a function of an input of the surgical device.

Example 5: The computer-implemented method of any one of Examples 1-4, wherein controlling the surgical device comprises changing, by the computer system, information displayed by the surgical device.

Example 6: The computer-implemented method of any one of Examples 1-5, further comprising providing, by the computer system, a recommendation according to the procedural context data.

Example 7: The computer-implemented method of Example 6, further comprising: determining, by the computer system, whether the recommendation is of a first type or a second type; and displaying, by the computer system, the recommendation in a first manner according to whether the recommendation is of the first type or in a second manner according to whether the recommendation is of the second type.

Example 8: A computer-implemented method for contextually controlling a first surgical device, the method comprising: receiving, by a computer system, perioperative data from a second surgical device, the perioperative data associated with a surgical procedure; receiving, by the computer system, images from a scope, the images visualizing the second surgical device during the surgical procedure; determining, by the computer system, an attribute of the second surgical device from the images; determining, by the computer system, procedural context data based at least on the perioperative data and the attribute of the second surgical device; and controlling, by the computer system, the first surgical device according to the procedural context data.

Example 9: The computer-implemented method of Example 8, wherein the attribute comprises a type, an orientation, a position, a velocity, or an acceleration of the second surgical device.

Example 10: The computer-implemented method of any one of Examples 8-9, wherein controlling the first surgical device comprises changing, by the computer system, a state of the first surgical device.

Example 11: The computer-implemented method of any one of Examples 8-10, wherein controlling the first surgical device comprises changing, by the computer system, a function of an input of the first surgical device.

Example 12: The computer-implemented method of any one of Examples 8-11, wherein controlling the first surgical device comprises changing, by the computer system, information displayed by the first surgical device.

Example 13: The computer-implemented method of any one of Examples 8-12, further comprising providing, by the computer system, a recommendation according to the procedural context data.

Example 14: The computer-implemented method of Example 13, further comprising: determining, by the computer system, whether the recommendation is of a first type or a second type; and displaying, by the computer system, the recommendation in a first manner according to whether the recommendation is of the first type or in a second manner according to whether the recommendation is of the second type.

Example 15: A computer-implemented method for contextually controlling a surgical device, the method comprising: receiving, by a computer system, perioperative data from the surgical device, the perioperative data associated with a surgical procedure; receiving, by the computer system, images from a scope, the images visualizing a surgical site during the surgical procedure; determining, by the computer system, an attribute of the surgical site from the images; determining, by the computer system, procedural context data based at least on the perioperative data and the attribute of the surgical site; and controlling, by the computer system, the surgical device according to the procedural context data.

Example 16: The computer-implemented method of Example 15, wherein the attribute comprises a particulate concentration or sizes of particulates of the surgical site.

Example 17: The computer-implemented method of any one of Examples 15-16, wherein controlling the surgical device comprises changing, by the computer system, a state of the surgical device.

Example 18: The computer-implemented method of any one of Examples 15-17, wherein controlling the surgical device comprises changing, by the computer system, a function of an input of the surgical device.

Example 19: The computer-implemented method of any one of Examples 15-18, wherein controlling the surgical device comprises changing, by the computer system, information displayed by the surgical device.

Example 20: The computer-implemented method of any one of Examples 15-19, further comprising providing, by the computer system, a recommendation according to the procedural context data.

Example 21: The computer-implemented method of Example 20, further comprising: determining, by the computer system, whether the recommendation is of a first type or a second type; and displaying, by the computer system, the recommendation in a first manner according to whether the recommendation is of the first type or in a second manner according to whether the recommendation is of the second type.

Various additional aspects of the subject matter described herein are set out in the following numbered examples:

Example 1: A surgical system, comprising a sensor configured to detect a property of airborne particles in a fluid within a patient's abdominal cavity; a surgical device configured to implement a surgical function; and a control circuit comprising a processor and a memory storing instructions executable by the processor to: receive an input signal from the sensor indicative of the property of airborne particles in the fluid; and in response to the input signal, provide an output signal to the surgical device indicative of an adjustment to the surgical function.

Example 2: The surgical system of Example 1, wherein the sensor comprises at least one of an optical sensor, a laser sensor, an ultrasonic sensor, a magnetic resonance sensor, and a vortex shedding sensor.

Example 3: The surgical system of any one of Examples 1 and 2, wherein the property of airborne particles in the fluid comprises at least one of a particle type, particle size, particle concentration, particle velocity, and particle direction.

Example 4: The surgical system of any one of Examples 1-3, wherein the adjustment to the surgical function comprises at least one of proportionately increasing the surgical function based on the property of airborne particles in the fluid, adding a supplemental surgical function to the surgical function, and replacing the surgical function with an alternative surgical function.

Example 5: The surgical system of any one of Examples 1-4, wherein the surgical device comprises a generator configured to provide power to an energy device at a power level, and wherein the adjustment to the surgical function comprises adjusting the power level provided to the energy device from the generator.

Example 6: The surgical system of any one of Examples 1-4, wherein the surgical device comprises a smoke evacuator comprising a pump configured to operate at a speed, and wherein the adjustment to the surgical function comprises adjusting the speed of the pump.

Example 7: The surgical system of any one of Examples 1-4, wherein the surgical device comprises a smoke evacuator comprising a filtering system, and wherein the adjustment to the surgical function comprises adjusting a flow path through the filtering system of the smoke evacuator.

Example 8: The surgical system of Example 7, wherein the filtering system comprises a particulate filter, and wherein the flow path is diverted through the particulate filter when the input signal indicates an increase in particulate concentration of airborne particles in the fluid.

Example 9: The surgical system of any one of Examples 7 and 8, wherein the filtering system comprises a condenser, and wherein the flow path is diverted through the condenser when the input signal indicates an increase in aerosol concentration of airborne particles in the fluid.

Example 10: The surgical system of any one of Examples 1-4, wherein the surgical device comprises an operating room vent, and wherein the adjustment to the surgical function comprises adjusting the operating room vent to increase ventilation therethrough.

Example 11: The surgical system of any one of Examples 1-10, wherein the control circuit is further configured to: receive a plurality of input signals indicative of a plurality of properties of airborne particles in the fluid, wherein the plurality of input signals comprises the input signal; and in response to the plurality of input signals, provide the output signal to the surgical device indicative of the adjustment to the surgical function.

Example 12: A non-transitory medium storing computer readable instructions which, when executed, cause a surgical device to: receive an input signal from a sensor indicative a property of airborne particles in a fluid within a patient's abdominal cavity; and in response to the input signal, provide an output signal to a surgical device indicative of an adjustment to a surgical function.

Example 13: The non-transitory medium of Example 12, wherein the computer readable instructions, when executed, cause the surgical device to provide the output signal to a generator to adjust a power level of the generator.

Example 14: The non-transitory medium of Example 12, wherein the computer readable instructions, when executed, cause the surgical device to provide the output signal to a smoke evacuator to adjust a speed of a pump of the smoke evacuator.

Example 15: The non-transitory medium of Example 12, wherein the computer readable instructions, when executed, cause the surgical device to provide the output signal to a smoke evacuator to adjust a flow path through the smoke evacuator.

Example 16: The non-transitory medium of any one of Examples 12-15, wherein the computer readable instructions, when executed, cause the surgical device to adjust the surgical function by changing the surgical function in proportion to a change in the property of airborne particles in the fluid.

Example 17: The non-transitory medium of any one of Examples 12-16, wherein the computer readable instructions, when executed, cause the surgical device to adjust the surgical function by adding a supplemental surgical function in combination with the surgical function.

Example 18: The non-transitory medium of any one of Examples 12-17, wherein the computer readable instructions, when executed, cause the surgical device to adjust the surgical function by replacing the surgical function with an alternate surgical function.

Example 19: A method, comprising: receiving an input signal from a sensor indicative of a property of airborne particles in a fluid within a patient's abdominal cavity; and in response to the input signal, automatically providing an output signal to a surgical device indicative of an adjustment to a surgical function of the surgical device.

Example 20: The method of Example 19, further comprising: receiving a second input signal from the sensor indicative of the property of airborne particles in the fluid at a time subsequent to receiving the input signal; and in response to the second input signal, automatically providing a second output signal to a second surgical device indicative of an adjustment to a surgical function of the second surgical device, wherein the second surgical device is different than the first surgical device.

Example 21: A surgical device, comprising: an actuator configured to receive an input; and a control circuit configured to: receive a signal from a situationally-aware surgical hub indicative of a surgical state; receive an actuation signal from the actuator in response to the input; and implement a surgical function in response to the actuation signal, wherein the surgical function comprises a first surgical function when the surgical state corresponds to a first surgical state, wherein the surgical function comprises a second surgical function when the surgical state corresponds to a second surgical state, wherein the second surgical state is different than the first surgical state, and wherein the second surgical function is different than the first surgical function.

Example 22: The surgical device of Example 21, wherein the situationally-aware surgical hub comprises a situational awareness module, and wherein the surgical state comprises a step in a surgical procedure.

Example 23: The surgical device of any one of Examples 21 and 22, wherein the surgical state comprises identification of a suite of surgical devices currently in use in a surgical theater.

Example 24: The surgical device of any one of Examples 21-23, wherein the surgical state comprises a position of a portion of the surgical device.

Example 25: The surgical device of any one of Examples 21-24, wherein the surgical state comprises a position of a jaw of an end effector of the surgical device.

Example 26: The surgical device of any one of Examples 21-25, wherein the actuator is movable through a first range of motion from a first position to a second position and through a second range of motion from the second position to a third position, wherein movement of the actuator in the first range of motion is configured to activate the surgical function, and wherein movement of the actuator in the second range of motion is configured to scale a degree of the surgical function.

Example 27: The surgical device of any one of Examples 21-26, further comprising a Hall Effect sensor configured to determine the position of the actuator, wherein the first surgical function comprises an activation, and wherein the second surgical function comprises adjusting a degree of the activation based on the position of the actuator detected by the Hall Effect sensor.

Example 28: The surgical device of any one of Examples 21-26, further comprising a strain gauge operably coupled to the actuator, wherein the strain gauge is configured to determine a force of the input on the actuator, wherein the first surgical function comprises an activation, and wherein the second surgical function comprises adjusting a degree of the activation based on the force of the input detected by the strain gauge.

Example 29: The surgical device of any one of Examples 21-28, wherein the first surgical function is confined by a first maximum threshold and a first minimum threshold, wherein the second surgical function comprises a second maximum threshold and a second minimum threshold, wherein the first maximum threshold is different than the second maximum threshold, and wherein the first minimum threshold is different than the second minimum threshold.

Example 30: The surgical device of any one of Examples 21-29, wherein the first surgical state corresponds to a gross usage surgical step, and wherein the second surgical state corresponds to a precision usage surgical step.

Example 31: The surgical device of any one of Examples 21-30, wherein the actuator comprises at least one of a button, a switch, a toggle, a trigger, a lever, a dial, and a knob.

Example 32: The surgical device of any one of Examples 21-31, wherein the control circuit comprises a processor and a memory communicatively coupled to the processor.

Example 33: A non-transitory medium storing computer readable instructions which, when executed, cause a surgical device to: receive a signal from a situationally-aware surgical hub indicative of a surgical state; receive an actuation signal in response to an input applied to an actuator of a surgical device; and implement a surgical function in response to the actuation signal, wherein the surgical function comprises a first surgical function when the surgical state corresponds to a first surgical state, wherein the surgical function comprises a second surgical function when the surgical state corresponds to a second surgical state, wherein the second surgical state is different than the first surgical state, and wherein the second surgical function is different than the first surgical function.

Example 34: A system, comprising: a screen configured to selectively display a recommendation to a clinician in an operating room; and a control circuit comprising a processor and a memory in signal communication with the processor, wherein the memory stores instructions executable by the processor to: receive a signal from a situationally-aware surgical hub indicative of a surgical state; determine a priority level of the recommendation based on the surgical state; and communicate the priority level of the recommendation via the screen.

Example 35: The system of Example 34, wherein the control circuit is further configured to select one or more recommendations from a plurality of possible recommendations based on the surgical state.

Example 36: The system of Example 35, wherein the control circuit is further configured to adjust the priority level of the recommendation based on an anticipated surgical action, and wherein the anticipated surgical action is based on the surgical state.

Example 37: The system of Example 36, wherein the anticipated surgical action is based on a position of a surgical device at a surgical site.

Example 38: The system of any one of Examples 34-37, wherein an elevated priority level is communicated with at least one of marking, emphasizing, highlighting, and flashing.

Example 39: The system of any one of Examples 34-38, wherein the screen is positioned on a surgical device.

Example 40: The system of any one of Examples 34-39, further comprising an imaging system comprising a video monitor positionable in the operating room, wherein the screen is positioned on the video monitor.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A system, comprising:
   an ultrasound emitter positionable to transmit ultrasound waves toward a fluid at a surgical site;
   an ultrasound receiver positionable at the surgical site to receive at least a portion of the ultrasound waves transmitted by the ultrasound emitter; and
   a control circuit communicably coupled to the ultrasound emitter and the ultrasound receiver, wherein the control circuit is to determine a property of a fluid at the surgical site based on the ultrasound waves received by the ultrasound receiver.

2. The system of claim 1, further comprising a scope comprising a distal end, wherein the ultrasound emitter is positioned on the distal end of the scope.

3. The system of claim 2, further comprising a visualization system comprising the scope and a display, wherein the visualization system is to transmit an image obtained by the scope of the surgical site to the display.

4. The system of claim 1, wherein the visualization system further comprises a camera.

5. The system of claim 1, further comprising a surgical device comprising a device distal end, and wherein the ultrasound receiver is positioned on the device distal end of the surgical device.

6. The system of claim 5, wherein the surgical device comprises an end effector.

7. The system of claim 1, wherein the property of the fluid comprises at least one of a flow rate, a flow directionality, and a concentration of a particulate within the fluid.

8. The system of claim 1, wherein the portion of the ultrasound waves received by the ultrasound receiver indicate a Doppler shift, and wherein the property of the fluid is determined based on the Doppler shift.

9. The system of claim 1, wherein the ultrasound emitter and the ultrasound receiver are positioned on opposite sides of the fluid to form a non-contact pass-through detection system.

10. The system of claim 1, wherein the ultrasound emitter and the ultrasound receiver are spaced apart from the fluid.

11. The system of claim 1, wherein the ultrasound emitter and the ultrasound receiver are positioned on the same side as the fluid to form a non-contact reflection detection system.

12. A system, comprising:
    an ultrasound emitter positionable to transmit ultrasound waves toward a surgical site;
    an ultrasound receiver positionable at the surgical site to receive at least a portion of the ultrasound waves transmitted by the ultrasound emitter; and
    a control circuit communicably coupled to the ultrasound emitter and the ultrasound receiver, wherein the control circuit is to determine a property of the surgical site based on the ultrasound waves received by the ultrasound receiver.

13. The system of claim 12, wherein the property of the surgical site is a surface feature located on a tissue at the surgical site.

14. The system of claim 12, wherein the property of the surgical site is a presence of a fluid on a tissue at the surgical site.

15. The system of claim 12, wherein the property of the surgical site is a flow rate of a fluid located within the surgical site.

16. The system of claim 12, wherein the portion of ultrasound waves received by the ultrasound receiver indicate a Doppler shift, wherein the porperty comprises a property of a fluid at the surgical site, and wherein the property of the fluid is determined based on the Doppler shift.

17. A non-contact sensor, comprising:
    an ultrasound emitter positionable to transmit ultrasound waves toward a fluid at a surgical site;
    an ultrasound receiver positionable at the surgical site to receive at least a portion of the ultrasound waves transmitted by the ultrasound emitter; and
    a control circuit communicably coupled to the ultrasound emitter and the ultrasound receiver, wherein the control circuit is to:
      determine a property of a fluid at the surgical site based on the ultrasound waves received by the ultrasound receiver; and
      adjust a parameter of a surgical device based on the property of the fluid at the surgical site.

18. The non-contact sensor of claim 17, wherein the surgical device is a smoke evacuation system, and wherein the control circuit is to further:
    differentiate between a first type of particulate in the fluid and a second type of particulate in the fluid; and
    adjusts the parameter of the smoke evacuation system based further on a first concentration of the first type of particulate in the fluid and a second concentration of the second type of particulate in the fluid.

19. The non-contact sensor of claim 17, wherein the control circuit is to further transmit a recommended surgical function during a surgical procedure based on the determined property of the fluid at the surgical site.

20. The non-contact sensor of claim 17, wherein the portion of ultrasound waves received by the ultrasound receiver indicate a Doppler shift, and wherein the property of the fluid is determined based on the Doppler shift.

* * * * *